(12) United States Patent
Hansen et al.

(10) Patent No.: US 12,399,194 B2
(45) Date of Patent: Aug. 26, 2025

(54) AUTOMATED METHOD AND SYSTEM FOR OBTAINING AND PREPARING MICROORGANISM SAMPLE FOR BOTH IDENTIFICATION AND ANTIBIOTIC SUSCEPTIBILITY TESTS

(71) Applicant: BD KIESTRA B.V., Drachten (NL)

(72) Inventors: Timothy R. Hansen, Spring Grove, PA (US); Rick Holtz, Essex, MD (US); Martijn Kleefstra, Surhuisterveen (NL); Raphael Rodolphe Marcelpoil, Corenc (FR); Rick Pierpont, Apex, NC (US); Brent Ronald Pohl, Timonium, MD (US); Alyssa Shedlosky, Reisterstown, MD (US); Scott Shindledecker, Jarrettsville, MD (US); Edward Skevington, Stewartstown, PA (US); Kerry Lynn Smith, York, PA (US); Timothy Wiles, Ocean Isle Beach, NC (US)

(73) Assignee: BD KIESTRA B.V., Drachten (NL)

( * ) Notice: Subject to any disclaimer, the term of this patent is extended or adjusted under 35 U.S.C. 154(b) by 1271 days.

(21) Appl. No.: 17/136,670

(22) Filed: Dec. 29, 2020

(65) Prior Publication Data
US 2021/0116471 A1 Apr. 22, 2021

Related U.S. Application Data

(62) Division of application No. 15/575,665, filed as application No. PCT/US2016/034554 on May 27, 2016, now Pat. No. 10,921,336.

(60) Provisional application No. 62/318,494, filed on Apr. 5, 2016, provisional application No. 62/269,545, filed on Dec. 18, 2015, provisional application No. 62/167,593, filed on May 28, 2015, provisional application No. 62/167,577, filed on May 28, 2015.

(51) Int. Cl.

| | | |
|---|---|---|
| *G01N 35/10* | (2006.01) | |
| *C12M 1/26* | (2006.01) | |
| *C12Q 1/04* | (2006.01) | |
| *C12Q 1/24* | (2006.01) | |
| *G01N 1/38* | (2006.01) | |
| *G01N 35/00* | (2006.01) | |
| *G01N 35/04* | (2006.01) | |

(52) U.S. Cl.
CPC ............ *G01N 35/10* (2013.01); *C12M 33/04* (2013.01); *C12Q 1/04* (2013.01); *C12Q 1/24* (2013.01); *G01N 1/38* (2013.01); *G01N 35/00029* (2013.01); *G01N 35/00871* (2013.01); *G01N 35/0099* (2013.01); *G01N 35/04* (2013.01); *G01N 2035/00039* (2013.01); *G01N 2035/00306* (2013.01); *G01N 2035/0401* (2013.01); *G01N 2035/103* (2013.01); *G01N 2035/1032* (2013.01)

(58) Field of Classification Search
None
See application file for complete search history.

(56) References Cited

U.S. PATENT DOCUMENTS

| | | | |
|---|---|---|---|
| 5,266,272 | A | 11/1993 | Griner et al. |
| 6,096,272 | A | 8/2000 | Clark et al. |
| 6,175,112 | B1 | 1/2001 | Karger et al. |
| 6,323,035 | B1 | 11/2001 | Kedar et al. |
| 10,132,821 | B2 | 11/2018 | Silbert et al. |

(Continued)

FOREIGN PATENT DOCUMENTS

| | | |
|---|---|---|
| CN | 101542263 A | 9/2009 |
| CN | 102361968 A | 2/2012 |

(Continued)

OTHER PUBLICATIONS

Decision to Grant issued by the Russian Patent Office on Jan. 22, 2020 for Application No. 2017144892.

(Continued)

*Primary Examiner* — Paul S Hyun
(74) *Attorney, Agent, or Firm* — Botos Churchill IP Law LLP

(57) ABSTRACT

A method and automated apparatus for locating and selecting a colony of microorganisms on a culture dish and subjecting the obtained sample to a plurality of downstream tests including a test to identify the microorganism and a test to identify the susceptibility of the microorganism to antibiotics. The method includes the automated steps of locating and selecting a colony of microorganisms on a culture dish; obtaining a sample of the selected colony of microorganisms; preparing a suspension of a sample of microorganisms automatically by submerging the pick tool with the sample in a suspension, after which the pick tool is vibrated in at least the vertical direction to release the sample from the pick tool in the suspension. The turbidity of the suspension is monitored to ensure that the concentration of microorganism in suspension is sufficient so that the suspension is used a source for sample for both identification and antibiotic susceptibility of the microorganisms in the sample. The apparatus and system optionally provide for downstream processing of samples prepared for antibiotic susceptibility testing (AST). Such apparatus includes further processing after inoculation of an AST panel for the AST test. Such further processing includes capping and transferring inoculated panels to AST instrument.

7 Claims, 27 Drawing Sheets

(56) References Cited

U.S. PATENT DOCUMENTS

| | | | |
|---|---|---|---|
| 2002/0155590 A1* | 10/2002 | Gebrian | G01N 35/025 422/63 |
| 2003/0183301 A1 | 10/2003 | Massaro | |
| 2004/0054286 A1* | 3/2004 | Audain | G01N 35/10 600/449 |
| 2008/0063562 A1 | 3/2008 | Hoover | |
| 2008/0072664 A1 | 3/2008 | Hansen et al. | |
| 2008/0286086 A1 | 11/2008 | Fink et al. | |
| 2011/0296931 A1 | 12/2011 | Warhurst | |
| 2012/0009558 A1 | 1/2012 | Armstrong et al. | |
| 2013/0324568 A1 | 12/2013 | Verdonck | |
| 2014/0242570 A1 | 8/2014 | Botma et al. | |
| 2015/0086971 A1 | 3/2015 | Botma et al. | |
| 2017/0097368 A1 | 4/2017 | Botma et al. | |
| 2017/0336426 A1 | 11/2017 | Botma et al. | |
| 2018/0364264 A1 | 12/2018 | Botma et al. | |

FOREIGN PATENT DOCUMENTS

| | | |
|---|---|---|
| CN | 103958661 A | 7/2014 |
| CN | 104364659 A | 2/2015 |
| CN | 206975048 U | 2/2018 |
| CN | 208367018 U | 1/2019 |
| DE | 112010002799 T5 | 11/2012 |
| EP | 0688863 A2 | 12/1995 |
| JP | H07327662 A | 12/1995 |
| JP | 2001507240 A | 6/2001 |
| JP | 2002202315 A | 7/2002 |
| JP | 2011101617 A | 5/2011 |
| JP | 2012073197 A | 4/2012 |
| JP | 2014528723 A | 10/2014 |
| JP | 2015512650 A | 4/2015 |
| RU | 2541775 C2 | 2/2015 |
| WO | 9848980 A1 | 11/1998 |
| WO | 2013048249 A1 | 4/2013 |
| WO | 2013147610 A2 | 10/2013 |
| WO | 2013165615 A2 | 11/2013 |
| WO | 2015114121 A1 | 8/2015 |
| WO | 2016028684 A1 | 2/2016 |
| WO | 2016051267 A2 | 4/2016 |
| WO | 2016164712 A1 | 10/2016 |
| WO | 2016172527 A2 | 10/2016 |
| WO | 2016191646 A2 | 12/2016 |
| WO | WO2017054788 | 4/2017 |

OTHER PUBLICATIONS

First Examination Report issued in Australian application No. 2016267580 on Sep. 15, 2020.
International Search Report from PCT Application No. PCT/US2016/034554 mailed Dec. 16, 2016.
Notice of Reason for Refusal issued in Japanese application No. 2017-561973 on Jun. 30, 2020.
Notification of First Office Action issued in Chinese application No. 201680030939X on Oct. 10, 2020.
Preliminary Office Action issued in corresponding Brazilian Patent Application No. BR1120170255510 dated Jul. 26, 2020.
Translation of JP-2011101617-A (published May 26, 2011) downloaded from Espacenet on Nov. 17, 2019 (Year: 2011).
U.S. Appl. No. 15/513,448, filed Mar. 22, 2017.
First Examination Report issued in corresponding Australian Patent Application No. 2021215255 dated Oct. 18, 2022, (3 pp.).
Office Action from corresponding Korean Application No. 10-2017-7037784 dated Oct. 20, 2022 (15 pp.).
Office Action issued in corresponding Japanese Patent Application No. 2017-561973 dated Sep. 13, 2022, (25 pp.).
Office Action from corresponding Japanese Application No. 2021-144990 dated Nov. 17, 2022 (9 pp.).
Office Action from corresponding Brazilian Application No. 112017025551-0 dated Oct. 3, 2022 (9 pp.).
Office Action from corresponding Brazilian Patent Application No. 12 2023 006901-3 dated Jul. 11, 2023 (11 pp.).
Extended European Search Report issued in corresponding EP application No. 24159965.3 on Jun. 6, 2024., pp. 18.
Japanese Decision on Rejection issued in JP application No. 2017-561973 on May 6, 2021, 7 pp.
Japanese Office Action issued in corresponding JP application No. 2021-144990 dated May 30, 2023 (7 pp.).
Brazilian Unfavorable Opinion issued in corresponding BR application No. BR122023006901-3 on Jul. 11, 2023 (11 pp.).
Chinese Office Action issued in CN Application No. 2021115138599 dated Dec. 24, 2024., 35 pgs.
Chinese Search Report Issued in CN Application No. 2021115138599 dated Dec. 24, 2024., 4 pgs.
Examination Report No. 1 issued in corresponding AU application No. 2023285895 on Jan. 9, 2025., pp. 3.
Second Office Action issued in Chinese Patent Application No. 2021115138599 on Jul. 12, 2025, pp. 36.

* cited by examiner

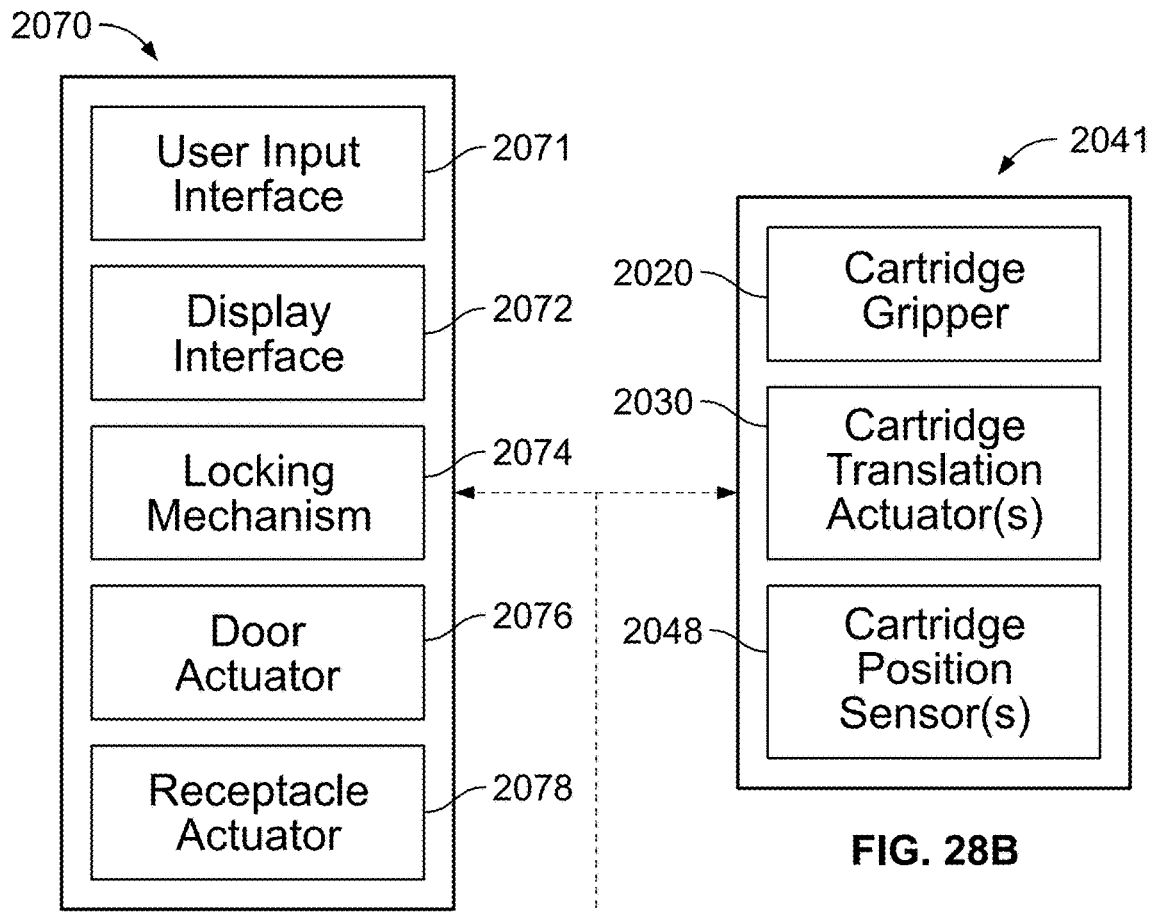
FIG. 28A
FIG. 28B
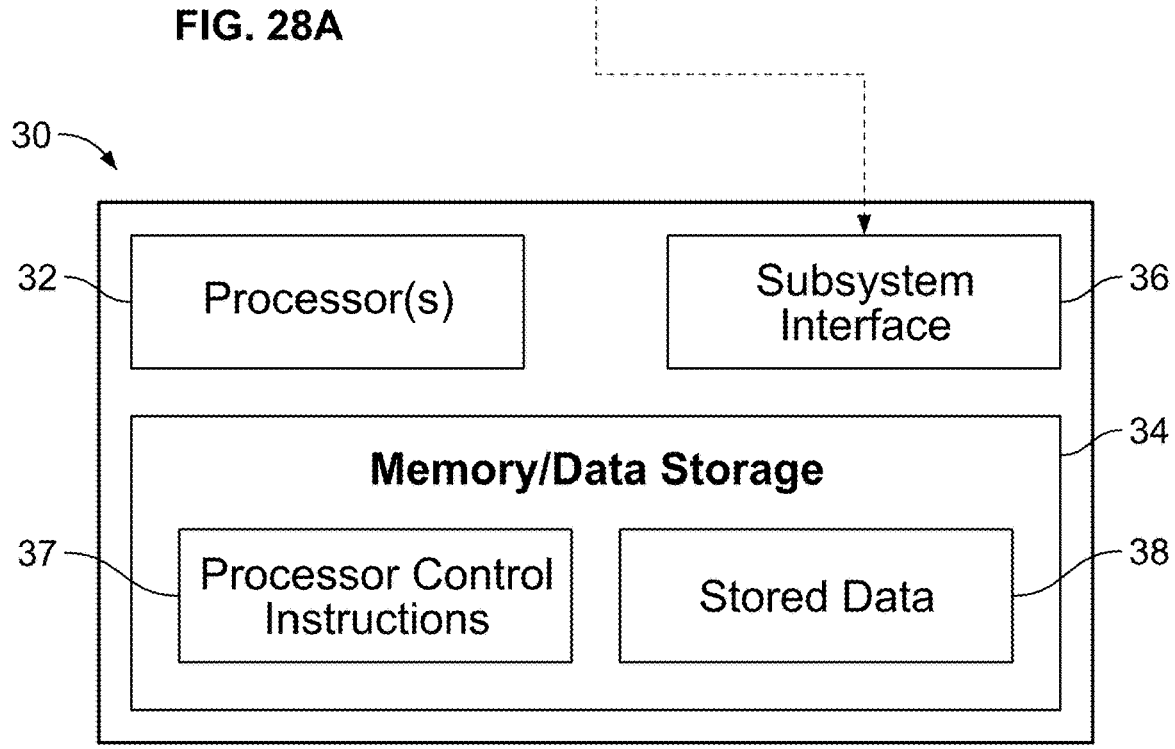
FIG. 28C

AUTOMATED METHOD AND SYSTEM FOR OBTAINING AND PREPARING MICROORGANISM SAMPLE FOR BOTH IDENTIFICATION AND ANTIBIOTIC SUSCEPTIBILITY TESTS

CROSS-REFERENCE TO RELATED APPLICATIONS

The present application is a divisional of U.S. application Ser. No. 15/575,665, filed Nov. 20, 2017, allowed, which application is a national phase entry under 35 U.S.C. § 371 of International Application No. PCT/US2016/034554 filed May 27, 2016 published in English, which claims priority from U.S. Provisional Application No. 62/167,577 filed May 28, 2015, U.S. Provisional Application No. 62/318,494 filed Apr. 5, 2016, U.S. Provisional Application No. 62/167,593 filed May 28, 2015, and U.S. Provisional Application No. 62/269,545 filed Dec. 18, 2015, all of which are incorporated herein by reference.

BACKGROUND OF THE INVENTION

Methods and system for locating and selecting a colony of microorganisms and identifying microorganisms using mass spectrometry, in particular MALDI-TOF-MS (Matrix Assisted Laser Desorption and Ionization Time-of-Flight Mass Spectrometry) and the systems for performing are known. Such systems and methods are described in WO2013/147610 to Botma et al., the disclosure of which is incorporated by reference herein.

MALDI-analysis is a useful tool for solving structural problems in biochemistry, immunology, genetics and biology. Samples are ionized in the gas phase and a time of flight (TOF) analyzer is used to measure ion masses. TOF analysis begins when ions are formed and are accelerated to a constant kinetic energy as they enter a drift region. They arrive at a detector following flight times that are proportional to the square root of their masses. A mass spectrum is created because ions of different mass arrive at the detector at different times.

Mass spectrometry generally can be a powerful tool in the fields of drug discovery and development, genotyping, and proteome research. MALDI, a specific type of mass spectrometry, has already been used for characterization and identification of bacteria and microorganisms. Current trends in research are to analyze larger and larger numbers of samples using quantities of individual samples ranging from the micro-mole levels to atomic-mole levels. As a result, samples are also becoming smaller and there exists the need for efficient and reliable acquisition of the correct amount of micro-organisms and accurately depositing a sample of the acquired amount on a target plate used in the MALDI-instrument.

In a typical MALDI TOF MS operation, the sample to be analyzed is spotted or deposited on a MALDI target plate that can be metal or other material that will allow for sample ionization. The commonly accepted method for preparing a MALDI target plate is to directly spot or smear a sample suspected to contain microorganism from plated media onto the target plate. After addition of the sample, matrix reagents are often added to support sample ionization. In some cases extraction reagents are also added. In other cases, an off-line extraction step may be required prior to adding the sample to the target plate.

Once the target plate is prepared, it is positioned in a fixed position in the MALDI-instrument. The target plate has a plurality of depositing spots (e.g. from 24 to 384 depositing spots on a single target plate) and these depositing spots have a fixed orientation with regard to the edges of the target plate. The target plate is positioned on an X-Y stage so that an obtained sample of a colony of microorganisms can be deposited on a selected depositing spot. A high voltage potential is maintained between the target plate and a metal grid. This voltage can be maintained or pulsed, depending upon the desired results and a vacuum is created in the chamber. A laser is fired into the sample/matrix and a plume of ions is formed. The voltage difference is used to accelerate the ions up a flight tube so that they can be analyzed. The analysis directly relates the time of flight to the mass of the ionized component.

Several parameters can affect the quality of the results, including flatness of the target, amount and type of matrix, concentration of the sample, conductivity of the sample target, accuracy of placement on the depositing spot, as well as other variables.

Because the process requires picking the colony and depositing it directly on the plate, the picked sample cannot be used as a sample source of other analysis. Consequently, if it is desired to perform another test on the sample, another portion of the sample must be acquired to perform the test. Because multiple colony picks are required for multiple tests, there is increased processing time required and the potential for discrepant results due to differences between the two picked samples. Therefore an automated, an efficient method and system that obtains a sample of microorganism from a colony and subjects that obtained sample to multiple tests continue to be sought.

BRIEF SUMMARY OF THE INVENTION

In order to solve at least one of the problems mentioned above the present invention provides an automated method and system for locating and selecting a colony of microorganisms on a culture dish and identifying microorganisms in the selected colony using MALDI and at least one other test. The method includes the automated steps of: locating and selecting a colony of microorganisms on a culture dish; obtaining a sample of the selected colony of microorganisms; preparing a suspension for the obtained sample; dispensing a portion of the obtained sample onto a target plate and placing the target plate in an apparatus for performing MALDI for identification of the sample of the selected colony of microorganisms; and using or transferring another portion of the suspension for another test. In one embodiment the second test is an antibiotic susceptibility test (AST). The AST could be using exiting automated AST methods (BD Phoenix or Vitek) or could be with Kirby-Baur/disk diffusion, disk dilution, broth and agar dilution or other methods.

In one embodiment, the suspension is prepared in a cuvette. The suspension in the cuvette is inspected using a nephelometer to determine if the turbidity of the sample is a value within a predetermined range of values determined to be suitable for the MALDI test. If not, the amount of sample or the amount of diluent in the suspension is adjusted to provide a suspension with a target turbidity value. Once an aliquot of suspension is removed from the cuvette for MALDI, the suspension is again inspected and the turbidity of the suspension determined by nephelometry. This time the turbidity of the suspension is evaluated to determine if the turbidity is within a range of turbidity values suitable for using the sample in a second test (e.g. an AST test). If not, the amount of diluent in the suspension is adjusted to provide a suspension having a suitable turbidity.

All steps are done automatically, which obviates the problems mentioned above for the greater part because automation avoids undesired variance and mistakes, which leads to incorrect results from the MALDI-instrument, additional costs and loss of time. By automating each of the steps these problems can be overcome to at least a large extent. In the present field it has been taken for granted that at least some of the steps only could be performed manually, however in contrast hereto the present invention provides the possibility for the first time to automate all the steps necessary for locating and selecting a colony of microorganisms and identifying microorganisms in the selected colony using MALDI.

By completely automating the preparation of a suspension the invention provides an accurate and reproducible method of using suspensions for MALDI identification and AST or other testing. The method further comprises the automated step of overlaying an aliquot of a MALDI matrix solution on the dispensed sample suspension on the target plate. In some embodiments, the dispensed sample suspension deposited on the target plate is allowed to dry before the aliquot of MALDI matrix solution is overlaid. A further embodiment would include spotting of an extraction reagent, such as formic acid prior to the matrix reagent for enhanced results.

This alternative method of using a suspension is furthermore extremely useful in case another test or analysis is to be performed on the sample of the colony of microorganisms. Such additional analysis can in a particularly reproducible and efficient manner be realized in an embodiment of a method according to the invention in which the method further comprises the automated steps of: obtaining a second aliquot of the sample suspension; depositing the second aliquot of sample suspension in a broth for AST testing; and transferring the inoculated AST broth tube to an apparatus for performing a susceptibility test or another additional analysis. Consequently the inventive method can be used to automatically obtain or pick a sample which can be fed into available ID/AST instruments including but not limited to BACTEC™, Phoenix, MGIT, VITEK, and BacT/Alert.

A fully integrated embodiment of the automated method includes the previously described steps combined into a single process flow. Specifically, a stage for a culture dish carrying microorganisms is provided. The culture dish is positioned on the stage. An automated pick tool having an automated positioning device with a pick tool holder for holding the pick tool (e.g. a pipette) is provided. The positioning device is arranged for positioning the pick tool in a starting position above the culture dish and for automatically lowering and raising a pick tool towards and away from the culture dish and for positioning a pick tool in a transfer position, respectively. The pick tool is positioned in the pick tool holder of the positioning device. The pick tool is placed in the starting position above the culture dish, and is automatically lowered towards the culture dish into contact with the microorganism to pick up a sample of the microorganism. The pick tool is automatically raised carrying the sample of the microorganism away from the culture dish to the transfer position. An automatic suspension medium dispenser is provided for automatically dispensing a suspension medium in a suspension tube held in the suspension tube holder. The automatic dispenser automatically supplies an initial amount of suspension medium into the suspension. The positioning device automatically moves the pick tool from above the culture dish to a position above a suspension. The positioning device lowers and raises the pick tool into and away from a suspension medium contained in a suspension tube, and optionally positions the pick tool in a waiting position above the suspension tube, respectively. The positioning device oscillates the pick tool in a linear vertical movement for a period of time while the pick tool with the sample of the microorganism is submerged in the suspension medium. After the period of time has elapsed the pick tool is raised away from the suspension medium contained in the suspension tube to the waiting position. A turbidity meter (also referred to herein as a nephelometer) is provided for performing measurements of the turbidity of a suspension medium contained in a suspension tube held in the suspension tube holder. At least after the period of time during which the pick tool is oscillated has elapsed the turbidity of the suspension medium contained in the suspension tube held in the suspension tube holder is measured by the turbidity meter and a final measurement value indicative of the measured turbidity is provided.

A controller communicatively connected to the positioning device, the transferring device, the automatic suspension medium dispenser and the turbidity meter for automatically controlling the movement of the positioning device, the movement of the transferring device, the operation of the automatic suspension medium dispenser and the operation of the turbidity meter, respectively. The controller controls and monitors the suspension and operates to provide a suspension having turbidity within the specification as previously described.

The invention further relates to an apparatus for automatic preparation of a suspension of a sample of microorganisms for performing the above-described method for automatically selecting a colony of microorganisms on a culture dish and preparing a suspension of a sample of microorganisms and using that suspension to test for at least both microorganism identification and antibiotic susceptibility. The apparatus has:
  a stage for a culture dish carrying the microorganism;
  a pick tool and a positioning device with a pick tool holder for holding a pick tool.
The positioning device is arranged for positioning a pick tool in a starting position above the culture dish and for automatically lowering and raising the pick tool towards and away from the culture dish and for positioning a pick tool in a transfer position, respectively;
  a suspension tube station for holding a suspension tube;
  an automatic suspension medium dispenser for automatically dispensing a suspension medium in a suspension tube held in the suspension tube station;
  a positioning device for automatically transferring a pick tool from the transfer position of the positioning device to a position above a suspension tube held in the suspension tube holder, and for lowering and raising a pick tool into and away from a suspension medium contained in a suspension tube, and for positioning a pick tool in a waiting position above a suspension tube held in the suspension tube holder, respectively, the transferring device further being arranged for oscillating a pick tool in a linear vertical movement for a period of time;
  a turbidity meter for performing measurements of the turbidity of a suspension medium contained in a suspension tube held in the suspension tube holder and for providing a final measurement value indicative of the measured turbidity; and
  a controller communicatively connected to the positioning device, the automatic suspension medium dispenser and the turbidity meter for automatically controlling the movement of the positioning device, the movement of the transferring device, the operation of the automatic suspension medium dispenser and the operation of the turbidity meter, respectively.

The controller:
a) determines whether the final turbidity measurement value is above a first threshold value (a maximum value) previously stored in a memory of the controller, if yes the controller being arranged for performing step b) (dilution); or whether the final turbidity measurement value is identical to or below the first threshold value and identical to or above a second threshold value (a minimum value) previously stored in the memory of the controller, the first threshold value being greater than the second threshold value, if yes the controller being arranged for performing step c) (acceptable turbidity); or whether the final measurement value is below the second threshold value, if yes the controller being arranged for performing step d) (concentration);
b) controls the automatic suspension medium dispenser to supply an additional amount of suspension medium into the suspension tube;
c) provides a signal that the suspension tube with the suspension can be removed from the suspension tube holder for further processing; or
d) positions the further pick tool in the pick tool holder of the positioning device in the manner described for the first pick tool.

In a further embodiment of an apparatus according to the invention the controller is arranged for controlling the turbidity meter such that measuring the turbidity of the suspension medium contained in the suspension tube held in the suspension tube holder by the turbidity meter is started before the pick tool is submerged in the suspension medium contained in the suspension tube.

In an advantageous embodiment of an apparatus according to the invention in step d) the first pick tool is provided as further pick tool; and the controller is arranged for controlling the transferring device for positioning the further pick tool in the pick tool holder of the positioning device.

Preferably the controller is arranged for determining the additional amount of suspension medium based on the initial amount of suspension medium, the final measurement value and the value of the first and/or second threshold value. In particular the controller is arranged for controlling the automatic suspension medium dispenser in the manner previously described.

A fully automatic device according to the invention when the apparatus comprises an automatic culture dish positioning and removing device for automatically positioning and removing a culture dish comprising the microorganism on and from the stage, respectively, the controller being arranged for being communicatively connected to the automatic culture dish positioning and removing device for controlling the operation of the automatic culture dish positioning and removing device, and for automatically positioning a culture dish comprising the microorganism on the stage, and when the apparatus comprises an automatic suspension container positioning and removing device for automatically positioning and removing a suspension container in and from the suspension container station, respectively, the controller being arranged for being communicatively connected to the automatic suspension tube positioning and removing device for controlling the operation of the automatic suspension container positioning and removing device, and for automatically positioning a suspension container in the suspension container station. In this case it is then preferred that the controller is arranged for allowing a culture dish to be automatically removed from the stage by the automatic culture dish positioning and removing device only after the signal that the suspension container with the suspension can be removed from the suspension tube container station for further processing has been provided. In addition the controller is then preferably arranged for automatically removing a suspension container from the suspension container station by the automatic suspension container positioning and removing device only after the signal that the suspension container with the prepared suspension therein can be removed from the suspension container station.

The invention still further relates to a method for automatically depositing a drop of a suspension containing a sample of a colony of microorganisms on a depositing spot of a target plate for MALDI. In certain embodiments, the system and method is configured to use the suspension as a source for sample for another test (e.g. AST).

The apparatus has a pipetting tool and a positioning device with a pipetting tool holder for holding the pipetting tool. The positioning device is arranged for positioning the pipetting tool in a starting position above a suspension tube holding the suspension containing a sample of a colony of microorganisms. The pipetting tool automatically lowers and raises the pipetting tool into and out of the suspension and positions the pipetting tool in a transfer position, respectively.

The pipetting tool picks up an amount of suspension, raises the pipetting tool with the amount of suspension to the transfer position. The pipetting tool has a pressurizable chamber closed by a controlled valve for containing the amount of suspension medium.

A target plate holder is provided that holds the target plate, the target plate having at least one depositing spots.

The apparatus positions the target plate in the target plate holder.

The apparatus includes a transferring device for automatically transferring the pipetting tool from the transfer position of the positioning device to a position above one of the depositing spots of the target plate, and for lowering the pick tool (e.g. a pipette tip) to a predefined distance above the target plate, pressurizing the chamber (e.g. a pressure in a range of about 0.5 bar to 1.1 bar although such is by way of illustration and not limitation), and opening the valve for such a time that a drop of suspension with a volume in a range of about 0.5 µl to 3.0 µl is deposited on the one of the depositing spots. Preferably the shape of the pipetting tool is such that depositing the drop of suspension on the target plate takes place in a splash free manner.

The suspension tubes are then moved to a second location. In the second location, the turbidity of the suspension is adjusted for a second test (e.g. AST). The second location has a nephelometer for determining whether the turbidity of the suspension is suited for the second test. The pipetting tool is then used to obtain additional suspension and use that suspension to inoculate a vessel for another test (e.g. AST).

In one embodiment, described is an automated system for preparing a single sample suspension from which aliquots are removed for identification (ID) of microorganisms in the sample and a second test. In other embodiments the automated system prepares a single sample suspension from which aliquots are removed for identification (ID) of microorganisms in the sample and antibiotic susceptibility (AST) of microorganisms. The system includes at least a first section for performing an ID assay. The first section has a mechanism that receives a plated culture either by automatic conveyance or manually. The system either includes or is in communication with an imaging apparatus that optically inspects the culture plate and, from that image, colonies of interest are discerned. In alternate embodiments, the images are obtained and the colonies selected prior to the plated culture being received by the system. The system includes a mechanism that identifies the location of a colony of interest on the plate and for designating the colony of interest to be picked for testing. The first section includes an automated robotic pick tool. The system also includes a controller that communicates with the robotic pick tool, directing the robotic pick tool to acquire a pipette, and then carry the pipette to a location above the colony of interest. The top of the plate has been removed to facilitate colony pick. The robotic pick tool then lowers the pipette so that the tip is in contact with the colony of interest.

Subsystem interface 36, which can include an external bus, that couples controller 30 to the preparation system 1000, cartridge transfer instrument 2000, and cartridge testing instrument 2050. In particular, instructions and data are communicated between controller 30 and components 2070 via the subsystem interface 36.

After the colony has been picked the controller instructs the robotic pick tool to convey the picked sample to a first sample suspension preparation station. Optionally, the system captures a new image of the plate after the colony has been picked to verify that the pick is from the correct location. The first sample suspension station has a suspension dispenser that dispenses the sample suspension liquid into a suspension tube or cuvette or other suitable receptacle. The first sample suspension station has a nephelometer or other suitable apparatus for measuring turbidity of the liquid in the suspension tube or cuvette. The robotic pick tool releases the sample carried from the culture plate into the suspension liquid. In some embodiments the robotic pick tool oscillates the pick tool to facilitate release of the sample into the suspension. The nephelometer measures the turbidity of the suspension wherein the automated system, in response to a turbidity measurement that is outside a predetermined turbidity value, adjusts the suspension to make it acceptably heavy (i.e. turbid) for an ID assay.

The first section further includes a first robotic pipettor. The first robotic pipettor obtains a first aliquot of the suspension at the first station and inoculates a receptacle for use in the ID assay. The receptacle (e.g. a MALDI plate) is then removed from the system and conveyed to an apparatus for performing MALDI. The receptacle can be conveyed either mechanically or manually. The suspension tube or cuvette is then conveyed to a location in the first section where the remaining portion of the suspension is prepared to be used in a second assay (e.g. an AST assay). The conveyance is by automated means using a conveyor.

The first section has a second nephelometer at the second sample suspension station for measuring the turbidity of the suspension. The first robotic pipettor is further configured to adjust the concentration of the sample in the suspension tube or cuvette to a predetermined concentration for the second assay and for obtaining a second aliquot of the sample suspension having adjusted concentration and inoculating a sample tube for the AST assay with the second aliquot of suspension. Such sample tubes are commonly referred to as AST broth tubes.

The system optionally has a second section for preparing a panel for the AST assay. The automated system has an automated mechanism for conveying the inoculated sample tube from the first section to the second section. In one embodiment, the inoculated sample tube is lowered through a deck for the second sample suspension station and conveyed under the deck, emerging from beneath the deck in the second section. The second section has a second robotic pipettor that obtains an aliquot from the inoculated sample tube and inoculates the AST panel with the obtained aliquot. The second section also has a means by which to store, dispense, manipulate and press caps 99 (see FIG. 26) into cap holes in the inoculated panel. The second section also has a robot that loads the inoculated panel into an apparatus in which AST is performed, the AST apparatus configured to have at least two doors, the first door receiving the panel from the panel loading robot. The second door is for manually loading of inoculated panels by a user. The AST apparatus is not required to be located in the second section of the system and can be adjacent thereto. The second section also has a controller which is communicatively connected to the AST instrument to request, schedule access and open to the first door of the AST instrument.

BRIEF DESCRIPTION OF THE DRAWINGS

The invention will be further explained with reference to the following figures.

FIG. 28A is a diagram of example testing instrument components that can be automatically controlled by the controller of FIG. 3.

FIG. 28B is a diagram of example transfer instrument components that can be automatically controlled by the controller of FIG. 3.

FIG. 28C is a diagram further illustrating the exemplary architecture of the controller of FIG. 3.

DETAILED DESCRIPTION

Figure 1:
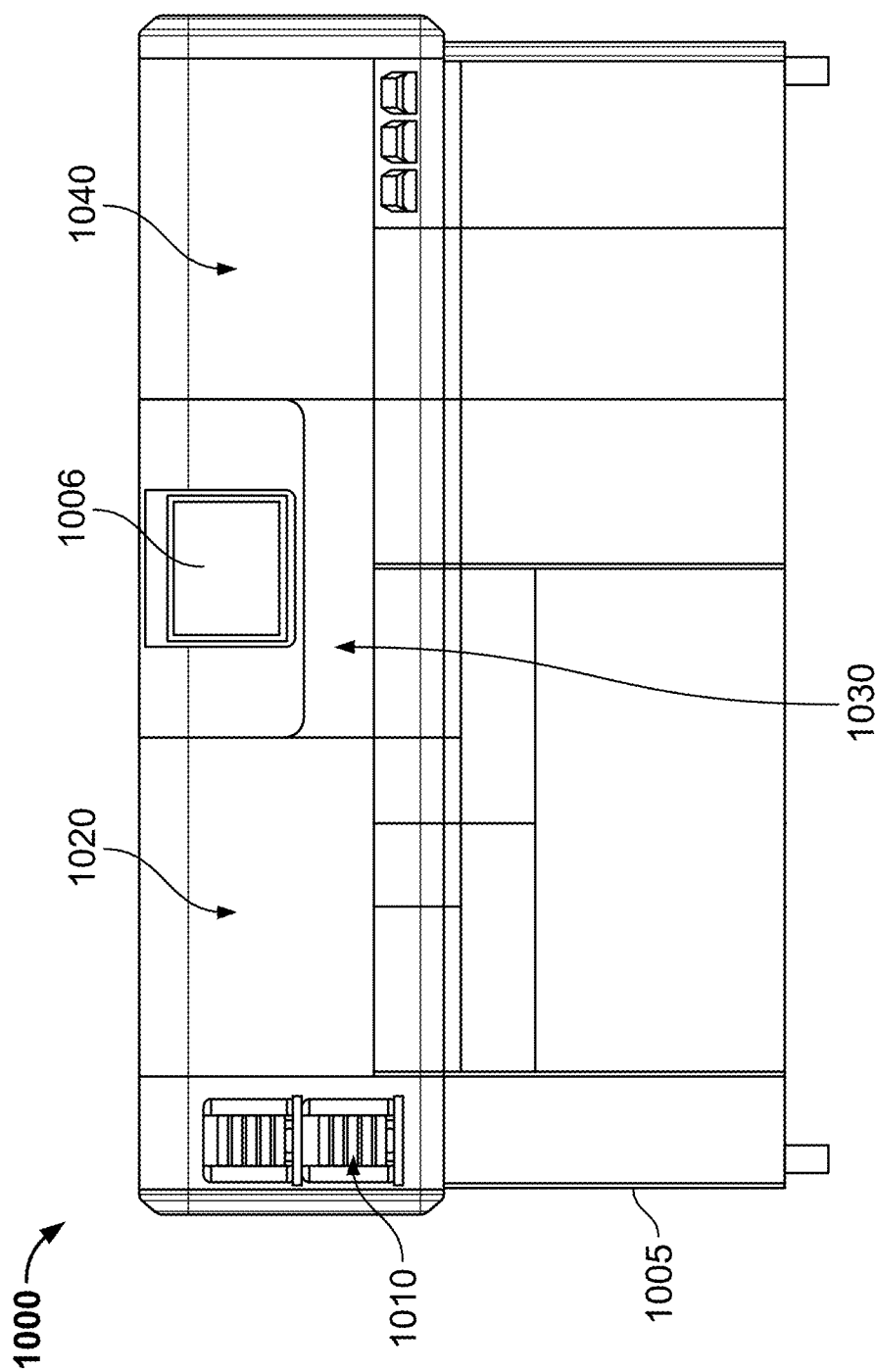
FIG. 1 is a front view of a system according to an embodiment of the present disclosure including a system housing.

As used herein, a "cuvette" and/or "micro-cuvette" and/or "low volume cuvette" and/or "LVC" and/or "sample vessel" or "vessel" is the container suitable for receiving a liquid suspension. The container is preferably made of optically transparent plastic or glass that is designed to hold a test sample in a specific space and orientation for testing or processing.

As used herein, "algorithms" are one or more mathematical instructions that are used to manipulate values of data to make a decision based on a mathematical value and then produce a corrected or more accurate data value representative of the desired output.

As used herein, an "amplifier" is an electronic circuit that is used to take a smaller original electronic signal and increase its amplitude to produce a proportionately larger new signal that is representative of the original signal. Suitable amplifiers are well known to those skilled in the art and are not described in detail herein.

As used herein, an "analog to digital converter" or "A/D converter" is an electronic device that is capable of taking a variable electrical signal and turning it into a number that is representative of the amplitude of the original signal.

As used herein, "dilution" means a solution or suspension produced by adding a liquid diluent to a concentrated solution or suspension resulting in a new suspension or solution with a lower uniform concentration of sample in the solution or suspension than the original.

As used herein, "laser" or "laser diode" is an electronic device that produces a concentrated and focused beam of light when an electrical current is applied.

As used herein, "light attenuation filter" is a device that is placed into a light path to absorb and reduce the amount of light as it passes through the filter resulting in the light that was passed through the filter to have proportionally lower intensity than the original light source.

As used herein, "light emitting diode" or "LED" is an electronic device that emits light of a specific type and orientation when an electrical current is applied.

As used herein, "McFarland" is a unit of measure of the amount of solid particulates dispersed in a fluid or liquid suspension.

As used herein, "nephelometer" is an instrument that is capable of measuring the amount of solid particles in a suspension. As used herein, "nephelometry" refers to a method by which the amount of suspended solids in a suspension can be measured.

As used herein, "photo-diode" and/or "detector" is an electronic device used to measure the intensity of light in a given environment.

As used herein, "saturated" and/or "saturation" is the point at which the detector has reached the maximum amount of output signal it is capable of producing. For example, adding more light to the photo-detector past saturation does not produce any further change in the detector output signal which has reached its maximum operating capability.

As used herein, "suspension" is a solution in which solids are distributed uniformly in the liquid.

As used herein, "turbidity" is the measurement of the amount of suspected solids in a solution (i.e., cloudiness of a liquid sample).

Described herein are methods and systems for preparing a single suspension from a colony of microorganisms that is the source for sample for determining both the ID and antibiotic susceptibility of the selected colony of microorganisms. Since the sample used to characterize and identify microorganisms is normally obtained from a culture dish with a plurality of colonies grown on culture, it is important that a sample is obtained from a colony of interest. If samples are taken from non-interesting colonies the efficient use of time and the MALDI-instrument is compromised. The present invention contemplates an automated process for identifying and selecting a colony of interest among a plurality of colonies present on the dish. The process of discriminating colonies can be at least partly automated by providing a culture dish comprising a number of colonies of microorganisms, obtaining an initial image of the culture dish including all the colonies of microorganisms, displaying the initial image of the culture dish including all the colonies of microorganisms on a display, and selecting at least one colony of microorganisms from the initial image.

In this manner a researcher or analyst can select colonies of interest based on education and knowledge. In a particular embodiment the culture dish is provided with an individual identification identifying the culture dish, such as a bar code, and the method further comprises the step of storing the initial image of the culture dish including all colonies, storing information regarding the at least one selected colony of microorganisms, storing the identification of the culture dish in a memory of a central control computer. In an additional embodiment the researcher or analyst can manually enter processing instructions regarding the processing to which a selected colony of microorganisms of the culture dish is to be subjected, the processing instructions being stored in the memory of the central control computer for later use.

In one embodiment, the colonies on the plate are imaged according to the methods described in Provisional Patent Application No. 62/151,681 filed on Apr. 23, 2015 entitled "Colony Contrast Gathering" and also filed as PCT/US2016/028913 and also PCT/EP2015/052017 entitled "A System and Method for Image Acquisition Using Supervised High Quality Imaging" and which applications are incorporated herein by reference. The contrast of the different colonies against the culture medium provides the ability to discriminate colonies to facilitate automated colony pick. As noted elsewhere, the image of the plated cultures can be obtained in a separate apparatus prior to being received by the system described herein or the system herein can be integrated with a module in which such images are obtained.

After the initial image of the culture dish is obtained, the culture dish is incubated for a period of time to allow microorganisms on the plate, if present, to grow. In a further embodiment of the invention the method comprises the automated steps of positioning the culture dish on a stage for a culture dish, obtaining an image of the culture dish positioned in the stage, obtaining the identification of the culture dish, comparing the image obtained by the imaging device of the pick tool device with the stored initial image of the culture dish for obtaining information regarding the location of the selected colony of microorganisms and optionally for obtaining the processing instructions regarding the processes to be performed on the selected colony of microorganisms. By comparing the image of the culture dish when it is placed in the pick tool device with the initial image, the location of the selected colonies can be obtained automatically, for example by computerized image comparison.

In another embodiment, fiducial markings on the agar surface or on the culture dish can be used to re-locate colonies. These fiducial markings may be embedded on the plate during manufacturing, or applied by the user or by organic growth or incorporated on the dish or agar surface by any suitable means. Using a machine vision apparatus, another reference point such as the center of the dish is detected from which dish coordinates can be determined. A barcode is one example of a fiducial. The location of colonies on the dish can be determined in reference to their relative distance from the center and angular offset to the barcode zero offset. Once the relative location of the colony is determined when the dish can be moved to another system where the following two steps are performed. The dish is centered for example by mechanical means. The barcode zero offset is detected, for example by rotating the dish while having a fixed sensor to detect the presence of the barcode label and scan the barcode with a barcode scanner. At this point the center of the dish is known and the barcode zero offset is known and therefore the location of the previously referenced colonies can easily be calculated as they are stored as distance to the dish center and angular offset to the barcode label. The method as it is described here does not need a camera or computer vision system in the second system (colony picking system in this example), or any other system where the colony position information is required. The zero offset used in this example is to the barcode label but it could be any unique fiducial feature of the dish or applied to the dish as noted above.

One automated method and apparatus for picking up microorganisms from the surface of a culture medium is described in US Patent Publication No. 2014/0242570 (U.S. Ser. No. 14/347,841) entitled Method For Picking Up Cell Material And Assembly For Performing Said Method," to Botma et al. which is commonly owned and hereby incorporated by reference.

As described in Botma et al., in an advantageous embodiment the method further includes the steps of removing the pick tool a predetermined distance away from the contact position towards a check position and holding said pick tool in said check position and of measuring the electrical capacity of the system composed of the pick tool and the support in the check position. In some cases the sample material to be picked up is very sticky or slimy. When the pick tool, after making contact with such sample material, is removed away from the sample a thin thread may remain in contact between the pick tool and the sample material that remains in the culture dish. This thin thread can break and possibly contaminate the pick tool device. By measuring the electrical capacity of the pick tool and pick tool support in the check position, which for example can be a few millimeters above the culture dish, it is possible to detect the presence of such a thread so that appropriate measures can be taken. In those embodiments in which a pick tool holder is provided for removably holding a pick tool, the pick tool holder being adapted to grasp and release a pick tool, an automated response to detection of a remaining thread can be implemented. For example, the pick tool can be released from the pick tool holder if the electrical capacitance measured in the check position differs from the start electrical capacitance in the start position such that the pick tool falls into the culture dish, after which the culture dish may be discarded. These steps can easily be performed in an automated way so that no time consuming human intervention is necessary to discard the pick tool and culture dish.

In one embodiment, a pipette tip is used as to pick the colony from the surface of the culture medium (e.g. agar) on which the colony is disposed. The pipette can draw the colony into the tip using suction in one embodiment. In other embodiments, suction is not used to draw the colony into the pipette tip and only contact forces between the colony and pipette tip forces colony into the pipette tip.

In still a further embodiment of a method according to the invention the method comprises the step of automatic preparing a suspension of a sample of microorganisms. In such method the following steps are performed.

A first pick tool is provided along with a positioning device with a pick tool holder for holding a pick tool (e.g. the pipette tip pick tool described previously). The positioning device is arranged for positioning a pick tool in a starting position above the obtained location of the selected colony of microorganisms on the culture dish. The positioning device automatically lowers and raises a pick tool towards and away from the culture dish and positions the pick tool in a transfer position, respectively.

The first pick tool is positioned in the pick tool holder of the positioning device. The pick tool is then positioned in the starting position above the obtained location of the selected colony of microorganisms on the culture dish. The pick tool is then automatically lowered to contact the microorganism colony to pick up a sample of the microorganism. The pick tool is then automatically raised along with the collected sample of the microorganism away from the culture dish to the transfer position.

A suspension tube holder that holds at least one suspension tube is provided. The suspension tube is positioned in the suspension tube holder. Although referred to as a suspension tube herein, the vessel for the suspension can be a tube, vial, cuvette or other vessel for holding the suspension solution.

An automatic suspension medium dispenser is provided for automatically dispensing a suspension medium in a suspension tube held in the suspension tube holder. The automatic dispenser automatically supplies an initial amount of suspension medium into the suspension tube held in the suspension tube holder. A transferring device, which may be separate from the positioning device or as part of the positioning device, is also provided for automatically transferring a pick tool (having already collected a sample) to a position above a suspension tube held in the suspension tube holder. The transfer device lowers and raises the pick tool (and the sample carried by the pick tool) into and away from a suspension medium contained in a suspension tube. The transfer device also positions the pick tool in a waiting position above the suspension tube held in the suspension tube holder, respectively.

The transfer device oscillates the first pick tool in a linear vertical movement for a period of time while the first pick tool with the sample of the microorganism is submerged in the suspension medium so as to release the sample into the suspension medium and mix the suspension. After the period of time has elapsed the first pick tool is raised away from the suspension medium contained in the suspension tube to the waiting position. Alternatively, in lieu of oscillation to release the microorganism sample, repeated aspiration with a pipette tip pick tool while partially submerged in the suspension medium can be utilized to effectuate release of the microorganism and mixing of the suspension.

In the automated method a turbidity meter is provided that measures the turbidity of a suspension medium contained in a suspension tube held in the suspension tube holder. In one embodiment, that turbidity meter is as described in U.S. Provisional Patent Application Ser. No. 62/056,911 filed on Sep. 29, 2014 and PCT/IB2015/00272 (published as WO2016/051267) that are commonly assigned herewith, and which are incorporated by reference in their entirety herein.

After the period of time during which the pick tool is oscillated has elapsed, the turbidity of the suspension medium contained in the suspension tube held in the suspension tube holder is measured by the turbidity meter and a final measurement value indicative of the measured turbidity is provided.

In additional embodiments a controller that is communicatively connected to the positioning device, the transferring device, the automatic suspension medium dispenser and the turbidity meter is provided. Such controller automatically controls the movement of the positioning device, the movement of the transferring device, the operation of the automatic suspension medium dispenser and the operation of the turbidity meter, respectively.

Figure 6:
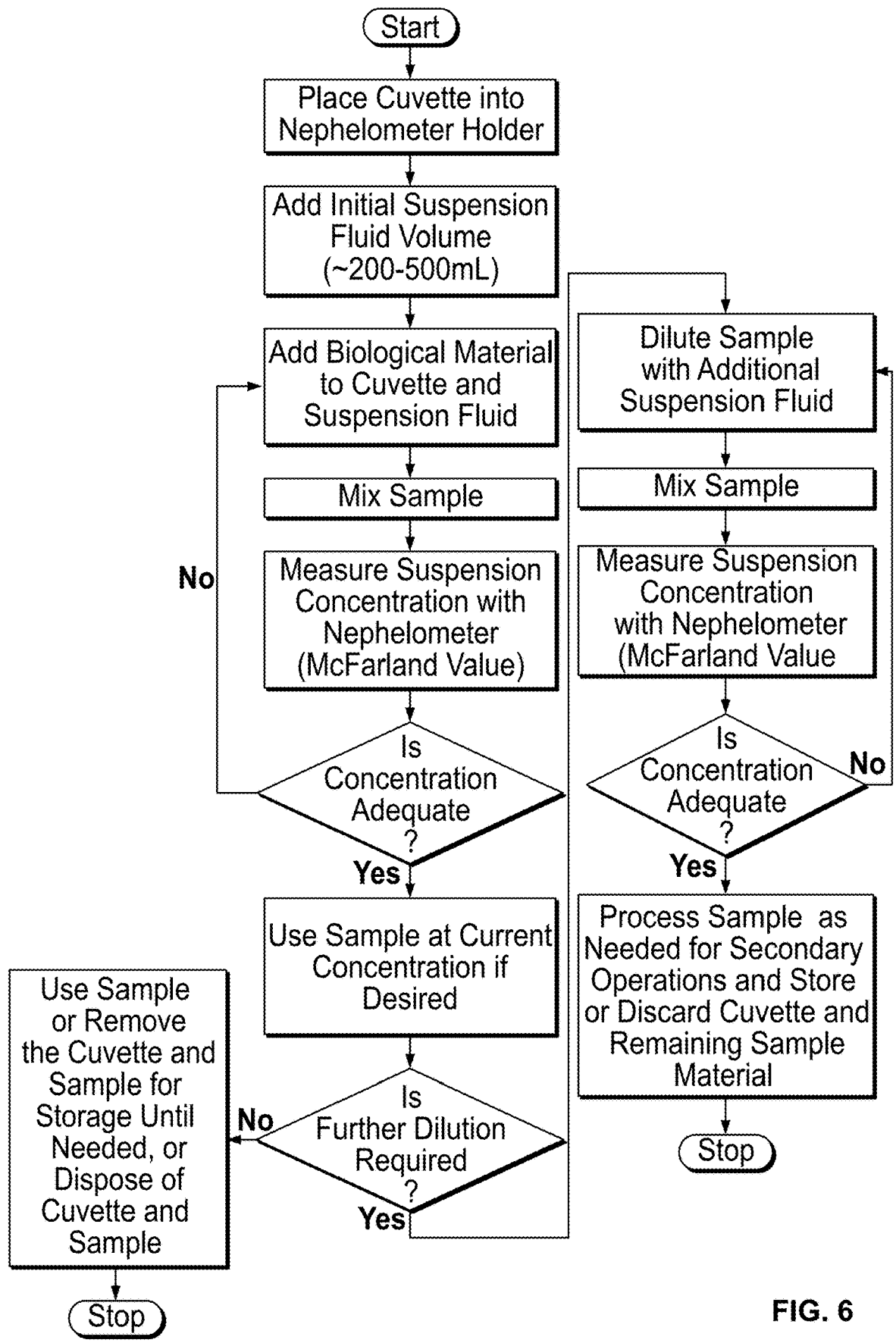
FIG. 6 is a process flow diagram illustrating one process embodiment for preparing a sample using the nephelometer of FIG. 4A.

Referring to FIG. 6, in one embodiment the controller determines whether the final turbidity measurement value is above a first threshold value (a maximum value) previously stored in a memory of the controller. If yes then step b) (dilution described below) is performed. If the final turbidity measurement is identical to or below the first threshold value and at or above a second threshold value previously stored in the memory of the controller, where the first threshold value is equal to or greater than the second threshold value, then step c) (acceptable turbidity described below) is performed. If the final measurement value is below the second threshold value, then step d) (increasing turbidity described below) is performed.

In step b) the automatic suspension medium dispenser is automatically controlled to supply an additional amount of suspension medium into the suspension tube. In step c) a signal is provided that the suspension tube with the suspension is removed from the suspension tube holder for further processing.

According to step d) a further pick tool is obtained and it is positioned in the pick tool holder of the positioning device as described above. The positioning device positions the further pick tool in the starting position above the culture dish, automatically lowers the further pick tool towards the culture dish into contact with the microorganism to pick up an additional sample of the microorganism, automatically raises the further pick tool with the sample of the microorganism away from the culture dish to the transfer position, all as described for the first pick. Although the pick tool described herein is a pipette, other suitable pick tools are described in U.S. Provisional Application No. 62/144,574 filed on Apr. 8, 2015 entitled "Device And Apparatus For Collecting Microbial Growth From A Semi-Solid Surface," and PCT/US2016/026625 filed on Apr. 8, 2016, which are incorporated by reference herein.

The transferring device automatically transfers the further pick tool with the additional sample of the microorganism from the transfer position of the positioning device to a position above the suspension tube held in the suspension tube holder, and lowers the further pick tool with the additional sample of the microorganism into the suspension medium contained in the suspension tube and oscillates the further pick tool in a linear vertical movement for a period of time while the further pick tool with the additional sample of the microorganism is submerged in the suspension medium. After the period of time has elapsed the pick tool is raised away from the suspension medium contained in the suspension tube to the waiting position. After the period of time during which the further pick tool is oscillated has elapsed the turbidity of the suspension medium contained in the suspension tube held in the suspension tube holder is measured by the turbidity meter and an additional final measurement value indicative of the measured turbidity is provided.

After the sample has been acquired, in yet another embodiment, the pipetting system can perform a series of rapid draws and dispenses of the pipette tip in the liquid suspension. For example, the pipetting system can repeat the series of withdraws up to about 24 times within a 20 second period and dispense about 250 μL of a 300 μL sample. The repetitive action creates high shear forces at the tip of the pipette. The high shear forces allow the dispersion of clumps or mucoid strands of the sample containing microorganisms to create a more uniform suspension.

In this manner it is possible to prepare a suspension of a sample of a microorganism in an advanced automatic manner while by means of the controller and the turbidity meter it is possible to provide a suspension tube containing a suspension medium which contains an amount of microorganism which is always sufficient (and reproducible) to perform a correct analysis of the microorganism.

In one additional embodiment of a method for automatic preparation of a suspension of a sample of microorganisms according to the invention the controller is arranged such that the step of measuring the turbidity of the suspension medium contained in the suspension tube held in the suspension tube holder by the turbidity meter is additionally performed during the period of time during which the pick tool is oscillated, wherein the turbidity meter is arranged for providing an on-line measurement value indicative of the measured turbidity during the period of time during which the pick tool is oscillated to the controller. In this way an extremely fast automatic determination of the amount of microorganism in the suspension can be obtained. In particular, if during oscillation the on-line measurement value of the turbidity is equal to or lower than the first threshold value and equal to or greater than the second threshold value the controller controls the movement of the transferring device such that the pick tool is raised to the waiting position, and the controller further provides a signal that the suspension tube with the suspension can be removed from the suspension tube holder for further processing. In this manner the oscillation of the pick tool is stopped when the suspension medium contains a sufficient amount of microorganisms, so that the method can be performed in an extremely time efficient manner.

The mutual arrangement of the pick tool and the sensors of the turbidity meter is such that, during the oscillation of the pick tool, the pick tool does not obstruct the pathway of the turbidity meter.

In a further embodiment of a method for automatic preparation of a suspension of a sample of microorganisms according to one embodiment herein, the controller is arranged such as to control the turbidity meter such that the step of measuring the turbidity of the suspension medium contained in the suspension tube held in the suspension tube holder by the turbidity meter is started before the pick tool is submerged in the suspension medium contained in the suspension tube. In this way it is, for example, possible to check whether the initial suspension medium used is not contaminated. Furthermore, this provides an indication of the starting value for the turbidity which is useful in determining the final measurement value.

In a still further embodiment of a method for automatic preparation of a suspension of a sample of microorganisms the method further comprises the step of providing a suspension tube holder for holding a suspension tube. The suspension tube holder can be adapted to rotate a suspension tube held in the rotatable suspension tube holder. In further embodiments the controller is arranged such that it is communicatively connected to the rotatable suspension tube holder for controlling the rotation of the suspension tube holder. The controller is further arranged such that the suspension tube is rotated during measurement of the turbidity of the suspension medium contained in the suspension tube. Such a rotation of the suspension tube allows turbidity measurements at a number of positions within the suspension tube which are rotationally spaced from each other leading to a more correct final measurement of the turbidity of the suspension. The rotation as such is not necessary for releasing the sample from the pick tool. The oscillation of the pick tool as described above is more than sufficient to release the sample.

Although a further pick tool can be used that is different from the first pick tool, the method can be performed in an economical way when in step d) the first pick tool is provided as further pick tool; and the positioning of the further pick tool in the pick tool holder of the positioning device is performed by the transferring device under control of the controller.

In a still further embodiment of a method for automatic preparation of a suspension of a sample of microorganisms according to the invention the additional amount of suspension medium is determined by the controller based on the initial amount of suspension medium, the final measurement value and the value of the first and/or second threshold value. This makes it possible to carefully control the amount of suspension medium that is used. As such, suspension medium is conserved.

Since, in some embodiments, the pick tool is oscillated in a vertical linear movement relative to the suspension tube, the horizontal cross section of the suspension tube can be relatively small. This makes it possible to use smaller suspension volumes. In one embodiment, the controller causes an initial amount of about 0.1 ml 5 ml of suspension liquid to be dispensed, and preferably less than about 1 ml (about 300 μl in one example). In other embodiments the volume of suspension liquid is about 0.5 ml to about 2 ml. In one embodiment, the dispensed volume is 300 μl. Such a relatively small amount of suspension medium is sufficient for preparing a correct suspension of a sample of microorganisms.

In such a method for automatic preparation of a suspension of a sample of microorganisms it is possible to use as a suspension vessel a tube, a vial or a cuvette having a maximum cross-section dimension of about 2 to about 12 mm, preferably about 3 mm, which is relatively small when compared to the traditional suspension tubes which have a diameter of about 16 mm. The tube can have a square, rectangular or round cross section and the actual cuvette shape is largely a matter of design choice. In one embodiment the tube is circular with a diameter of about 6 to about 12 mm. In one advantageous embodiment the diameter is about 10 mm. With such a relatively small suspension tube a correct release of the sample from the pick tool is obtained when the controller is arranged for controlling the oscillation of the transferring device such that the pick tool oscillates at a frequency between about 5 Hz to about 250 Hz. Selection of frequencies within this range is largely a matter of design choice and will depend on the constituents of the suspension being formed. For suspensions being formed of sample and solution that interdisperse easily, frequencies of 5-12 HZ may be adequate. For constituents that do not form a suspension as readily a frequency of about 100 HZ or higher may be required. Preferably the controller is arranged for controlling the oscillation of the transferring device such that the pick tool oscillates with an amplitude of about 0.5 mm to about 4 mm, preferably about 2 mm to about 3 mm, and most preferably about 1 mm, which results in an optimal release of the sample from the pick tool. In embodiments where the controller is arranged for controlling the oscillation of the transferring device such that the period of time during which the pick tool oscillates is about 3 seconds to about 120 seconds, preferably about 30-60 seconds, the complete sample can be released from the pick tool in virtually all cases. For efficiency and throughput it is advantageous if the oscillation is required for only about 3 to 10 seconds with 6 seconds being about the average minimum oscillation time.

The values for the frequency, amplitude and duration are dependent on the properties of the specific microorganism and, for example its adherence to the pick tool. In one embodiment, inspection by imaging can be used to deduce whether or not the sample has at least for the greater part been released from the pick tool by first using the above-mentioned preferred values. If there is still some material left on the pick tool than the vertical oscillation is repeated within the given ranges at different values.

The automated method for preparing a suspension of a sample of microorganisms additionally includes providing an automatic culture dish positioning and removing device for automatically positioning and removing a culture dish from the stage. The controller is communicatively connected to the automatic culture dish positioning and removing device for controlling the operation of the automatic culture dish positioning and removing device. In this manner positioning a culture dish (carrying the target microorganisms) on the stage can be performed automatically under control of the controller. In other embodiments an automatic suspension tube positioning and removing device is provided that automatically positions and removes suspension tubes in and from the suspension tube holder, respectively. The controller is communicatively connected to the automatic suspension tube positioning and removing device for controlling the operation of the automatic suspension tube positioning and removing device, so that positioning of a suspension tube in the suspension tube holder can be performed automatically under control of the controller. Advantageously, the controller is then arranged such that a culture dish is allowed to be automatically removed from the stage by the automatic culture dish positioning and removing device only after the signal that the suspension tube with the suspension can be removed from the suspension tube holder for further processing has been provided. In yet additional embodiments the controller is arranged such that a suspension tube holder is automatically removed from the suspension tube holder by the automatic suspension tube positioning and removing device only after the signal is provided that the suspension tube with the suspension can be removed from the suspension tube holder for further processing.

In still a further embodiment of a method according to the invention, an identifying mark is provided on the suspension tube. According to the method, the identifying mark of the suspension tube is stored together with the properties of the suspension with a link to the identity of the culture dish from which the selected colony of microorganisms was obtained in the memory of the central control computer. This ensures that the method can not only be automatically operated in an extremely efficient manner but also correct and fast processing of the obtained analysis results.

In a further embodiment of the method described herein a pipetting tool is provided (either separately or the pick tool device is adapted to receive and use pipettes) to deposit an aliquot (or multiple aliquots) of suspension onto a MALDI plate and also deposit an aliquot of suspension for other downstream analysis (e.g. AST). A positioning device is provided with a pipetting tool holder for holding the pipetting tool. The positioning device is arranged for positioning the pipetting tool in a starting position above the suspension tube. The positioning device automatically lowers and raises the pipetting tool into and out of the suspension and for positioning the pipetting tool in a transfer position, respectively. The pipetting tool is received by the pipetting tool holder of the positioning device. The positioning device positions the pipetting tool in the starting position above the suspension tube, lowers the pipetting tool into the suspension in the suspension tube, operates the pipetting tool to pick up an amount of suspension, and raises the pipetting tool with the amount of suspension to the transfer position. The pipetting tool has a pressurizable chamber closed by a controlled valve for containing the amount of suspension medium.

The method provides a target plate holder for holding a target plate, the target plate having at least one depositing spot. The target plate is positioned in the target plate holder. A transfer device is provided that automatically transfers the pipetting tool from the transfer position of the positioning device to a position above one of the depositing spots of the target plate, and lowers the pipetting tool to a predefined distance above the target plate. The chamber is pressurized to a pressure in a range of about 0.5 bar to 1.1 bar, and the valve is then opened for such a time that a drop of suspension with a volume in a range of about 0.5 to 3.0 µl is deposited on the depositing spot, in particular covering at most approximately half of the one of the depositing spots of the target plate. After which the pipetting tool is raised from the target plate. In dependence of the properties of the specific microorganism, e.g. its stickiness, the pressure and the opening time can be adjusted to obtain a small drop of suspension which can be reproducibly prepared and which as a result of the automated process can be deposited accurately on the target plate.

The pipetting tool is used to obtain more suspension in the manner previously described. The pipetting tool is then used to dispense the suspension into a vessel for other analysis (e.g. a suitable vessel for performing antibiotic susceptibility testing (AST)).

In order to avoid cross-contamination in a preferred embodiment of a method according to the invention the shape of the pipetting tool, in particular the dispensing tip thereof, is such that depositing the drop of suspension on the target plate or other vessel takes place in a splash free manner. It has appeared that depending on the kind of microorganism used, and especially the stickiness thereof, in addition to choosing a correct pressure in the range mentioned above and opening time of the valve in the range mentioned above a suitable shape of the pipetting tool ensures that a drop of suspension can be is deposited in a splash free manner.

In a further embodiment of a method an identifying mark is provided on the target plate and other vessel(s) for sample testing (e.g. AST) and optionally providing an identifying mark on the depositing spots of the target plate. According to the method the identifying mark of the target plate and depositing spots is stored together with the properties of the suspension with a link to the identity of the culture dish from which the selected colony of microorganisms was obtained, all stored in the memory of the central control computer. The method can not only be automatically operated in an extremely efficient manner but also the correct and fast processing of the obtained analysis results is achieved.

In an even further embodiment of the method, a prepared vessel, such as a vessel assisting in the performance of further testing such as AST, may be moved from a location in which the tube is inoculated with the microorganism suspension and other appropriate reagents to a second location where an additional pipettor pipettes the mixtures from the vessel and inoculates a cartridge used for testing. Such cartridge may be further positioned, after inoculation, by a robot, into a holding structure which holds the cartridge until it is retrieved by a cartridge transfer instrument. When available, the cartridge transfer instrument picks up or grips the cartridge from the holding structure and transfers the cartridge to another holding structure located within a testing instrument, such as an AST testing instrument.

Mass spectrometry, as practiced by MALDI or MALDI-TOF-MS, is used to identify microorganisms. In a MALDI-TOF-MS operation a sample of a colony of microorganisms is spotted or deposited on a target plate which is held in a fixed position in a MALDI-instrument. Such a target plate typically has a plurality of depositing spots (e.g., from 24 to 384 depositing spots on a single target plate). These depositing spots have a fixed orientation with regard to the edges of the target plate. The target plate is positioned on an X-Y stage so that an obtained sample of a colony of microorganisms can be deposited on a selected depositing spot. The location where a specific sample has been deposited is indicated by X-Y coordinates/parameters and is stored in a memory of a central control computer.

Although not depicted in detail in FIG. 2, a target plate 42 is illustrated as positioned below a transfer track 18 at a position indicated by B. A sample can be transferred along the transfer track 18 from a culture dish 3 and/or a suspension tube 11 to above the target plate at position B, where the sample is lowered to be deposited on a depositing spot of the target plate. Other transfer mechanisms other than those illustrated in FIG. 1 are contemplated. For example, deck mounted transfer mechanisms can be deployed.

The invention will be described detailed below with reference to preparing a suspension containing a sample and depositing the suspension on a depositing spot of a target plate. In general, a colony of microorganisms is automatically located and detected on a culture dish. A sample of the selected colony of microorganisms is obtained in an automated way, e.g. by a pick tool which is brought into contact with the colony.

When performing characterization and identification of microorganisms, normally a plurality of colonies is grown on a culture dish. In addition a plurality of different culture dishes are processed through the apparatus. As such, the invention provides the ability to identify each culture dish separately, e.g., by means of a bar code, and furthermore each colony of interest on a single culture dish is selected and given an identification mark. Hereto before the automated step of locating and selecting a colony of microorganisms on a culture dish, a culture dish determined to contain a number of colonies of microorganisms is provided. An initial image of the culture dish is obtained. The image includes all the colonies of microorganisms. The apparatus, or a device working in communication with the apparatus, displays the initial image of the culture dish, including all the colonies of microorganisms on a display, and selects at least one colony of microorganisms in the initial image. In this manner a researcher or analyst can select colonies of interest based on thorough education and knowledge. In one embodiment, imaging information is processed and colonies are identified for picking based upon specifications. Since each culture dish is provided with an individual identification identifying the culture dish, such as a bar code, the initial image of the culture dish including all colonies is stored, and information regarding the at least one selected target colony of microorganisms is stored (preferably with links given in the (electronic) initial image). All the information and identifications of the culture dish is stored in a memory of a central control computer that allows for a high degree of accuracy and processing integrity.

In this manner the only potential manual operation in the method and apparatus described herein is the act of selecting the colonies of interest. All of the data concerning the sample is processed in an automated way. Optionally, the researcher or analyst can manually enter processing instructions regarding the processing to which a selected colony of microorganisms of the culture dish is to be subjected. The processing instructions are also stored in the memory of the central control computer for later use. After this manual act all the further steps performed are automated in a reliable and efficient manner.

For this automated further processing the culture dish is automatically positioned on a stage for a culture dish of a pick tool device comprising an imaging device. An image of the culture dish positioned in the pick tool device is obtained, and together with the identification of the culture dish it is possible to compare this image obtained by the imaging device of the pick tool device with the stored initial image of the culture dish and thus derive information regarding the location of the selected colony of microorganisms and optionally regarding the processing instructions regarding the processes to be performed on the selected colony of microorganisms. By comparing the image of the culture dish when it is placed in the pick tool device with the initial image, the location of the selected colonies can be obtained automatically, for example by computerized image comparison. Furthermore each target plate is provided with an identifying mark and optionally each depositing spot of the target plate has an individual identification mark or location identifier. The vessel used for AST also bears an identifying mark to associate the results with the correct sample. After storing the identifying mark of the target plate and depositing spots together with the properties of the suspension with a link to the identity of the culture dish from which the selected colony of microorganisms was obtained in the memory of the central control computer a correct linking of the obtained MALI/AST results to the specific colony of microorganism under test is possible in a correct and automated way.

It has been discovered that then when the sample covers at most approximately half of the one of the depositing spots of the target plate, the analysis results obtained from the MALDI-instrument of the part of the depositing spot which initially was not covered with the sample are surprisingly extremely more accurate than the analysis results obtained from the MALDI-instrument of the part of the depositing spot which initially was covered with the sample. It is assumed that the crystallization which takes place after a drop of matrix material has been overlaid on the sample covering part of the depositing spot ensures that also the part of the depositing spot which was not covered contains an amount of sample material, and that this amount is extremely suitable for providing excellent analysis results. The physical or chemical processes which are the cause for this effect are, at the moment, unclear, but perhaps more clarity might arise when the fundamental processes underlying MALDI are known.

Sample Preparation System and Method

Now an embodiment of a method of the invention will be described in which a suspension is made from a sample of a colony of microorganisms picked from a culture dish together with an embodiment of a sample preparation system 1000 for performing such a method.

FIG. 1 depicts system 1000 for performing the methods described herein. System 1000 includes a housing 1005 that provides an environment for practicing the methods and for components which perform the described methods. In this regard, the components are distributed within housing 1005 amongst a plurality of stations. From left to right, the housing provides a receiving station 1010, a pick station 1020, a preparation station 1030, and a transfer station 1040. Receiving station 1010 receives one or more culture dishes suspected of carrying microorganisms of interest and automatically feeds such culture dishes to the pick station 1020. Pick station 1020 automatically detects a colony of interest and picks a sample therefrom. Preparation station 1030 automatically prepares samples for testing, such as identification (ID) and antibiotic susceptibility testing (AST). Transfer station 1040 automatically transfers prepared AST samples to AST cartridges (also referred to herein as panels) which are automatically transferred to an AST system.

In the general method, an automated pick tool device 8 is provided to obtain a pick tool 6 and transfer that tool to a stage 2 supporting a culture dish 3 that has been placed on such stage. Prior to pick, a colony of interest 4 is identified on the culture dish 3 and its location thereon determined. The pick tool 6, having been informed of the location through a controller 30, moves the pick tool 6 over the colony of interest 4 and picks the colony. Once picked, the picked sample 19 is transferred into one or more cuvettes or suspension tubes 11. Additionally, an aliquot of suspension liquid 14 is dispensed into the suspension tube 11, which is preferably performed before transfer of the picked colony sample 19 into the tube 11. The pick tool 6' is then placed such that the portion of the pick tool 6' carrying the picked sample 19 is submerged into the suspension liquid 14. The pick tool 6' is oscillated to release the microorganisms. A turbidity meter 20 monitors the turbidity of the suspension and provides such information to a controller 30 which cross-references the measured turbidity with concentration specifications for tests to be performed on aliquots of the suspension, such as ID and AST. Target concentrations for both ID and AST are described herein.

Once the suspension reaches the desired turbidity, an aliquot of the suspension is pipetted from the tube 11, and a plate 42 for performing ID testing is inoculated with the suspension. The pipetting tool 46 then obtains another aliquot of suspension for AST. In some embodiments, the suspension might require further dilution with the suspension liquid prior to pipetting the suspension for AST. Once obtained, the pipetting tool 46 then dispenses the suspension into a vessel 82 for AST testing or other assay such as a molecular diagnostic assay. Such vessel may include reagents utilized for such further testing and may be barcode scanned via a tube gripper robot 50 prior to dispense.

Thereafter, the vessel 82 is transferred to a secondary location by a moving device 80. At this location another pipetting tool 66 pipettes the suspension from vessel 82 and inoculates a testing cartridge 90. This cartridge 90 may be moved prior to inoculation by a cartridge transfer robot 70 to a holding structure of a cartridge filling unit 78. The cartridge filling unit 78 may be actuatable to rotate the cartridge 90 to an optimal angle for inoculation. A decapper robot (not shown) may remove a cap from the cartridge 90 as necessary for inoculation via pipettor 60. After the cartridge 90 is inoculated, it may be transferred by a transfer instrument 2000 to a testing instrument 2050 (see FIG. 20). Once testing is performed, the system may then output a final specimen report indicating a quantification of specimen growth and results of ID and AST.

The method is now described more specifically with regard to system 1000 and components thereof. FIG. 2 schematically shows stations 1020, 1030, and 1040 disposed within housing 1005 of system 1000.

Pick station 1020 comprises a stage 2 for a culture dish 3 comprising a microorganism 4 on a nutritional layer 5, such as a layer of agar gel. Culture dish 3 may be positioned on stage 2 via a moving arm (not shown) that transfers the dish 3 from receiving station 1010. Receiving station 1010 may automatically receive a plurality of culture dishes from other upstream laboratory equipment and arrange them in a stacked arrangement prior to feeding dish 3 to station 1020.

Once dish 3 is received at pick station 1020, colony identification and colony pick is performed. Station 1020 includes a positioning device 8 that comprises a pick tool holder 9 for releasably holding a pick tool, such as a disposable pipette tip. As shown, pick tool holder 9 holds a first pick tool 6. The positioning device 8 is arranged for positioning the first pick tool 6 in a starting position (shown in solid lines in FIG. 2) above the culture dish 3 and is arranged for automatically lowering and raising the first pick tool 6 towards and away from the culture dish 3, such that the first pick tool 6 can be positioned in a position (indicated with broken lines) in which it contacts the microorganism 4 and picks up a sample 19 of the microorganism 4. After the first pick tool 6 has picked up a sample 19 (first pick tool with retained sample 19 indicated in FIG. 2 as 6'), the positioning device 8 raises and positions the first pick tool 6' in a transfer position "A" located over a suspension tube 11. Positioning device 8 preferably raises pick tool 6' vertically to the starting position prior to moving horizontally along a transfer track 18 to the transfer location A. This may help prevent contamination by mucoid strings that may form during sample pick. However, in other embodiments positioning device 8 may move simultaneously both vertically and horizontally (as indicated by arrows in FIG. 2) toward the transfer position A.

Figure 15:
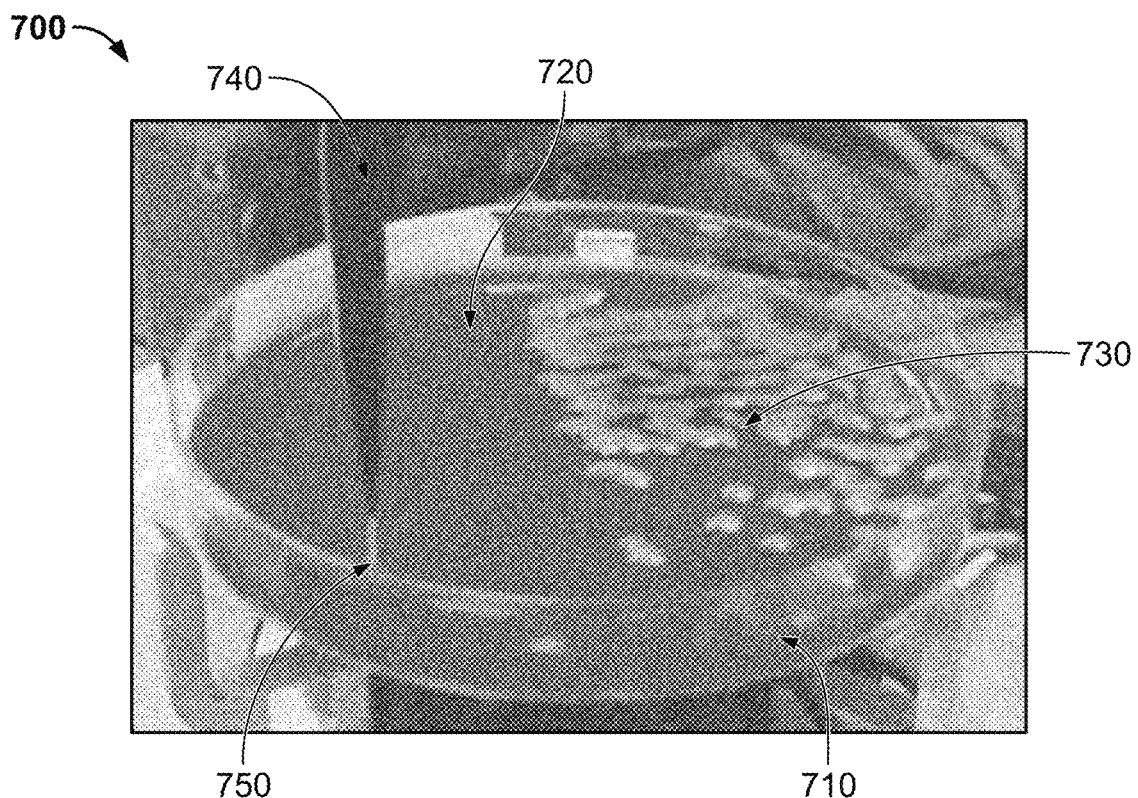
FIG. 15 illustrates a pipette removing a mucoid sample from a target plate wherein a string begins to form.
Figure 16:
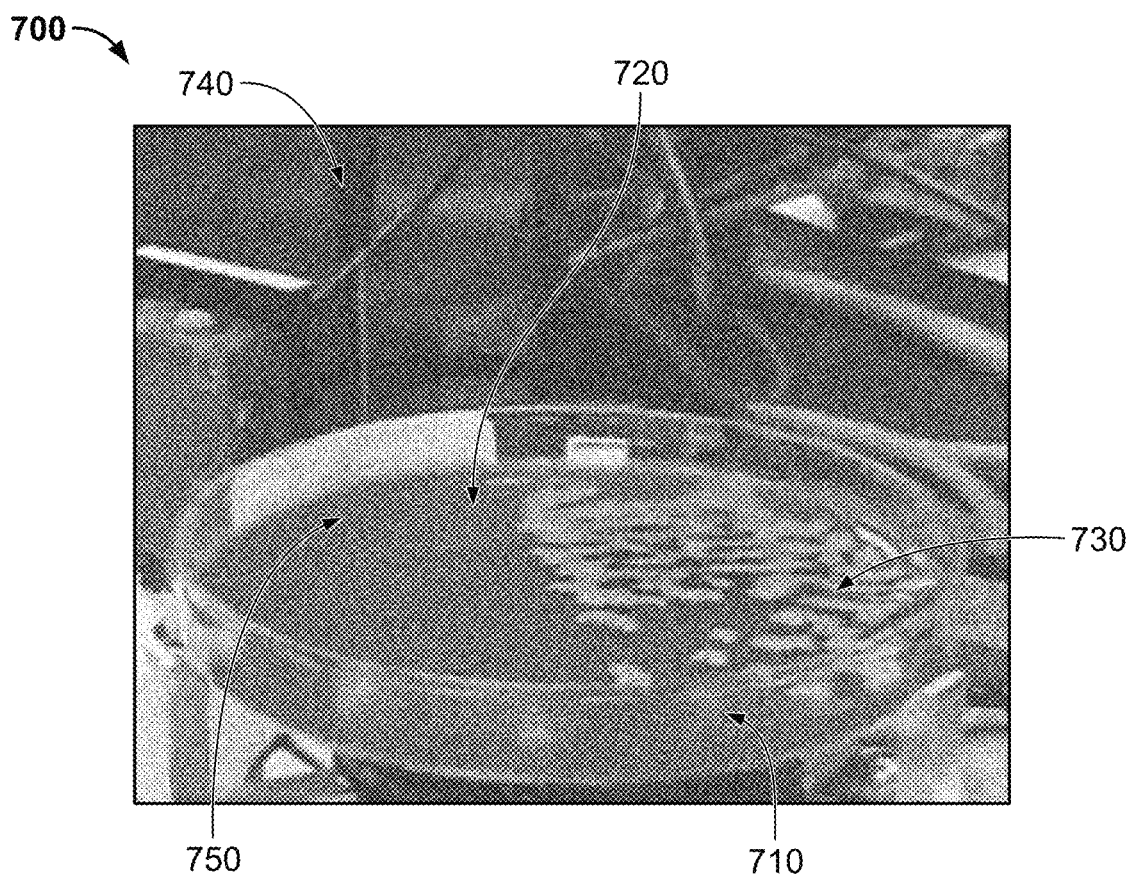
FIG. 16 illustrates the target plate of FIG. 15 wherein the pipette is drawn further away from an agar surface of the plate further extending the string.

In picking colonies for further testing a property of some colonies is the sticky or slimy characteristics noted above. This is referred to as a mucoid consistency that makes removing the colony from the agar surface difficult. As noted above, after the colony is touched by the picking device, a mucoid string will often form between the picking device and the colony on the agar surface (FIGS. 15 and 16). This string can be difficult to break in a controlled manner and poses the problems noted above with regard to potential contamination of other samples and surfaces within the instrument.

When manually picking colonies, the user will see the string formation and can make any number of manual motions to eliminate the string. This includes rotating the picking device and/or rubbing the device on a clean portion of the plate. Since the string can be visually observed the user will see when the string is broken and can proceed with testing. All these measures can be taken with little risk of cross-contamination In one embodiment of an automated process for addressing the presence of a mucoid string, the string is detected optically (e.g. a camera can be used to monitor and detect such strings) or by monitoring changes in an electrical field. The string is conductive relative to the surrounding air. Once the string is detected the skilled person will understand that any number of mechanical devices can be used to break the string. Referring to FIG. 15, there is illustrated a culture plate 710 disposed in an automated system 700. The culture plate 710 has agar 720 disposed thereon on which many different colonies 730 have formed. A pipette tip 740 is lowered into contact with one colony and, as it is withdrawn, a string 750 forms. Referring to FIG. 16, as the pipette tip 740 continues to be drawn up from the surface of the agar 720, the string 750 lengthens. Moving the pipette tip at this point would cause the string to be moved to another location in the system 700. Such can cause cross contamination by the string at other locations in the system 700.

In one embodiment the presence of a string is detected by monitoring the capacitance of the pipette tip as the colony is picked and the pipette is withdrawn from the plate surface to transfer the picked sample into suspension. A string will cause a difference in the charge of capacitance as the pick tool is retracted from the sample.

Figure 17A:
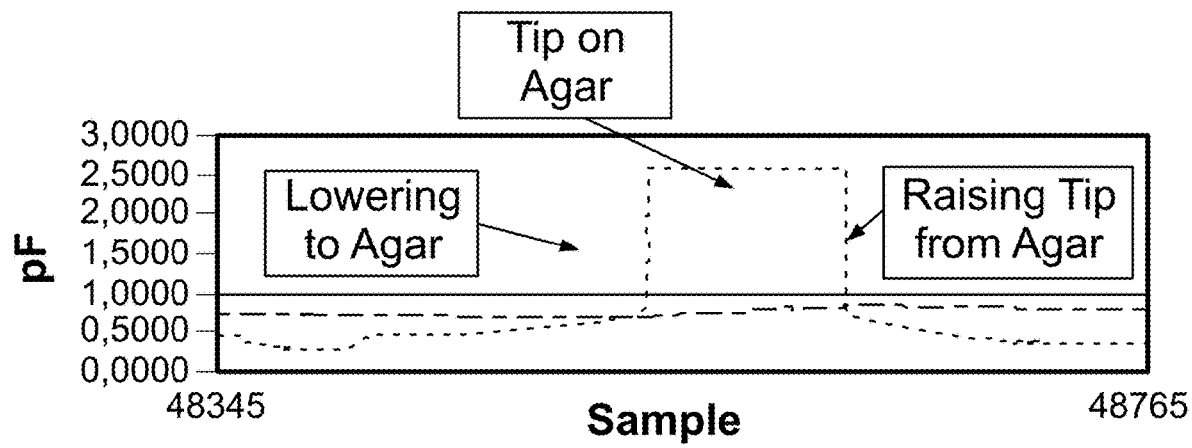
FIG. 17A is a time graph illustrating a change in capacitance over time when a pipette picks a sample but no string is formed.
Figure 17B:
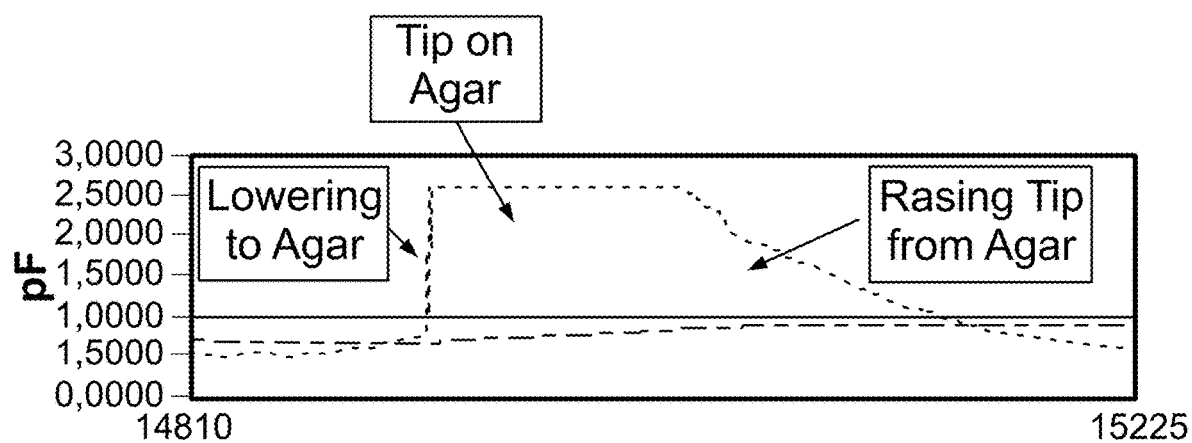
FIG. 17B is a time graph illustrating a change in capacitance over time when a pipette picks a sample and a string is formed.

Capacitance level sensors can sense a wide variety of solids, aqueous and organic liquids. Capacitance detection relies on a radio frequency signal applied to the capacitance circuit. By monitoring the capacitance ($pF$=picofarads) the formation of a mucoid string can be detected. FIG. 17A is a plot of capacitance as the pick tool comes down and touches the surface of the agar. The capacitance quickly drops as the pick tool is raised up and away from the agar surface. FIG. 17B illustrates the change in capacitive signal when a mucoid string is formed as the pick tool moves away from the surface. The capacitance slowly decays as the string gets thinner and thinner and eventually breaks.

Conductive level sensors use a low voltage level between two sensors. Since a mucoid string is conductive, the conductivity will remain high as long as the agar surface is connected to the pick tool by the mucoid string.

The string may also be detected optically. The optical signal across the plate is diffracted by the string that forms between the plate and the pipette. This interruption in signal can be detected by the software and thereby indicate the presence of a string.

Any number of mechanical devices can be used to remove the string. Preferred solutions are cost effective and do not create aerosols or contaminate other plates in the system. The mucoid coating on some bacteria make picking difficult in manual and automated systems. The mucoid biofilm protects the organism but makes working with them difficult. For such examples, additional automated steps and features are provided after the pick of a mucoid sample to eliminate the string and prevent contamination of the system.

In one embodiment a resistively heated hot wire or blade is provided to cut through the mucoid string. The wire or blade is heated to a temperature that is sufficient to sterilize the cutting device so that it could be reused continuously. The skilled person can select a suitable temperature that will decontaminate the wire or blade by killing the microorganisms, but not so hot as to induce rapid vaporization of the picked sample that can result in aerosol release of the organism.

Very cold temperature can also be used to break the string. A small spray of liquid nitrogen to the pipette tip once a string is sensed will harden the string, causing it to break. In an alternative embodiment, a cutting probe that is chilled to freezing could be used to slice through the mucoid string and allow a clean break.

In another embodiment, a rotating disposable rod is used to break the string. When a string is sensed the cutting rod is brought into contact therewith. In alternative embodiments, the cutting rod can spin to wrap the mucoid string around the rod in order to ensure the string is broken.

In another embodiment, a sonication device is provided that breaks the string when the pipette tip travels away from the agar plate forming a string. For example, an ultrasonic horn is connected to the pipette tip adapter. Short pulses at high frequency cause the mucoid strand to shear easily when the pick device is pulled away from the agar surface.

In another embodiment, the string is allowed to dry thereby becoming brittle and breaking. Drying time is reduced by blowing air onto the string by a small nozzle positioned beside the plate. Drying time is controlled so as not to significantly increase the time for any one pick.

In another embodiment, a strong current is passed through the string. The natural resistance of the thin mucoid string will result in the greatest resistance in the thinnest (least conducting) part of the string. This increased resistance will cause the string to break apart. The current is selected so that it is strong enough to break the string, but not so strong to induce rapid vaporization that can result in aerosol release of the organism.

After the string is detected, the tip is advanced across the agar surface (3-6 mm above surface). As the string falls on the agar and the tip continues to move, the string will be stretched to the point of breaking. However, since the string will be broken over the agar, no risk of cross contamination is presented. In alternative embodiments, a rapid zig-zag pattern is used to cause the string to break as the tip changes direction over the agar.

In alternate embodiments, the tip is punched into the agar in the plate where there is no growth. This would wipe the tip clean and remove the string. In another embodiment, the pipette tip is moved across the agar surface to the edge of the plate. The string can be effectively wiped off on the edge of the plate and the string eliminated.

In another embodiment, a small vacuum device near the tip is used when a mucoid string is detected. The vacuum would use a HEPA filter system to vacuum in the string and eliminate environmental contamination.

In alternate embodiments, the pipette is treated or coated with a mucolytic agent that can break down the high-molecular weight glycoproteins found in the mucoid string. One example of such an agent is n-acetyl-1-cysteine.

In another embodiment, a low power laser is positioned off to the side of the plate. When the pipettor leaves the plate area the pipette tip is moved just above the laser beam. If a string is present the mucoid string would then move through the beam. The mucoid string would be heated to the point that the string will break.

In another embodiment, when a string is detected, the tip can be rotated 360 degrees. The rotation cuts off the mucoid string. In another embodiment, the pipette tip moves up and down to touch the agar surface at the same location as where the pick occurred, thereby breaking the string. With each touch down, the pipette tip aspirates some volume. This disconnects the mucoid string and actually draws most or some of the string into the pipette tip.

Pick station 1020 further comprises a suspension tube holder 10 for holding the suspension tube 11 which can contain a suspension medium 14. In the present embodiment the suspension tube holder 10 is a rotatable suspension tube holder for rotating the suspension tube 11 around a vertical axis D. However, in some embodiments, tuber holder 10 may be stationary. Suspension medium 14, as shown, is dispensed from an automatic suspension medium dispenser 12, which has a dispensing nozzle 13 for automatically dispensing a suspension medium 14 in the suspension tube 11 held in the suspension tube holder 10. However, in some embodiments an automated pipettor, such as pipettor 40, may separately dispense suspension medium 14 into tube 11.

Positioning device 8 also includes a transferring device 15 incorporated therein for assistance in automatic transfer of sample 19 to the suspension medium 14. The transferring device 15 is connected to pick tool holder 9 and is configured to oscillate pick tool 6' in a linear vertical movement for a period of time which is sufficient for the sample 19 to be released from the pick tool 6'. In the method, once the suspension tube 11 is inoculated with suspension medium 14 and pick tool 6' is positioned in a starting position at transfer location A above tube 11, positioning device 8 lowers pick tool 6' into the suspension medium 14. With sample 19 submerged, as schematically depicted in FIG. 2, the transferring device 15 is activated to oscillate pick tool 6' so as to release sample 19 into suspension medium 14. Thereafter the positioning device 8 positions the pick tool 6 in a waiting position above the suspension tube 11, which may be identical to the starting position. In other embodiments the waiting position and the starting position may be different from each other.

System 1000 also includes a turbidity meter 20 for performing measurements of the turbidity of the suspension medium 14 contained in the suspension tube 11 held in the suspension tube holder 10. As generally known in the art, a turbidity meter can provide measurement values which are a measure of the concentration of material, in the present case the concentration of a microorganism suspended in the suspension medium. As shown in FIG. 2, the turbidity meter 20 comprises a laser 21 which transmits laser light towards and through the suspension medium 14 and a sensor 22 which detects the amount of laser light transmitted through the suspension medium 14. Preferably, a sensor (not indicated in the figure) may be arranged perpendicular to the path of the laser light to detect the amount of laser light which has been scattered by the suspension.

The operation of system 1000 is controlled by a controller 30. Controller 30, as shown schematically in FIG. 3, includes a processor 32 and a memory 34. Controller 30 is communicatively connected to the positioning device 8, the transferring device 15, the automatic suspension medium dispenser 12, and the turbidity meter 20 for automatically controlling the movement of the positioning device 8, the movement of the transferring device 15, the operation of the automatic suspension medium dispenser 12 and the operation of the turbidity meter 20, respectively. In addition the controller 30 may be directly communicatively connected to other parts of the apparatus such as for example the pick tool holder 9, the laser 21 and the sensor 22.

Figure 2:
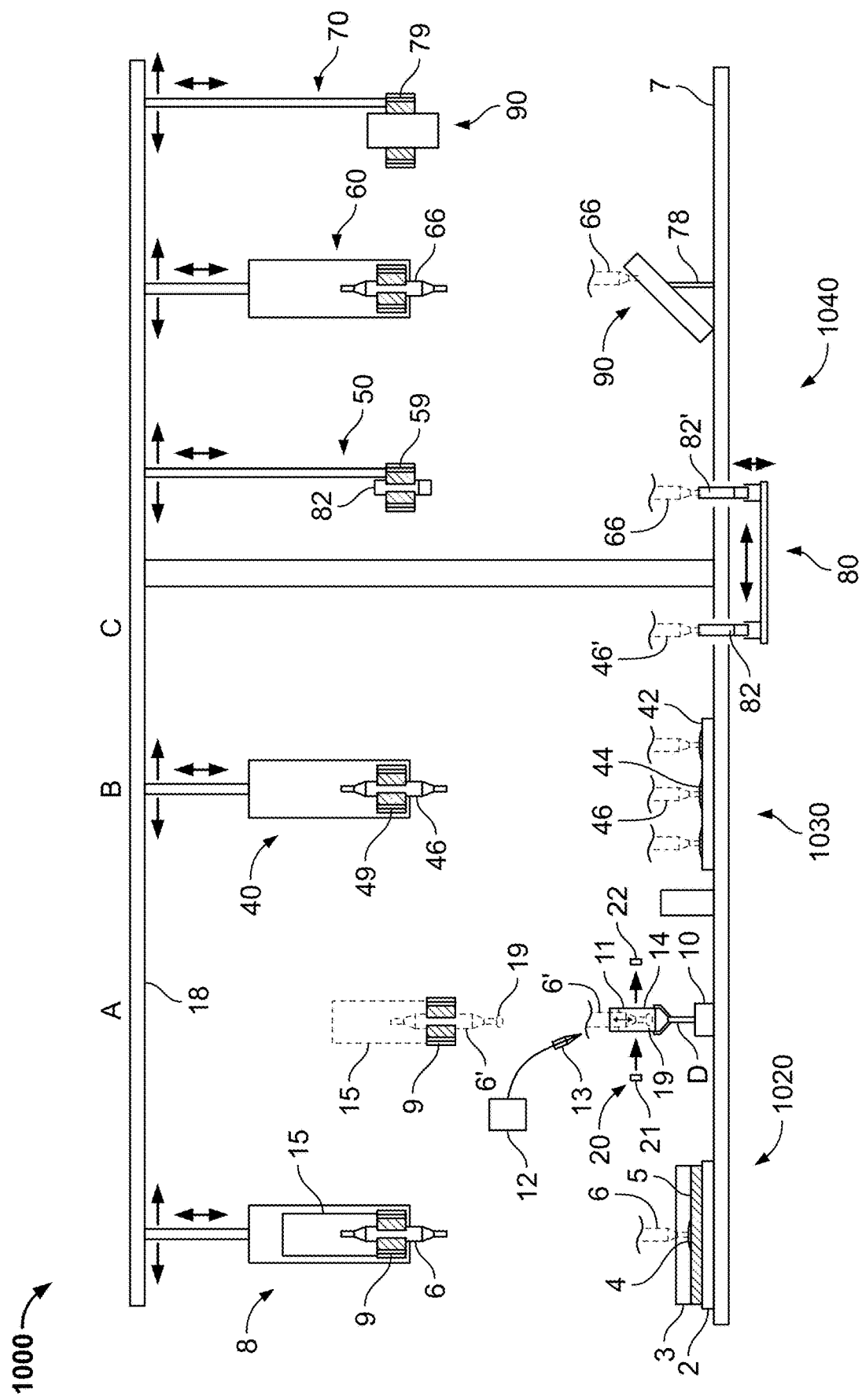
FIG. 2 is a schematic view of a component layout within the system housing of FIG. 1 according to an embodiment of the disclosure.
Figure 3:
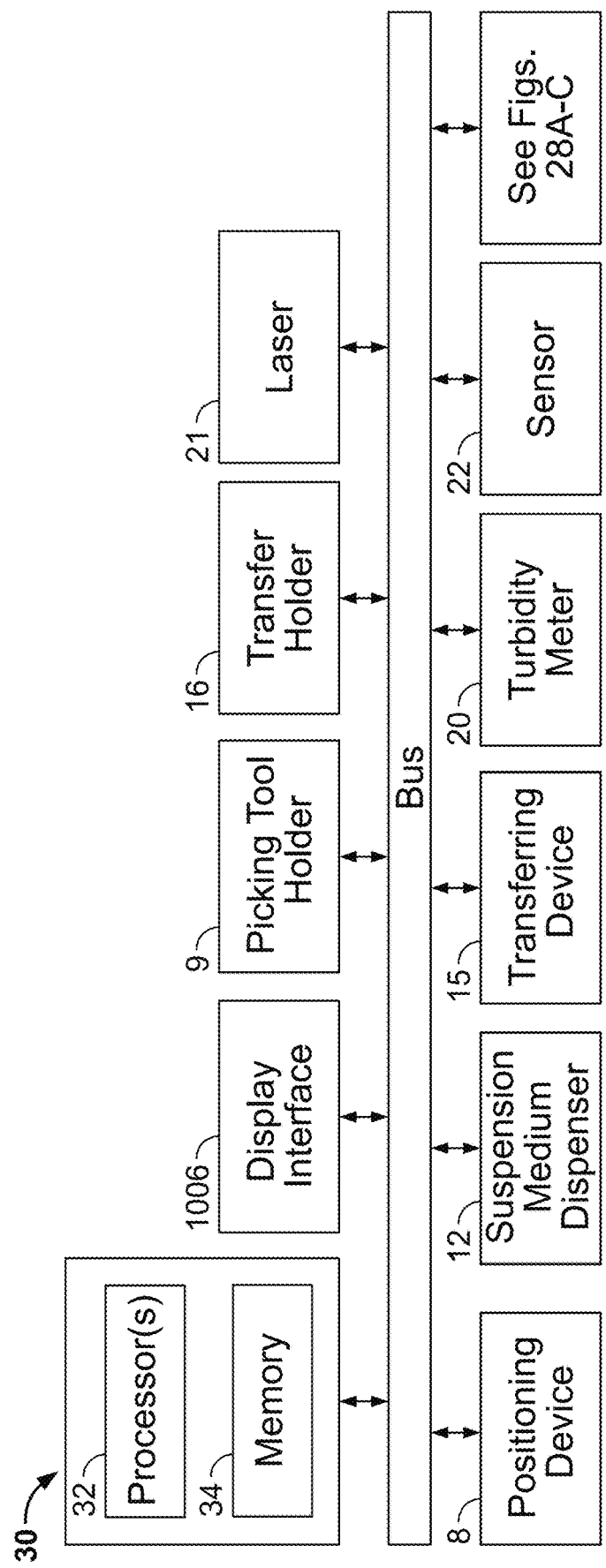
FIG. 3 is a block diagram of an architecture of the system of FIG. 1 according to an embodiment of the present disclosure including exemplary components suitable for implementing the methodologies described herein.

In the embodiment depicted in FIGS. 2 and 3, the controller 30 is arranged for controlling the turbidity meter 20 such that the turbidity measurement of the suspension medium 14 is started before the pick tool 6' is submerged in the suspension medium 14. In addition, the controller 30 controls the rotatable suspension tube holder 10 for starting the rotation of the suspension tube 11 held in the holder 10 before the pick tool 6' is submerged in the suspension medium 14, and for maintaining the rotation of the suspension tube 11 during the measurement of the turbidity of the suspension medium 14. The controller 30 further controls the turbidity meter 20 such that the measurement of the turbidity is performed during the total period of time during which the pick tool 6' is oscillated. In this manner the turbidity meter 20 provides an on-line measurement value to the controller 30 which value is indicative of the measured turbidity, and thus the concentration of the microorganism, during the period of time during which the pick tool 6' is oscillated.

As mentioned above, controller 30 comprises a memory 34, which stores a first and a second threshold value. The first threshold value is equal to or greater than the second threshold value. If the turbidity measurement value provided by the turbidity meter is equal to or between the first and second threshold value, the concentration/amount of microorganism in the suspension medium is sufficient to allow the suspension tube 11 with the suspension 14 to be further processed. In such a case where the measured turbidity is between the first and second threshold values, the controller 30 provides a signal that the suspension within suspension tube 11 can be processed further. In addition, in this situation, the pick tool 6 can be discarded, for example, by moving positioning device over a waste receptacle and activating pick tool holder to release pick tool 6 into the waste receptacle.

In the event the final measurement value of the turbidity meter 20 is above the first threshold value previously stored in memory 34 of the controller 30, then the concentration of the microorganism is determined to be too high to allow the suspension within suspension tube 11 to be processed further. In such situation the controller 30 controls the automatic suspension medium dispenser 12, or some other medium dispenser, to supply an additional amount of suspension medium 14 into the suspension tube 11. This additional amount of suspension medium 14 is based on the initial amount of suspension medium, the final measurement value and the value of the first and/or second threshold value such that the addition of the additional amount of suspension medium to the suspension medium 14 already present in the suspension tube 11 will lead to a concentration of microorganism in the suspension medium 14 of tube 11 which satisfies the requirement for further processing, as can be confirmed by an additional or further measurement of the turbidity by the turbidity meter 20.

In the event the final measurement value of the turbidity meter 20 is below the second threshold value, meaning that the concentration of microorganism in the suspension medium 14 is too low, the controller 30 controls positioning device 8 such that an additional sample 19 of microorganism 4 is picked up by the first pick tool 6 in order to further concentrate the suspension medium 14. Alternatively first pick tool 6 may be discarded and a second pick tool can be used for picking up such additional sample. In this regard, when it is determined that the final measurement value is below threshold, controller controls the first pick tool 6 in the pick tool holder 9 of the positioning device 8 so that it is lowered from the starting position above the culture dish 3 towards the culture dish and into contact with the microorganism 4 to pick up an additional sample 19 of the microorganism 4. Thereafter, the first pick tool 6' is automatically raised with the additional sample 19 of the microorganism 4 away from the culture dish to the starting position at transfer location A above suspension tube 11. Then, pick tool 6' with the additional sample of the microorganism is lowered into the suspension medium 14 and is oscillated by the transferring device 15 in a linear vertical movement for a period of time for releasing the additional sample 19 of the microorganism 4 in the suspension medium 14. Again the turbidity is measured during the oscillation, and the measured value is compared with the first and second threshold value stored in the memory 34 of the controller 30. In this case the controller 30 can be arranged for controlling the movement of the positioning device 8 such that the first pick tool 6, once the additional sample is at least partially removed therefrom, is raised to the waiting position if, during oscillation, the on-line measurement value of the turbidity acquired by the turbidity meter 20 is equal to or lower than the first threshold value and equal to or greater than the second threshold value.

Although concentration of the microorganism within suspension medium 14 can be increased by multiple subsequent colony picks as just described in the event the measured turbidity is below the threshold level, other procedures can be performed instead to account for a measured concentration determined to be too low. In this regard, as is described in more detail below, multiple dispenses of the low concentration suspension can be deposited on the same spot of a MALDI plate. This has the effect of concentrating the microorganism 4 on the MALDI plate, rather than in the suspension medium 14.

Suspension tubes 11, or alternately, vials or cuvettes which are particularly useful in the inventive apparatus have a cross-section with a target maximum dimension of about 2 to about 12 mm, preferably about 3 mm. In these relatively small suspension tubes the controller 30 can control the automatic suspension medium dispenser 12, or other medium dispenser, such that the supplied initial amount of suspension medium is about 0.1-5 ml, preferably less than about 1 ml.

The oscillation of the transferring device 15 is controlled by the controller 30 such that the pick tool 6' oscillates at a frequency between about 5 Hz to about 250 Hz, preferably about 100 Hz, with an amplitude of about 0.5 mm to about 4 mm, preferably about 2 mm to about 3 mm. The controller 30 is furthermore arranged for controlling the oscillation of the transferring device 15 such that the period of time during which the pick tool 6' oscillates is about 3 seconds to about 120 seconds, preferably about 30 to about 60 seconds.

Nephelometers of Automated System and Method

Various nephelometer embodiments are now described. It should be understood that any one of such now described nephelometer can constitute nephelometer 20 previously described. In one embodiment, the nephelometer used in the automated system 1000 may be the nephelometer described in U.S. Provisional Application 62/056,911 which is commonly assigned and incorporated by reference herein. In this embodiment the suspension is not oscillated as the turbidity is measured.

Figure 4A:
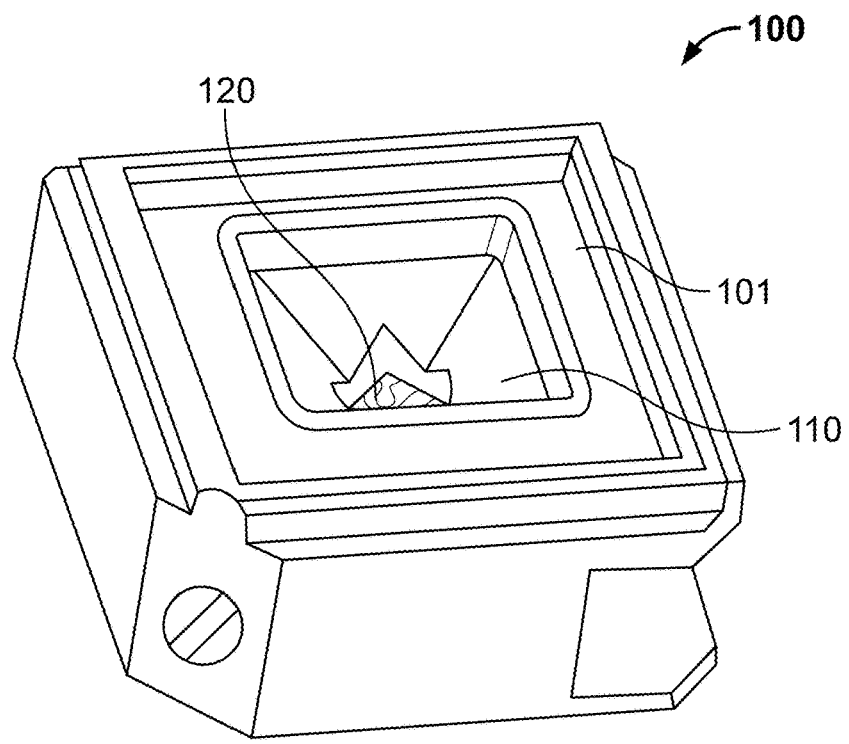
FIG. 4A is a perspective view of an embodiment of a low volume single cuvette nephelometer.
Figure 4B:
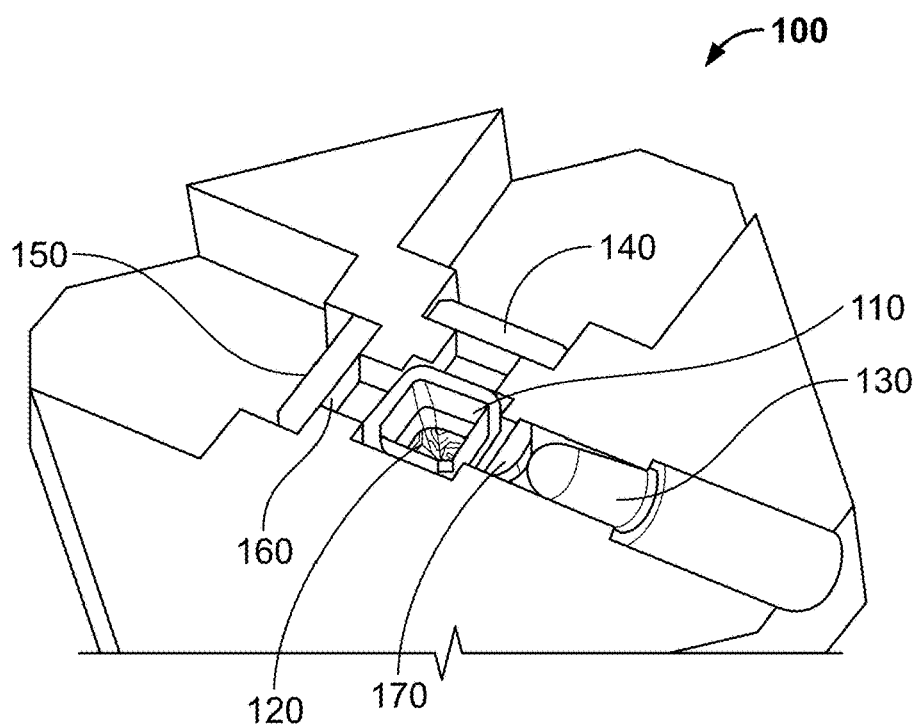
FIG. 4B is a sectional top view of the low volume single cuvette nephelometer of FIG. 4A taken along a horizontal plane extending therethrough.

Another nephelometer embodiment 100 is depicted in FIGS. 4A and 4B. Nephelometer 100 is low volume nephelometer designed to house a single suspension tube illustrated as a cuvette 110 that has a suspension fluid 120 placed inside a nephelometer base 101 as shown in FIG. 4A. Nephelometer 100 also includes a light source 130, a focusing lens 170, a side scatter detector 140, a transmitted light detector 150, and a light attenuation filter 160 (best shown in FIG. 4B). The cuvette 110 with a sample 120 is positioned at the center of the nephelometer 100 and inside the nephelometer base 100. The light source 130, the scatter detector 140 and the transmitted light detector 150 are positioned at 90 degree angles relative to one another around the cuvette 110. The scatter detector 140 is positioned within close proximity to the cuvette 110 containing the sample suspension 120 and parallel to the incident light source 130. This minimizes the effects of diffraction, refraction and reflection on the scattered light. The transmitted light detector 150 is positioned at 180 degrees or opposite from the light source 130. The detector 150 also may be oriented either perpendicular to the incident light beam or at a different angle to reduce reflectance effects from its surfaces. The light attenuation filter 160 is positioned between the cuvette 110 and the transmitted light detector 150. In this configuration, sample suspensions are individually processed inside the vessel 110 and nephelometer 100 detects scattered and/or transmitted light that is passed through the tested sample 120 at an angle.

Figure 5A:
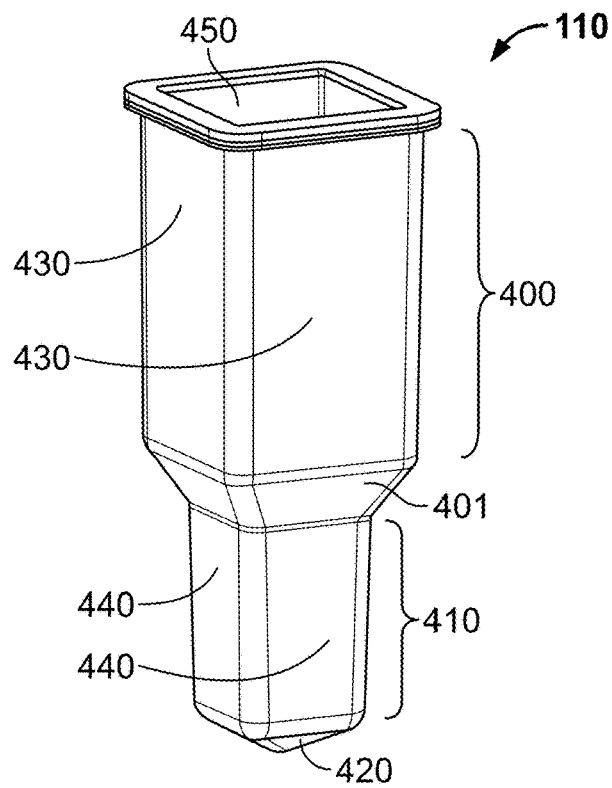
FIG. 5A is a perspective view of a single cuvette according to an embodiment of the present disclosure for use with the low volume single cuvette nephelometer of FIG. 4A.
Figure 5B:
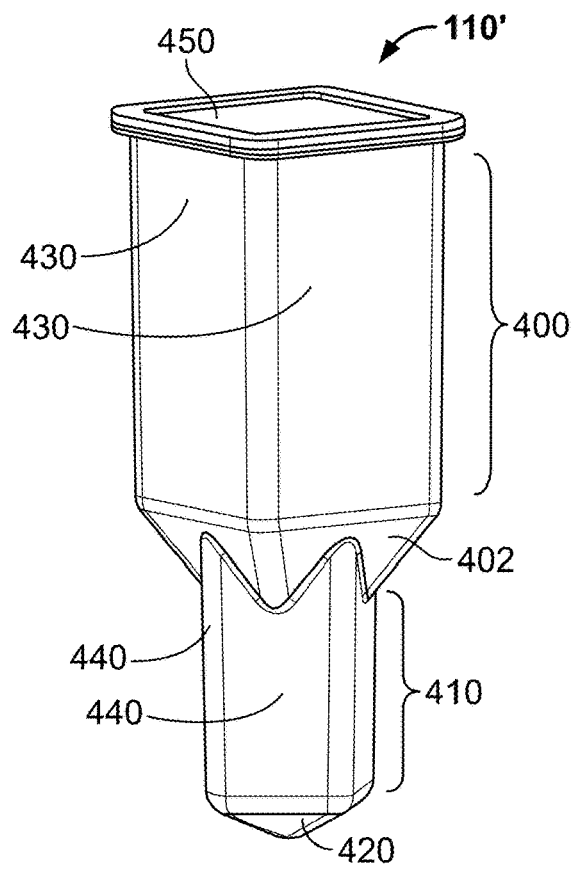
FIG. 5B is a perspective view a single cuvette according to another embodiment of the present disclosure for use with the single cuvette nephelometer of FIG. 4A.

The use of low volume vessels/cuvettes (or micro-cuvettes) that are designed to process relatively small quantities of biological and fluid suspensions for use in conjunction with a low volume nephelometer, such as nephelometer 100, is contemplated. FIGS. 5A and 5B depict alternative embodiments of such low volume cuvettes. Cuvettes 110, 110' are molded from optically clear plastic with minimally tapered sides 430, 440 that have an optically smooth polish to be conveniently oriented within nephelometer 100. The cuvettes 110, 110' may be configured as individual units for single use applications. However, in some embodiments, as is described further below, where a series of cuvettes are used to prepare suspensions, the cuvettes 110, 110' can be configured for use with linear array strips for such applications. Alternatively, the cuvettes 110, 110' may be configured for use with a matrix array designed for processing multiple samples simultaneously. In the matrix embodiment, multiple series of suspensions are prepared in parallel.

As shown, the cuvettes 110, 110' have a lower portion 410 that has a relatively small volume as compared to an upper portion 400. The suspension is initially prepared in the small volume portion 410. The suspension is therefore first disposed inside the lower portion 410 of the cuvettes 110, 110'. A biological sample suspected of containing a target microorganism is added to, and mixed with, the fluid suspension to provide a test sample suspension 120. The turbidity of the suspension in the lower portion 410 is measured. In this regard, when cuvette 110 or 110' is coupled to nephelometer 100, light generated by light source 130 passes through the sample suspension 120 that is disposed inside the lower portion 410. The nephelometer 100 detects the light scattered by the lower portion 410 via detectors 140 and 150 and measures the turbidity of the sample in the lower portion 410 of the cuvette based on the detected light.

Beneath the lower portion 410 of each of the cuvettes 110, 110' is a "large particulate" collection area 420 which is designed to receive large particles that settle from the sample suspension that would otherwise adversely affect the accuracy of the turbidity measurements made by the nephelometer 100. Low volume samples otherwise have insufficient volume to allow the particulate contaminants to settle from the portion of the suspension interrogated by the nephelometer. For example, a light which passes through a low volume suspension that contains particulate impurities may not differentiate between the sample in suspension and the impurities and can yield inaccurate McFarland values (i.e., values indicative of turbidity) that cause the sample to be processed improperly. For example, an inaccurate McFarland value may inform the wrong dilution. An inaccurate McFarland value may also cause a sample to be processed downstream (either by AST or MALDI for example), when, had the true McFarland value been known, the sample would not have been further processed. That is, the true McFarland value would have informed the operator that the sample was not suited for MALDI or AST. In addition, the presence of impurities in the sample may interfere with the accurate concentration measurements of the sample being tested. As such cuvettes 110, 110' according to the depicted embodiments provide this separate, particulate collection area 420 that is outside of the direct light path that passes through lower portion 410. Particulate contaminants settle into the collection area 420 and do not remain in the tested area of the sample suspension, which occurs in the lower portion 410. The cell length of the lower portion is in the range of about 5.5 mm and is designed to provide sufficient cell length for low volume samples to obtain adequate turbidity measurements. The lower portion is designed to provide sufficient cell length once a test sample suspension is prepared in order for the light to pass through the samples and be captured by the detectors 140 and 150. Preferably, the lower portion 410 is made of a highly polished optical material or a material having near optical clarity and other optically transmissive materials known to one skilled in the art. Such materials allow the light to pass through the walls 440 of the lower portion of the cuvette without interference.

One skilled in the art will appreciate that there are three dimensions of design freedom to configure the small volume portion 410 of the cuvettes 110, 110'. The dimensions of the small volume portion 410 are largely a matter of design choice. In one embodiment, the dimensions of the small volume portion 410 are configured to receive a device (e.g., a pick tool) that will introduce the sample into the lower portion of the cuvette. For example, and not by way of limitation, the lower portion of the cuvette is dimensioned to provide adequate room for a 3 mm diameter pick tool to be submerged and rotated within the lower portion such that it does not touch the sides of the cuvette 110 or 110', creating scratches and surface aberrations that would degrade the optical transparency thereof.

Of course, the dimensions of the lower portion 410 must accommodate optical inspection of the sample. Specifically, the lower portion 410 of the cuvettes 110, 110' is dimensioned to work with the optical source 130 and detectors 140, 150 of the nephelometer 100. The dimensional constraints on cuvette design are therefore a function of the configuration of the nephelometer 100.

Above the lower portion 410 is the upper portion 400 which is used to dilute the sample suspension placed inside the vessel for further processing in downstream applications, such as AST. The upper portion 400 has a larger width and length than the lower portion 410. Preferably, the internal dimensions of the vessel are designed to accommodate automated mixing of the biological sample with a suspension fluid to further dilute the test sample suspension directly inside the vessel when required. In operation, the tiered vessel design of cuvettes 110, 110' allows the turbidity of the sample suspension therein to be measured and, if target turbidity has not been reached, to further dilute the sample and repeat the turbidity measurements. Such a configuration allows dilution of the sample in real time (i.e., as the sample is being optically interrogated). In addition, the tiered vessel design makes it possible to measure the turbidity of low volume sample suspensions (e.g. suspensions with a volume of about 200 μL to about 500 μL) yet have the benefits of a larger volume to accommodate sample dilution.

As depicted, the top tier or upper portion 400 of each of the cuvettes 110, 110' has an approximately square or rectangular perimeter. Basically the geometric configuration of the upper portion 400 is a matter of design choice. The bottom tier or lower portion 410 also has an approximately square perimeter. In this regard cuvettes 110, 110' "telescope" from top to bottom due to the larger cross-sectional dimensions of the upper portion 400 relative to the lower portion 410. Alternative shapes for the cuvettes 110, 110' are also contemplated so long as the walls 440 of the bottom portion 410 are at an angle from one another (e.g., the cuvette is not cylindrical, elliptical etc.). It has been found that positioning the walls 440 of the lower portion 410 (i.e., the portion received by the nephelometer) at an angle from one another (compared to a round-shape tube) allows for less aberration to the optical signal and better mixing of the test sample. This is illustrated in the depicted embodiments 110, 110' in which the lower portion 410 has four sides 440 that are perpendicular to one another, thereby defining a square. In addition, the upper portion 400 also has four sides 430 that are perpendicular to one another, except the dimensions of sides 430 are broader than the sides 440. The smaller, lower portion 410 is configured to be received by the nephelometer base 101 and/or linear cuvette array (described below). The top of each cuvette 110, 110' has an opening 450 for receiving the sample and diluent/suspension medium. The side walls 430 and 440 of the upper and lower portions 400, 410, respectively, are defined by planar surfaces. Without being bound to any particular theory, it is believed that planar surfaces minimize diffraction and refraction of the light that passes through the cuvettes 110, 110'. It addition, the square configuration of the cuvettes/vessels 110, 110' allows for the light paths to pass through and into the sample suspension and the vessel at right angles to the planar surface of such vessel 110, 110'. This configuration also minimizes the potential for diffraction or refraction of the light source 130 as it enters and leaves the cuvettes 110, 110'.

Various configurations of the cuvettes 110, 110' are contemplated. In the embodiment depicted in FIG. 5A, the top portion 400 of the cuvette 110 is tapered to the lower portion 410. The corners of the top portion 400 where sidewalls 430 intersect align with the corners of the lower portion 410 as can be seen by straight edges 401). The tapered edges 401 demark the transition between the wider upper portion 400 and the narrower lower portion 410.

In the other embodiment 110' depicted in FIG. 5B, the corners of the upper portion 400 where sidewalls 430 intersect are offset from the corners of the lower portion 410 where sidewalls 440 intersect. Such offset occurs at the offset edges 402 as illustrated in FIG. 5B. In one particular example, the corners of the lower portion 410 are offset by 45 degrees from the corners of the top portion 400. Advantageously, this configuration allows for the light source 130 and detectors 140, 150 to be arranged on either side of the cuvette 110' when the cuvette 110' is placed inside the nephelometer base 101.

Methods of using the nephelometer 100 and cuvette 110 for measuring turbidity as shown in the flow chart of FIG. 6 are now described. The cuvette 110 is placed inside the nephelometer base 100 either manually or automatically. The initial suspension fluid (free of microorganisms) is placed inside the cuvette 100. The fluid volume is about 200 μL to about 500 μL. Preferably, the initial suspension fluid volume is about 300 μL. Additional fluid can be added to the cuvette 110 if dilution is needed to obtain the specified McFarland values. Next, a biological sample suspected of containing microorganisms is added to the cuvette 110 and mixed with the suspension fluid to yield a test sample suspension 120. Nephelometer 100 measures the initial turbidity of the test sample 120 and the McFarland value is recorded to memory 34. The sample suspension is further diluted by adding additional suspension fluid if the initial turbidity readings are too high. The dilution is automated in one embodiment. The upper portion 400 of cuvette 110 allows the volume of the suspension fluid to exceed the volume of the lower portion 410. The nephelometer 100 measures the turbidity of the diluted suspension. Once the predetermined McFarland value is obtained, the suspension is either processed for downstream testing, stored or discarded. The suspension may be diluted as many times as necessary in order to obtain the desired McFarland values.

A light from source 130 interrogates the suspension 120 (e.g., tested sample) disposed inside the cuvette 110. The light that impinges on a surface (e.g., flat sidewall 440 of the cuvette/vessel 110) is referred to herein as the incident light. The light that is scattered from the particles of the suspension 120 is referred herein as the scattered light. A portion of the incident light is reflected by the cuvette surface. The refracted or transmitted light is the portion of the incident light that is transmitted through the surface (e.g., the flat sidewall 440 of the cuvette/vessel 110).

In operation, the transmitted light is received by the transmitted light detector 150. In the exemplary embodiments, the transmitted light detector 150 is positioned on the incident light path to maximize the detection of the light transmitted through the suspension. In instances where the surface of the detector 150 is highly reflective, the detector 150 may be positioned such that the detector surface is located at a slight angle (not 90 degrees) in relation to the light path axis. Positioning the detector 150 at an angle optimizes detection of the transmitted light without reflecting the light back into the suspension 120 or directing the light to other portions of the nephelometer 100. The intensity of light collected by the detector 150 is proportional to the turbidity of the suspension.

A light attenuation filter 160 is positioned directly in front of the transmitted light detector 150. The filter reduces the intensity of the light incident on the detector 150 by an amount that is proportional to that of the incident beam. In the exemplary embodiments, the filter 160 allows the detector 150 to operate without saturating and provides sufficient detector operational intensity bandwidth to detect slight variations in the intensity of the transmitted light.

The nephelometer 100 also measures the amount of scattered light. The scatter detector 140 is placed with its detecting surface parallel to the incident light path and along one side of the cuvette 110. Portions of the light that are passed through the suspension sample 120 are scattered by the particles in suspension. The side scatter detector 140 collects some of the scattered light. The amount of scattered light that the detector 140 collects provides a signal that is proportional to the amount of particles in the tested suspension 120. One way to measure the turbidity of the suspension 120 is to process the amount of scattered light collected by the scatter detector 140 through various algorithms well known in the art. The data collected from the scatter detector 140 may be combined with the data collected from the transmission detector 150 in various ways. For example, the signals can be physically combined or the detector values mathematically manipulated to combine them in a way to further enhance the accuracy and reliability of the initial signals. The signals or data values can be combined additively, subtractively, differentially, etc. to provide a resultant signal that is representative of the combined signals. Such combination can be performed by processor 32. When signals of detector values are combined in this manner it is possible to enhance the resolution and accuracy of collected data for measuring turbidity. Advantageously, data collected from two separate detectors (scatter and transmittance data) may provide more accurate results for small volume samples. The dual measurement is advantageous in those embodiments where a scatter measurement does not suffice. The measurement of both transmitted and scattered light yields may be more accurate because of the limited length of the light path through the small volume of sample 120.

In the exemplary embodiments, scatter detector 140 and transmittance detector 150 are standard high efficiency photo diode detectors. However, other detectors having similar characteristics may also be used. Suitable detectors include those that operate across the visible light spectrum from ultra-violet (UV) to infra-red (IR). Suitable detectors may be selected based on their linear response curves, size, reproducibility of results, and the ability to operate/detect light paths within low light conditions and detect minute variations in light intensity with measurable resolution. Examples include photo diodes, photo multiplier tubes, avalanche detectors, solar cells, photo resistors, photo sensors, etc. Such detectors are commercially available, well known to one skilled in the art and not described in detail herein.

In the exemplary embodiments, the light source is a high intensity light emitting diode (LED) or diode laser. Preferably, the frequency of the LED light is about 650 nm. Preferably the wavelength of the detector light is within the red color band (i.e. about 620 to 750 nm). However, the skilled person might use interrogating light at different frequencies of visible light. Optionally, a focusing lens 170 (FIG. 4B) is used to focus the light into a narrow beam (e.g., a beam that is about 3 mm in diameter). The focusing lens 170 is positioned in front of the light source 130. The use of a focusing lens 170 concentrates the light from the light source 130 inside the sample area 410 of the vessel/cuvette and minimizes the amount of light that may be scattered from the test area. One skilled in the art is aware that a light which is scattered outside of the test area (i.e., the lower portion 410 of the cuvette 110) renders the scatter unusable for the purposes of measuring sample turbidity due to high background signal. The focused light then passes from the focusing lens 170 (not shown) into the lower portion 410 of the cuvette 110 at an angle perpendicular to the face of the cuvette 110. The perpendicular angle mitigates unwanted diffraction and refraction which occurs when a beam of light passes from one medium (e.g., air) to another medium (e.g., flat surface sides of a cuvette). The path of the focused light beam is maintained as the light transmits through the suspension towards the detectors 140 and 150. In the embodiments where the light source 130 is a diode laser, additional lenses 170 may not be required to focus the light beam. This is due in part to the properties of the laser which provide collimated and focused light to interrogate the suspension. A focus lens 170 is used in the embodiments where the light source 130 is an LED and collimating or focusing of the light as desired or required.

Figure 7A:
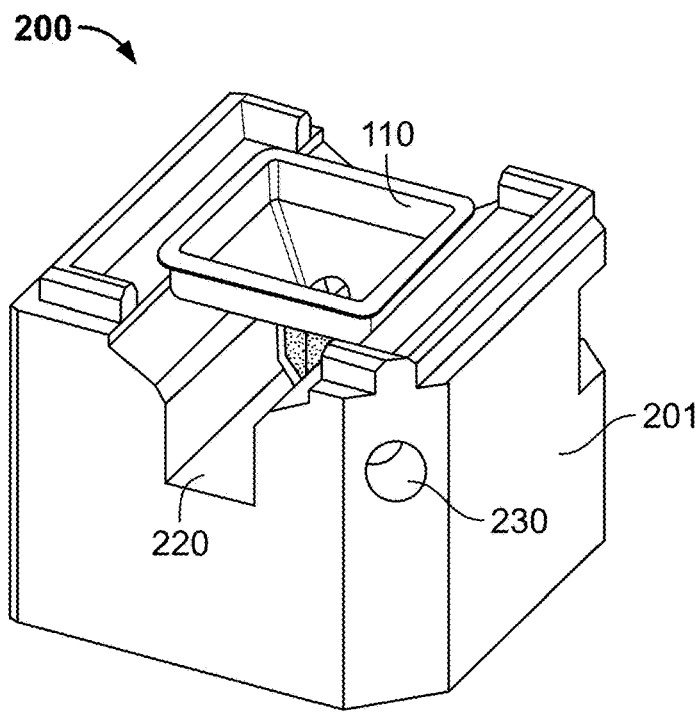
FIG. 7A is a perspective view of a continuous cuvette nephelometer according to an embodiment of the present disclosure.
Figure 7B:
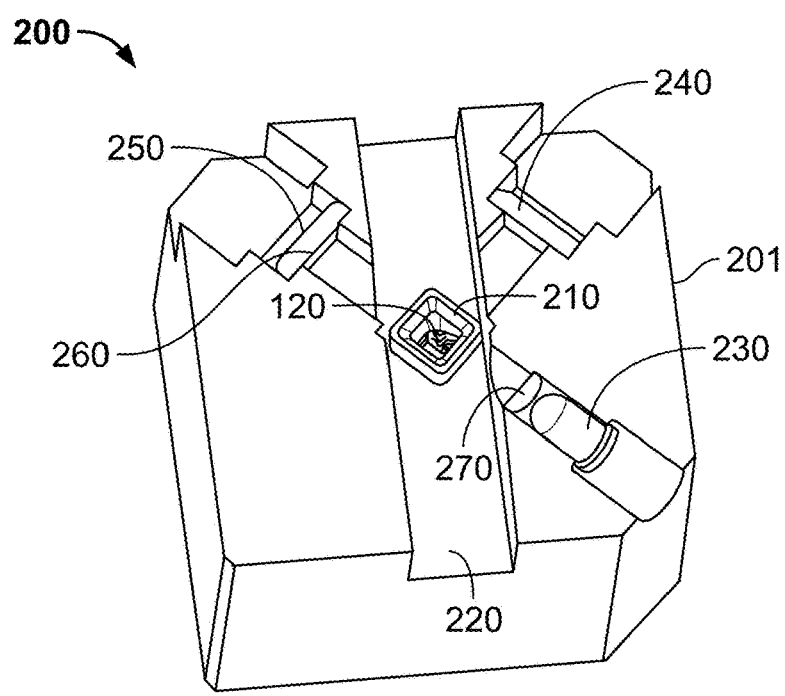
FIG. 7B is a sectional top view of the continuous cuvette nephelometer of FIG. 7A taken along a horizontal plane extending therethrough.

FIGS. 7A and 7B illustrate another nephelometer embodiment 200 where cuvettes are advanced through the nephelometer in series. The system is designed for use with a series of cuvettes (described below) that are advanced through the nephelometer in a continuous fashion. Individual cuvettes 110 may be placed directly inside a nephelometer base 201 by placing the lower portion of the cuvette into the channel 220 as shown in FIG. 7A. Alternatively, individual vessels 110 may be first placed inside the linear vessel array 300, and the linear array 300 (FIG. 8) housing multiple vessels can be placed inside the nephelometer via the pass through channel 220. After the vessels are placed inside the nephelometer base either individually or inside the linear array, the suspension is prepared in the cuvette and the turbidity measured as described above.

Nephelometer 200 also includes a light source 230, a focusing lens 270, a scatter detector 240, a transmitted light detector 250 and a light attenuation filter 260, which are described above in relation to the nephelometer of FIG. 4B. The cuvette 110 with a sample 120 is positioned at the center of the apparatus and inside the nephelometer base 201. The light source 230, the scatter detector 240 and the transmitted light detector 250 are positioned at a 90-degree angle from one another around the cuvette 110 as described above. The side scatter detector surface 240 is positioned parallel to the incident beam from the light source 230. Positioning the scatter detector 240 within close proximity to the tested sample 120 and parallel to the incident light source minimizes the effects of diffraction, refraction and reflection on the scattered light. The transmitted light detector 250 is positioned opposite from the light source 230 and incident light from the light source propagates toward the transmitted light detector. The detector 250 also may be positioned either perpendicular to the incident light path or a few degrees from perpendicular to reduce reflection effects from its surfaces. The light attenuation filter 260 is positioned between the cuvette 110 and the transmitted light detector 250.

Figure 8:
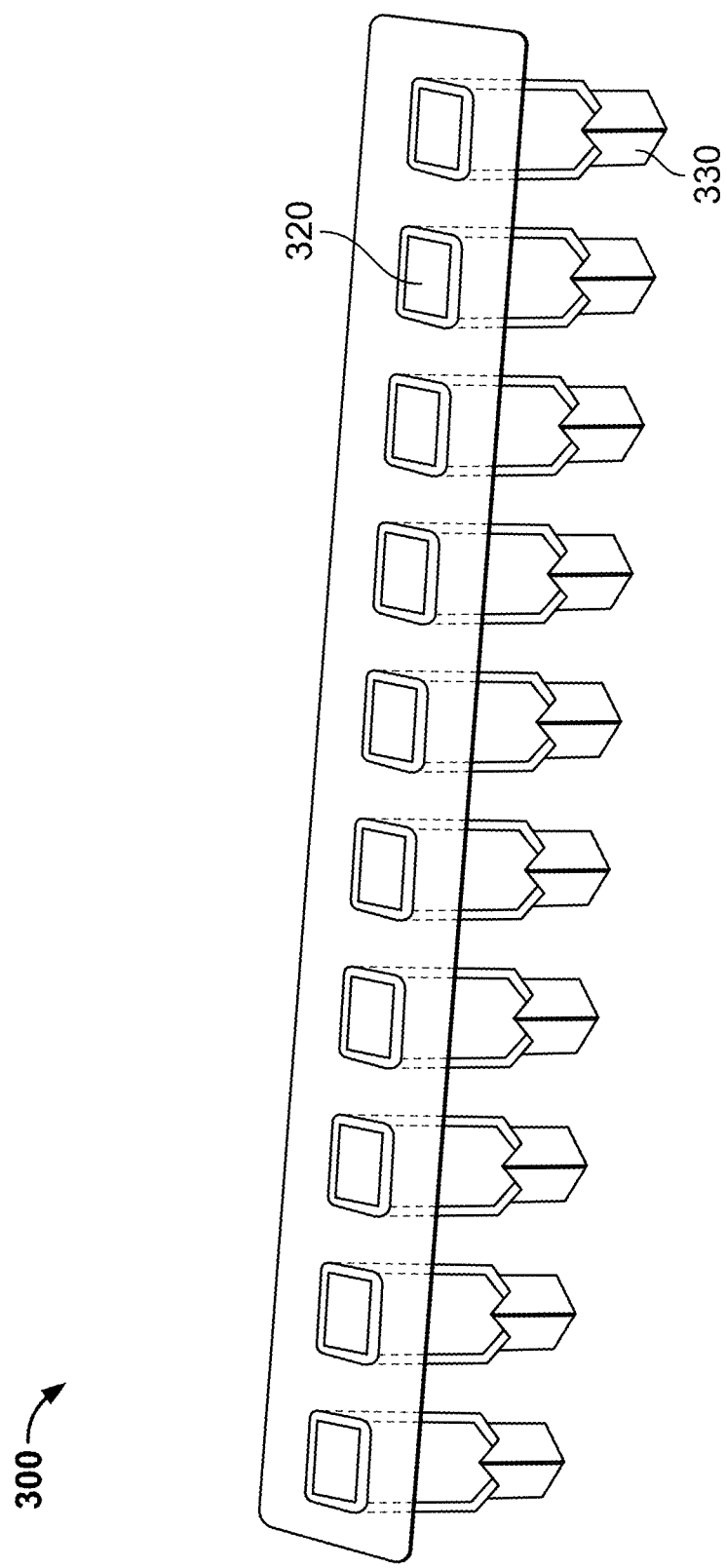
FIG. 8 is a perspective view of a linear low volume multi-cuvette array/strip according to an embodiment of the present disclosure for use with the continuous cuvette nephelometer of FIG. 7A.

FIG. 8 illustrates the series cuvette array/receptacle for use with one embodiment of the apparatus of the present invention, such as nephelometer 200. This embodiment differs from embodiments described above where suspension tubes are rotated to be placed for turbidity measurement. The series cuvette array 300 is a series cuvette strip that is moved along guided channel 220. An LED light source 230 is placed on one side of the guided channel 220 that guides the strip 300. The strip 300 is slideably engaged with the channels 220. The strip 300 can also include stand-offs or other structures 530 (FIG. 9) for convenient stacking, packaging and shipping. The strip 300 is advanced through nephelometer and the cuvette wells 320 are positioned between the light source 230 and detectors 240 and 250 for processing. After processing is complete the linear strip 300 may be indexed and advanced to the next cuvette and processing continued for the subsequent samples using the same nephelometer. The cuvette strip 300 may be stored or discarded based upon individual user's needs. In this embodiment, a single nephelometer is designed to efficiently process multiple samples without the need to remove individual cuvettes and replace them with new cuvettes. The linear cuvette strip 300 may be designed with various cuvette shapes, sizes and configurations. For example, the wells 320 of the strip 300 may be designed to be more or less deep, wider, narrower, longer, shorter etc. depending upon the cuvette design. In addition, the wells may be attached to one another across individual wells or be individually inserted into the wells positioned next to one another. Placement of the multiple cuvettes 110' with edges 402 inside a linear array 300 allows for more efficient transport of the cuvettes 110' through the nephelometer 200 because they can be processed in series and received by the nephelometer and measured without additional manipulation thereof.

Figure 9:
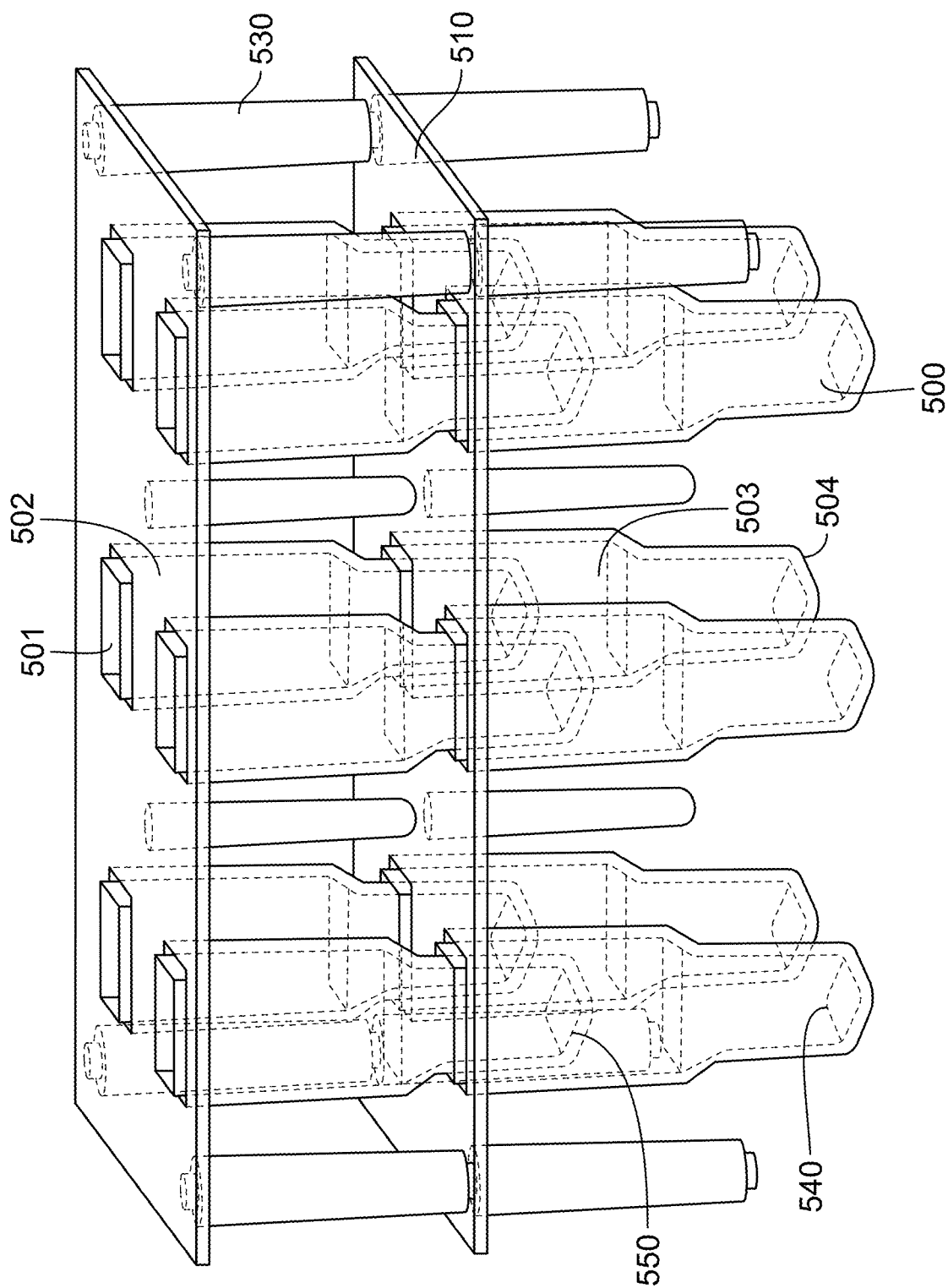
FIG. 9 is a partially transparent, perspective view of stacked cuvettes.

In another one series cuvettes embodiment depicted in FIG. 9, the cuvette strips are stackable and can be separated either into individual cuvettes or a linear strip of cuvettes, depending upon the nephelometer configuration. In the depicted embodiment, cuvettes 500 are carried by a rack 510. Rack 510 has a flat surface from which the cuvettes are suspended. The flat surface is scored (not shown) to allow the cuvettes to be separated into individual cuvettes or strips of cuvettes. The stackable cuvettes also have stand-offs 530 as described above. Note that, to facilitate stacking, the lower portion 540 of the cuvette 500 s received by the wider, upper portion 550.

Figure 10:
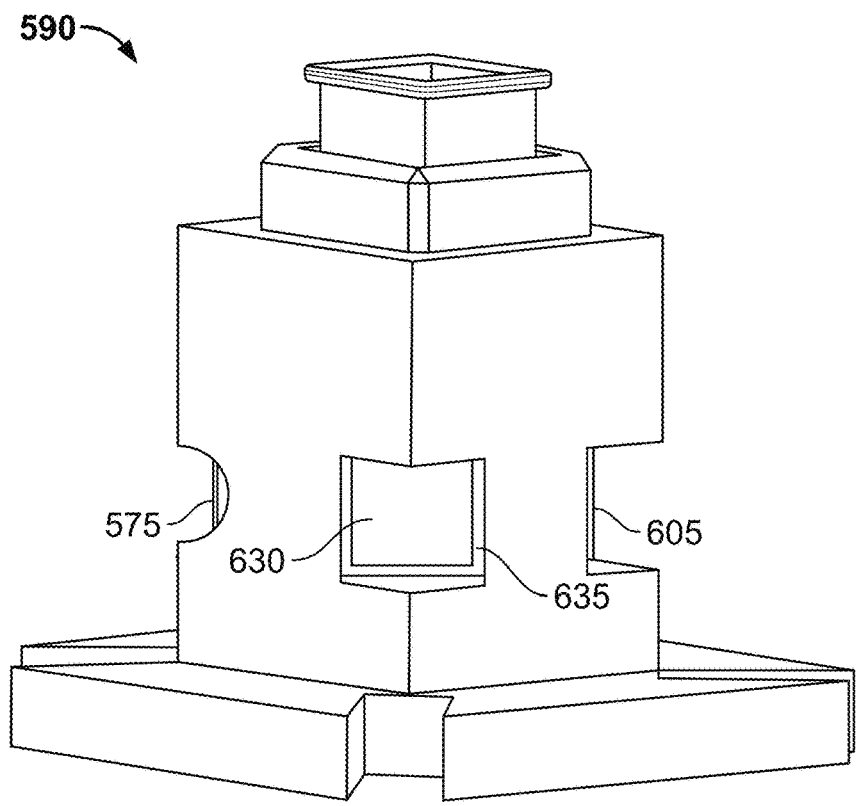
FIG. 10 is a perspective view of a nephelometer according to another embodiment of the present disclosure.

FIG. 10 is perspective view of a nephelometer 590 showing aperture 575 for an optical source 570, aperture 635 for a scattered light sensor and aperture 605 for a transmitted light sensor.

Figure 11:
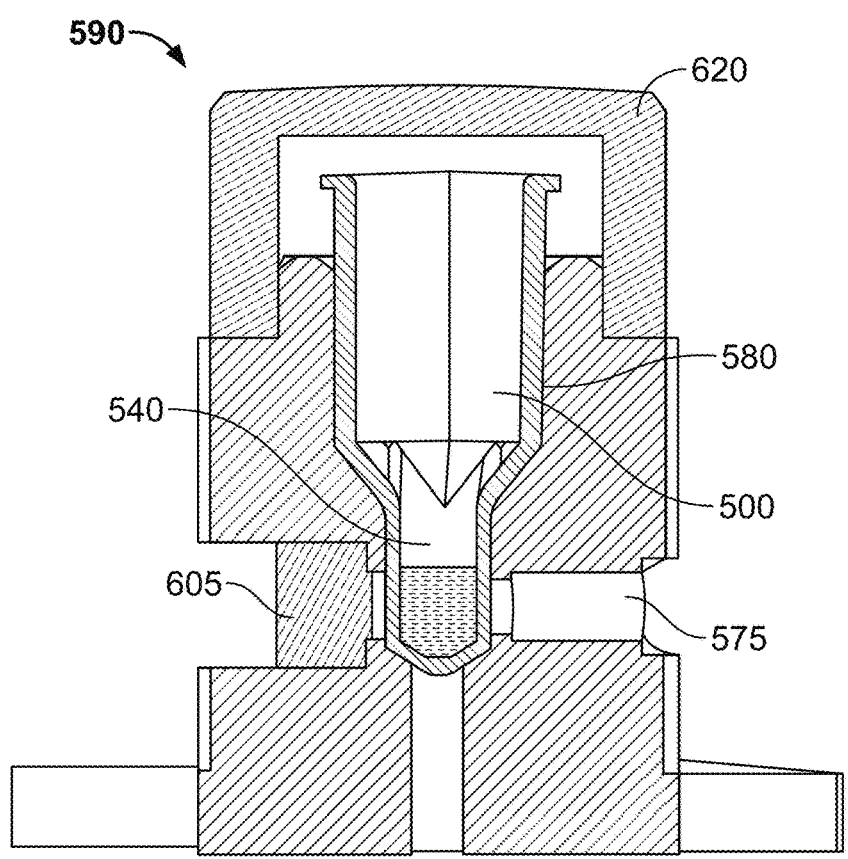
FIG. 11 is a cutaway view of the nephelometer of FIG. 10 illustrating a transmitted light detector pathway thereof.

FIG. 11 is a cutaway of a nephelometer 590 showing the path for the light transmitted through the lower portion 540 of the cuvette 500. The light source (570, FIG. 12) is received by an aperture 575 on one side of cuvette receptacle 580 of the nephelometer 590. The aperture 575 receives the light source. The sensor 600 (FIG. 12) is positioned in an aperture 605 directly opposite the aperture 575, with the lower portion of the cuvette 540 positioned therebetween. The nephelometer has a lid 620.

Figure 12:
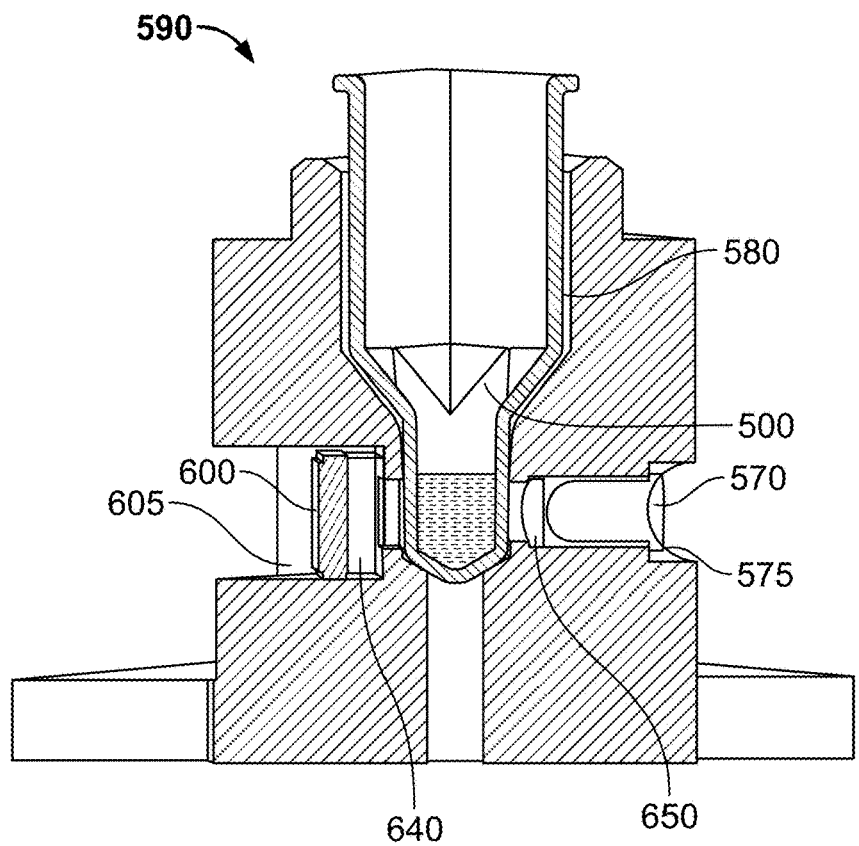
FIG. 12 is a further cutaway view of the nephelometer of FIG. 10 illustrating the transmitted light detector pathway of FIG. 10 while also illustrating an optical source and a transmitted light detector.

FIG. 12 is a cutaway of nephelometer 590 showing the path for the light scattered through the lower portion 540 of the cuvette 500. The light source 570 (FIG. 12) is on one side of cuvette receptacle 580 of the nephelometer 590. The sensor 630 (FIG. 10) is positioned in an aperture 635 orthogonal to the light source 570, with the lower portion of the cuvette 540 positioned therebetween.

Figure 13:
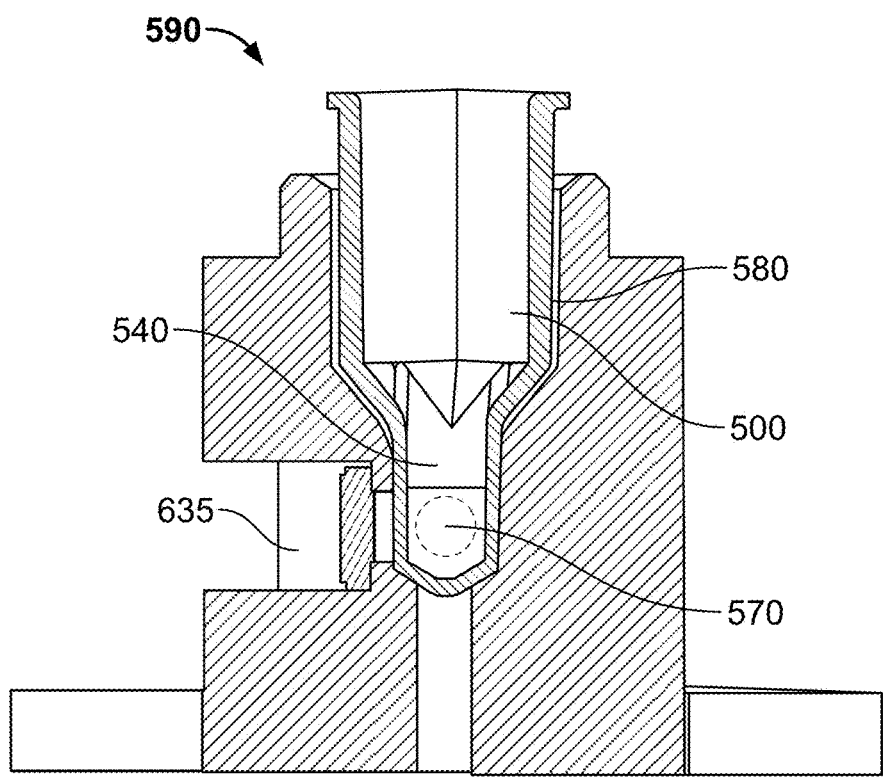
FIG. 13 is another cutaway view of the nephelometer of FIG. 10 illustrating a scattered light detector pathway thereof.

FIG. 13 is a cutaway of nephelometer 590 showing the path for the light transmitted through the lower portion 540 of the cuvette 500. The light source 570 is received by an aperture 575 on one side of cuvette receptacle 580 of the nephelometer 590. Between the sensor 600 and cuvette 500 is a light attenuation filter 640 that is placed in front of the transmittance detector to decrease the light intensity to a usable level so as not to saturate sensor. The aperture 575 receives the light source 570 and the lens 650 for focusing the optical signal. The sensor 600 is positioned in an aperture 605 directly opposite the aperture 575, with the lower portion of the cuvette 540 positioned therebetween.

In one embodiment, the sample is disposed inside a cuvette and individually processed when placed into the nephelometer. After the sample is processed and McFarland values are obtained, the cuvette is removed from the nephelometer and replaced by a new cuvette. In this embodiment, the one or more nephelometers are operated independently. In an alternative embodiment, the nephelometer is configured to deliver a continuous series of cuvettes to the nephelometer for measurement. A linear cuvette channel 220 receives a strip 300 of individual cuvette wells 320 (FIG. 4B). The strip is conveyed through the nephelometer, stopping for each cuvette to be optically interrogated for measurement as described in detail elsewhere herein.

The methods of measuring the turbidity according to the present invention are automated. The data collected from the measurements may be further processed to generate meaningful results. In these embodiments, the signal from the detectors are fed to signal amplifiers. The amplifier output is communicated to an analog to digital converter circuit that outputs a digital representation of the input signal that is then processed using various algorithms to determine if the measured value is at the target value. If the measured value is higher than the target value, then the sample is diluted as described above, and the turbidity re-measured. Such re-measurement can be done manually by an operator or in an automated manner where the cuvette is transferred out of the nephelometer for dilution and transported back to the nephelometer for an additional measurement. The methods for processing the signal into a usable output are developed using varying dilutions of various biological and non-biological sample and associating McFarland values with the suspension concentrations. These data are then used to produce data sets that are further analyzed using algorithms that correct the linearity and offsets of the data curves to produce a representative output value for a turbidity value and compared with the target value. This process is repeated until the target turbidity is obtained as described elsewhere herein.

The system 1000 may also comprise a conveyor of which the end position can form the stage 2 for the culture dish or a conveyor and a stage 2 which can be mutually positioned such that a culture plate can be transported onto the stage and removed from the stage by appropriate operation of the conveyor. The conveyor is controlled by the controller 30 for automatically positioning and removing a culture dish comprising the microorganism on and from the stage, respectively. Please note that in other, not shown, embodiments different means for automatically positioning and removing a culture dish on and from the stage, respectively, can be used. In particular the controller 30 is arranged for allowing a culture dish to be automatically removed from the stage by the automatic culture dish positioning and removing device only after the signal that the suspension tube with the suspension can be removed from the suspension tube holder for further processing has been provided. This ensures that it is always possible to pick up an additional sample, if necessary.

As shown in FIG. 2 the inventive apparatus 1000 may also comprise an automatic suspension tube positioning and removing device (not shown) for automatically positioning and removing a suspension tube in and from the suspension tube holder, respectively. Such automatic suspension tube positioning and removing device may include a grasping means for releasably grasping a suspension tube 11. Again, the controller 30 may be arranged for being communicatively connected to the automatic suspension tube positioning and removing device for controlling the operation of the automatic suspension tube positioning and removing device, and for automatically positioning a suspension tube 11 in the suspension tube holder 10. The controller 30 in particular is arranged for automatically removing a suspension tube holder from the suspension tube holder by the automatic suspension tube positioning and removing device only after the signal that the suspension tube with the suspension can be removed from the suspension tube holder for further processing has been provided. The automatic suspension tube positioning and removing device may be movable along the rail 18 independent of the movement of positioning device 8. Suspension tubes 11 can be fetched and suspension tubes with a suspension medium containing a sufficient concentration of microorganism can be handed over to equipment for further processing, such as an incubator. Please note that a multitrack system can lead the suspension tube positioning and removing device and the positioning device 8 to different locations at which different components are present or processes can be performed.

The sample suspension thus prepared is used for performing characterization or identification of the microorganisms using MALDI and optionally used for other analysis, such as AST. For identifying microorganisms using MALDI an aliquot of the sample suspension is obtained using a pipetting or pick tool and this aliquot is transferred onto the target plate 42. A drop can be obtained by using such tool 46 which is held by the grasping means 49 of pipettor 40 and is then automatically lowered in the suspension at position A. When this tool 46 is raised out of the suspension a drop of suspension will stick on the tip of this tool 46, which can be transferred along the track to position B, where the tool 46 with the suspension is lowered until the drop of suspension contacts the depositing spot 44 on the target plate 42. At least a part of the suspension will remain on the depositing spot 44 after the tool 46 has been raised away from the target plate 42. Alternatively pick tool 6, can be used to pick up an amount of suspension 14 from the suspension tube 11, transfer this amount to position B and deposit a drop of suspension on the target plate 42. After a drop of suspension has been deposited on the target plate 42, and in particular when this drop has been allowed to dry, MALDI matrix solution is automatically overlaid on the amount or portion of the sample deposited on the target plate 42. For performing other tests or another analysis a second drop of the sample suspension can be obtained in a similar way, and such a drop may be automatically transferred to and deposited on e.g. a test culture dish which is further transferring in an automated way for performing a susceptibility test or another additional analysis.

In one embodiment, the matrix solution is dispersed onto the target plate 42 in multiple spots. This improves throughput and reduces the cost of consumables such as pipettes and the like. In this embodiment, a sufficient volume of Matrix solution (that is, a Matrix solution for many target spots) is aspirated into a pipette and that pipette is used to dispense multiple spots sequentially. Typically, dispensing low volumes of fluid in the range of 1 uL to 20 uL requires touching the fluid droplet to the surface in order to be dispensed to allow the surface tension of the fluid contacting the target plate to pull off the droplet from the pipette tip 46. During the process of "touching off" the droplet onto the target plate surface, the pipette tip 46 can non-intentionally touch the surface of the target plate 42. If the pipette tip 46 touches the target plate 42 there is a risk of carrying over sample material from one target plate spot to the next resulting in cross contamination. In an effort to prevent cross contamination capacitive liquid detection is integrated into the pipettor 40 to detect when the droplet touches the target plate 42. The capacitive liquid detection is used to make multiple dispenses from a single volume of matrix solution in a single pipette according to the following steps.

First, a new pipette tip is picked. After that a dry tip is moved to the target plate 42 and the plate is touched with the pipette tip 42 on a non-target position to determine and record the precise vertical (Z) position of the location of the target plate to tip interface.

Then, a sufficient volume of matrix solution is aspirated from a matrix reagent container. The container has a septum to prevent evaporation of the matrix solution. After aspiration of matrix solution and the tip is removed from the matrix container, the septum wipes off any residual matrix fluid that may have coated the tip 46. This ensures the droplet will form on the end of the tip when the matrix solution is dispensed from the tip and not move up the side of the tip 46.

The pipette tip 46 is then moved to the target plate 42. A droplet is formed at end of tip 46. The tip 46 is moved down in the vertical (Z) direction until the droplet touches the target plate spot 44. When the droplet touches the plate the capacitive sense circuit causes a signal that indicates the droplet is touching the plate 42. The vertical (Z) position of the tip 46 is checked to confirm that the tip 46 is not touching plate 42. If the tip 46 is not touching plate 42, the multi-dispense process is continued. If the tip 46 is touching the plate 42, the tip 46 will be ejected into waste, a new tip acquired, and the dry tip moved into position to touch the target plate to establish a new tip-touch-to-target plate vertical (Z) position and the process continues until all target spots 44 on the plate 42 are inoculated with matrix solution.

Obtaining Sample for Id and AST from the Same Suspension

Preparation of a suspension from one colony pick that is used for both MALDI and AST testing is described in U.S. Pat. No. 9,180,448 which is commonly assigned with the present application and incorporated by reference in its entirety. The disclosure herein may refer to a Sample preparation apparatus (Sample prep or prep station hereinafter) as a "Phoenix AP", or an AST system as a BD Phoenix™ or refer to a mass spectrometry system as MALDI, but it should be understood that the meaning of these terms is not limited to the apparatus having these trademarked names, but may include apparatus having a substantially similar functionality. Apparatus having substantially similar functionality may include the Vitek (bioMerieux) and MicroScan (Siemens Healthcare) ID/AST systems.

In one embodiment, the apparatus described herein integrates the microbial identification capabilities of a MALDI instrument with the AST and data processing capabilities of a laboratory analysis or processing system such as the Phoenix, Phoenix AP, BACTEC, or EpiCenter systems.

As described above, a suspension is prepared from microorganisms picked from a prepared plate 3 or taken from a blood culture vial. In one embodiment, the suspension tubes 11 are over inoculated with the microorganisms 4. The tubes 11 are advantageously used as the source for both ID and AST. This ensures that not only the same patient sample, but also the same isolate, is subject to the ID and AST testing.

The suspension is prepared for a concentration suitable for MALDI. Suspensions suitable for MALDI typically have a McFarland value of about 2. An automated system is used to inoculate the suspension tube 11 with the pick tool 6, monitor the turbidity, and process the suspension to provide a suspension with the target turbidity. Automated processes for providing suspensions with target turbidity are described in detail herein. The suspension is then used to inoculate the MALDI plate 42 as described above. As noted above, the system 1000, through use of machine-readable tags and codes associates the culture dish 3 with the suspension tube 11 and the MALDI plate 42. In one embodiment, the apparatus scans the barcode on the MALDI plate 42 and writes the plate ID to the RFID tag on the suspension tube rack. The system 1000, using the automated pipettor 40, automatically adds the MALDI reagents (e.g. formic acid, matrix, etc.) to prepare the suspension dispensed on the MALDI plate 42 for analysis as described herein.

The system 1000, using the automatic pipettor 40, or dispensing nozzle 30, then dispenses additional solution (e.g. deionized water) into the tube 11 and nephelometer 20 monitors the turbidity to provide a suspension with a turbidity suitable for AST or other diagnostic test (e.g. molecular testing). The automated system and method for providing a suspension with target turbidity is described in detail herein and is not repeated. For AST the target turbidity is about 0.5 McFarland and typically not less than about 0.25 McFarland. The pipettor 40 then transfers an aliquot to the AST tube 82. The RFID tag on the test tube rack is updated with adjustment result.

AST tube 82, as shown in FIG. 2, is held by an AST tube mover 80. AST tube mover 80 is a robot generally disposed beneath a system deck 7 and is configured to move in at least two dimensions, as illustrated by the vertical and horizontal arrows in FIG. 2. In particular, AST tube mover 80 is configured to hold, such as by a receptacle or gripper, an AST tube 82 and move the AST tube 82 underneath the deck 7 and move the AST tube 82 between predesignated positions located at the preparation station 1030 and transfer station 1040, respectively. In this regard, the deck 7 may have openings through which the mover 80 can raise and lower AST tube 82 at these predesignated positions. Of course it is also contemplated that a suspended tube gripper robot 50 could move AST tube 82 between preparation station 1030 and transfer station 1040 from a suspended position above deck 7, rather than from below deck 7.

AST tube 82 may be stored within station 1040. Prior to aliquot transfer to AST tube 82, tube gripper robot 50 grips the AST tube 82 via gripping means 59 and moves the tube 82 from its storage position to a bar code scanner so as to register tube 82 with controller 30. Thereafter, gripper robot 50 hands off tube 82 to mover robot 80. Robot 80 then shuttles the tube 82 beneath deck 7 to a position C located at preparation station 1030 where the tube 82 is raised at least partially above the deck. Pipettor 40 then retrieves an aliquot of the diluted suspension from tube 11, moves to position C, and then inoculates the AST tube 82 with the aliquot at position C. The tube mover 80 then shuttles tube 82' with the suspension therein back to transfer station 1040, as is depicted by FIG. 2.

While at station 1040, another pipettor 60 retrieves an aliquot of the suspension from the AST tube 82'. Prior to retrieval of this aliquot, a cartridge transfer robot 70 grips an empty AST cartridge 90 via a gripper means 79 and transfers cartridge 90 from a storage location to a cartridge filling unit 78 which includes a cartridge holding structure for holding cartridge 90. The unit 78 may be movable so as to pivot the cartridge 90 from a vertical configuration to an inclined configuration, as shown, for ease of inoculation. A decapper (not shown) may also remove a cap that seals the cartridge 90 prior to inoculation. The pipettor 60 then automatically inoculates the AST cartridge 90 with the diluted suspension. Both the AST suspension tube 82 and the AST cartridge 90 bear codes the permit association of the suspension subjected to AST analysis with the pick from which the suspension was prepared. The apparatus has a data management system that associates the cartridges with the suspension used to inoculate the cartridge 90. The system 1000 reads the MALDI plate ID and plate positions for each suspension and makes the necessary associations with the picked colony from the identified culture plate 3 with the suspension prepared therefore and the MALDI plate 42 and positions on the plate 42 inoculated with the relevant suspension and the AST suspension tube 82 and AST cartridge 90 inoculated with the AST suspension. Automation is provided to inoculate the AST cartridge and to convey the inoculated cartridge to a testing instrument that performs AST on the inoculated cartridge. An exemplary cartridge transfer instrument for automatically moving an inoculated cartridge 90 into and removing a tested cartridge from an AST testing instrument is described below.

Preparing a Maldi Plate Using a Layering Technique

In one embodiment of the present invention, the suspension is automatically deposited on the MALDI plate 42 using a dispense/layering method. This method is described in U.S. Provisional Application No. 62/038,509 filed Aug. 18, 2014 entitled Method of Sample Preparation for Maldi and commonly assigned with the present application, which was filed as PCT/US21015/45506 published as WO2016028684. U.S. Provisional Application No. 62/038, 509 and PCT/US21015/45506 are incorporated by reference herein in its entirety.

In the solution dispense/layering method described herein, the bacterial suspension that will be dispensed is first evaluated to determine its turbidity as described elsewhere herein.

The bacterial suspension is created as described elsewhere herein. The solution dispense layering method requires, as implied by its name, the formation of two or more layers of solution for identification by MALDI. A selected volume of sample is dispensed on the MALDI plate 42 and dried. Subsequently, at least a second aliquot of suspension is dispensed (preferably the same volume) on the dried suspension. Dispense is accomplished using the automated methods described above. The second dispensed aliquot is dried. Optionally, more layers of suspension can be deposited and dried. After the final of the two or more layers is dried, the sample is processed for MALDI (e.g. by adding formic acid and then applying the matrix over the sample as described herein). The sample is then evaluated by MALDI. The solution dispense/layer method has been determined to provide acceptable MALDI results for liquid samples with McFarland turbidity values significantly less than 2.0 for both Gram positive and Gram negative bacteria.

For example, in one embodiment, if the liquid bacterial suspension (prepared from a bacterial colony picked from an agar plate and suspended in water (mass spectrometry grade) as referenced above, has a value of 0.5 McFarland, that value is significantly below the value of 2.0 McFarland, which is an indication that the solution dispense/layering sample preparation should be used to prepare this sample for MALDI.

After determining to use solution dispense/layering to prepare the sample for MALDI, the amount of suspension is selected per layer. In the above example with a sample having a 0.5 McFarland value, the volume per layer of at least about 3 µl but not exceeding about 4 µl is selected. The number of layers is governed by the turbidity value and the sample volume. Once the volume of the layer is selected and deposited on the MALDI plate, the sample is dried. The exact drying conditions are a matter of design choice and are selected to provide quick drying while preserving sample integrity for MALDI testing. Suitable drying conditions are readily determined by one skilled in the art. For example, the drying steps can be completed at either ambient temperature or with the assistance of a hot plate (illustratively, about 40° C. to about 45° C.). After drying, a second layer of suspension is deposited over the first layer. The second layer has the same volume as the first layer. If needed, additional layers are added and dried. Since the layering method requires additional time and resources, the number of layers is limited to that number needed to obtain accurate results from MALDI.

Following the solution dispense/layering sample deposition, the sample target well is processed using the typical MALDI procedure (addition of 70% formic acid and matrix).

It has been determined that the sample preparation process for MALDI depends upon a variety of factors, but most significantly: i) the concentration of the microorganisms in the suspension; ii) the volume of the suspension; and iii) if applicable, the number of dispenses. The microbial concentration is reflected by the turbidity of the sample. Roughly, the higher the turbidity, the higher the microbial concentration.

Turbidity is measured by nephelometry as described elsewhere herein. Once the turbidity of the suspension is assessed as previously described, a decision on how to go about sample preparation for MALDI is made. Such a determination is made by evaluating the turbidity information and sample volume. In these embodiments the sample information is entered into a data base. The data base (pre-programmed with information regarding the sample preparation best suited to the particular sample) outputs the recommended method for MALDI sample preparation.

In the automated system, a processor controls the MALDI preparation protocol, depending upon information that the processor receives regarding the sample. The system processor compares the measured turbidity with a predetermined turbidity threshold as described herein. If the processor determines that the sample turbidity is within the predetermined range of turbidity values, then the processor provides instructions to transfer a predetermined volume of the diluted sample to the MALDI plate 42. The automated system prepares the sample for MALDI (i.e. the addition of formic acid to fix the sample followed by application of MALDI matrix solution over the sample prior to MALDI as described elsewhere herein) based on instructions from the processor. If the processor determines that turbidity is above the predetermined range, the processor provides instructions to prepare a MALDI sample using less than the typical volume (i.e. if a 0.5 µl is normally deposited on the MALDI plate 42, only 0.25 µl is deposited on the MALDI plate 42 instead for the high turbidity samples). If the processor determines that turbidity is below the predetermined range, the sample is deposited in layers on the MALDI plate 42, with drying of the sample between deposits. As noted above, since the method and apparatus described herein are fully automated embodiments, the system uses the above describe automatic pipettor described herein to dispense the suspension on the MALDI plate 42 based on instructions from the processor.

Figure 14:
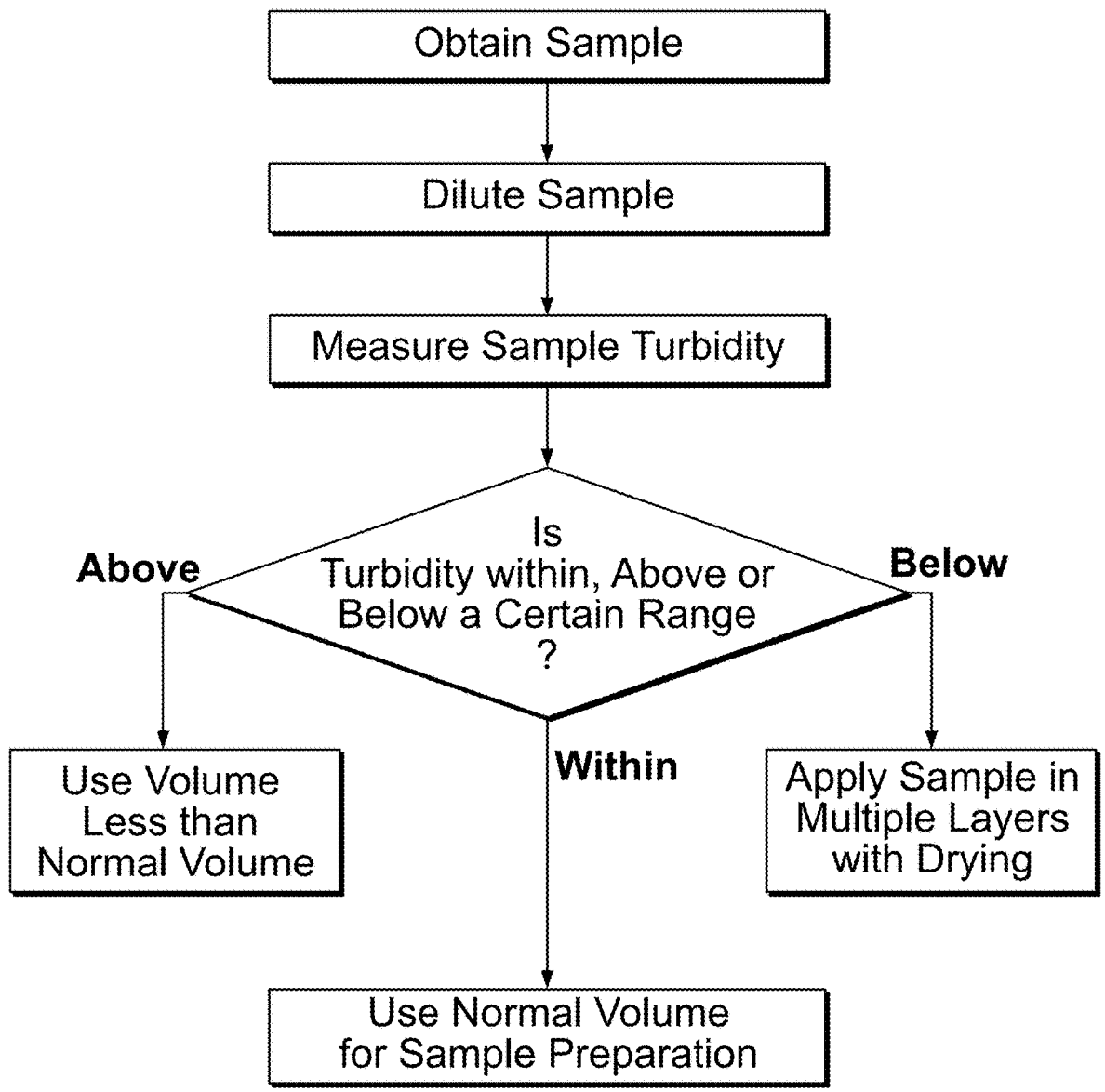
FIG. 14 is a sample preparation decision tree where sample preparation is based upon measured sample turbidity.

FIG. 14 illustrates the process flow for the automated process of multiple dispenses of suspension onto a MALDI plate 42. The suspension is automatically prepared and its turbidity assessed as described elsewhere herein. If the measured turbidity is within a predetermined range, an aliquot with a predetermined volume is deposited on the MALDI plate. If the measured turbidity is higher than a predetermined range, then a smaller volume of sample is deposited on the MALDI plate 42. If the measured turbidity is less than the predetermined range, then the above-described sample preparation protocol using multiple dispenses with drying between dispenses is used.

In one exemplary embodiment, a sample is obtained and a suspension is prepared. The turbidity is measured. If the turbidity (in McFarland) is between about 2 and about 6, about 3 µl is deposited on the MALDI plate 42. If the sample turbidity is higher than about 6 then the amount of sample deposited on the MALDI plate 42 is reduced to about 1 µl. If the sample turbidity is less than about 2 but in the range of about 1 to about 2, then about 3 µl of sample is deposited on the MALDI plate 42, dried, and a second 3 µl sample is deposited and dried. If the sample turbidity is about 0.5 to about 1, then three "layers" of suspension, each about 3 µl, are deposited and dried. If the sample turbidity is about 0.25 to about 0.5, then 4 "layers" of suspension (3 µl each) are deposited and dried.

After the sample is deposited and dried, the samples are processed for MALDI as described elsewhere herein.

Each suspension tube comprises an unique identifying mark, which is stored together with the properties of the suspension with a link to the identity of the culture dish from which the selected colony of microorganisms was obtained in the memory of the central control computer for the purpose of amongst other things correctly and in a fast manner link the obtained results of analysis with the culture dish and colony pertaining to the results.

In yet additional embodiments, the system has a predetermined range of turbidity where no dilutions for either MALDI or AST will be required. If the turbidity is within this predetermined range (e.g., about 0.5 to about 2 McFarland), then the suspension can be used to inoculate the MALDI plate 42 using the layering method so described above (if the concentration of the suspension is not sufficiently high so that one dispense will do). In this embodiment, the volume of the suspension inoculated into the suspension tube is also varied depending upon the measure turbidity. For example, if the McFarland value for the suspension is 0.5, then a volume of 25 µl is inoculated into the suspension tube. For that same specification then, if the nephelometer measures a 1 McFarland suspension, then only 12.5 µl of that suspension would be used. Both dispenses deliver about the same amount of microorganisms into the suspension tube 11, but the volume of the 0.5 McFarland suspension is twice the volume of the 1 McFarland suspension. There is therefore an inverse proportional relationship between the McFarland value of the suspension and the volume of the suspension inoculated into the AST tube 82. The higher the McFarland value, the lower the volume of the suspension that is inoculated into the suspension tube 11. This is because, for AST, it is the amount of the microorganism inoculated into the tube 11 and not the volume that determines if the dispensed amount is adequate. If the nephelometer 20 determines that the suspension is within the predetermined range, the information is communicated to the controller 30, which then determines if the dispense onto the MALDI plate 42 must be done by the layering method or if a single dispense is sufficient. The controller 30 also will determine the volume of suspension to be dispensed into the AST tube 82 referencing a look up table that will specify dispensed amount as a function of measured turbidity.

Inoculation of a cartridge for AST is described in U.S. Pat. No. 6,096,272 to Clark et al. which is incorporated by reference herein. In practice, the suspension is inoculated into an AST inoculum fluid which is then transferred into the test cartridge 90 using the automated mechanisms for fluid transfer described above. The AST cartridges 90 are inclined with the inoculation ports at the top for filling (see FIG. 25). Each well in the AST cartridge 90 is inoculated with the AST inoculum fluid. The inoculum flow down the AST cartridge in a serpentine fashion, filling the wells as the liquid front progresses toward an absorbent pad. Each well is vented, permitting liquid to fill the well. Each well has a sharp, circular rim to separate a consistent quantity of liquid from the excess and to isolate each well from liquid in adjacent wells 31. The pad absorbs excess liquid.

As shown in FIG. 2, an amount of suspension can be taken from the suspension in the suspension tube by means of a pipetting tool 46 which can be automatically held and positioned by the grasping means (functioning as pipetting tool holder) 49. Pipettor 40 is arranged for positioning the pipetting tool 46 in a starting position above the suspension tube 11 and for automatically lowering and raising the pipetting tool 46 into and out of the suspension and for positioning the pipetting tool 46 in a transfer position B above MALDI plate 42, respectively. When the pipetting tool 46 is lowered into the suspension in the suspension tube 11 the pipetting tool 46 is operated in a manner known per se (e.g. using sub pressure) to pick up an amount of suspension. Thereafter the pipetting tool with the amount of suspension is raised to the transfer position. For holding the amount the pipetting tool comprises a pressurizable chamber closed by a controlled valve. The pipetting tool 46 is automatically transferred to the position B above one of the depositing spots 44 of the target plate 42. In this position the pipetting tool 46 is lowered to a predefined distance above the target plate 42, after which the chamber is pressurized to a pressure in a range of about 0.5 bars to 1.1 bars. The valve is then opened for such a time that a drop of suspension with a volume in a range of about 0.5 to 3.0 µl is deposited on the depositing spot 44, in particular covering at most approximately half of the one of the depositing spots of the target plate 42. After the drop has been deposited the pipetting tool 46 is raised from the target plate 42 and can be transferred to position where it can be discarded or cleaned for reuse.

Figure 18:
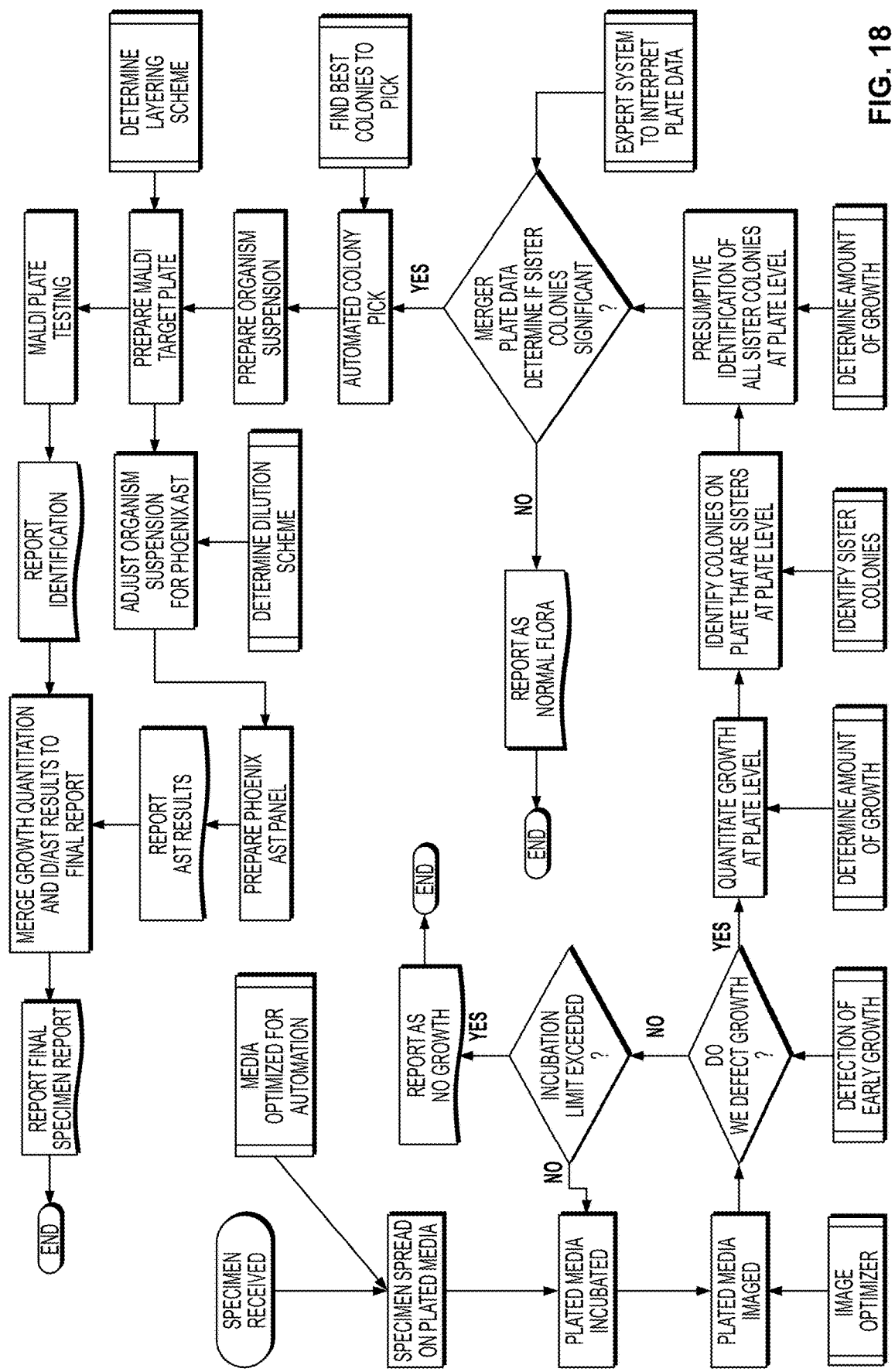
FIG. 18 is a flow chart illustrating an automated process according to one embodiment of the present invention
Figure 19:
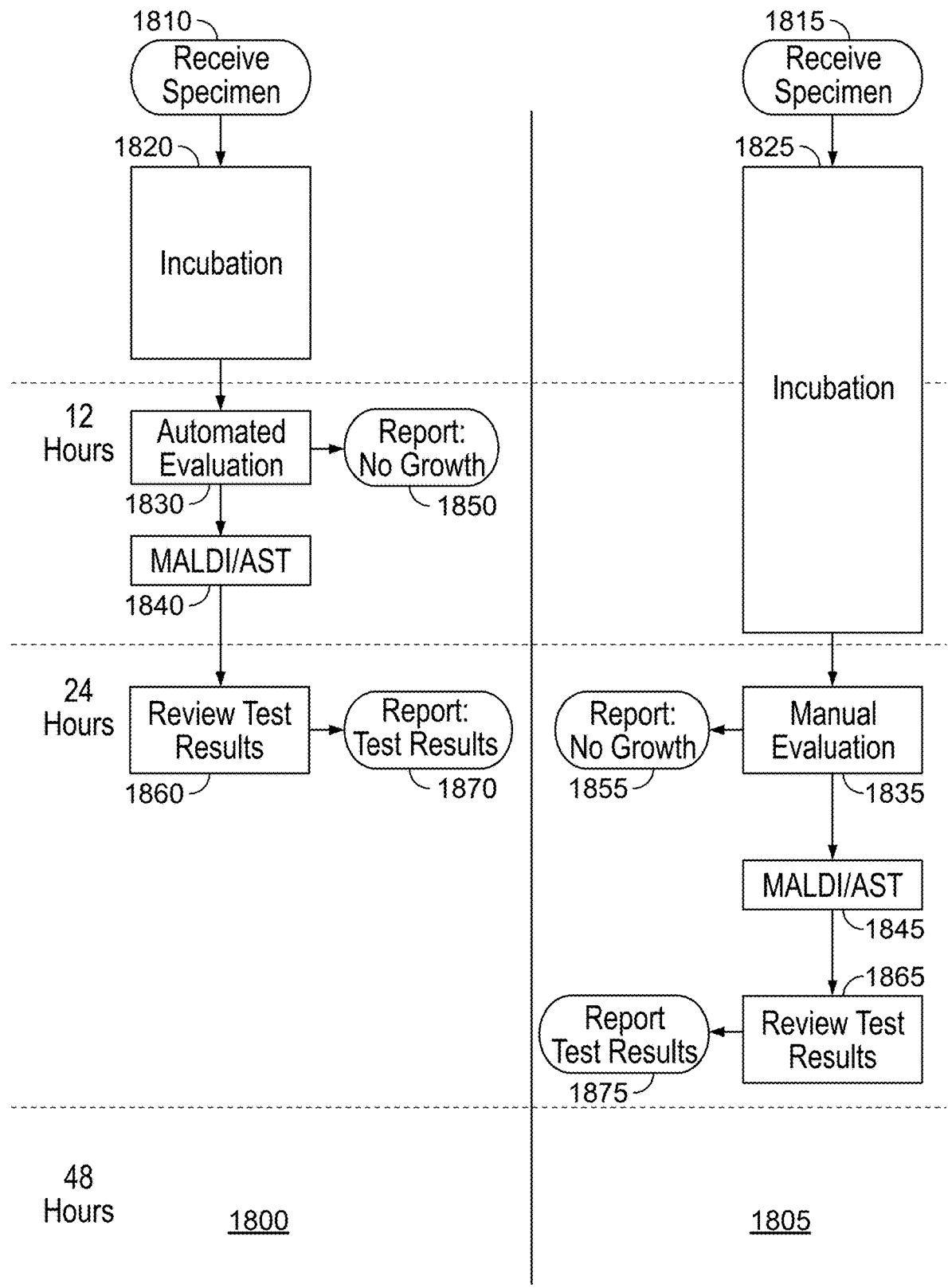
FIG. 19 is a flow chart comparing the timeline of the automated process of FIG. 18 to the timeline of a comparable manually performed process.

FIG. 19 shows a flow chart comparing a timeline of the automated process of FIG. 18 to a timeline of a comparable manually performed process. The manual process is shown to take up to 48 hours, and requires a 18-24-hour incubation period, only after which is the plate evaluated for growth. By contrast, because the automated process can detect even relatively poor contrast between colonies (compared to background and each other), only 12 18 hours of incubation is necessary before the specimen can be identified and prepared for further testing (e.g., AST, MALDI).

Additional aspects of the previously describe embodiments are described below. The user interface previously described provides an image of the culture plate to the user. The user can interact with the interface to pick colonies of interest from the plate.

When the user selects a colony, the apparatus provides menu choices for the user to select one of MALDI, AST or both for sample processing. Based on the size of the pick tool (i.e. the pipette described elsewhere herein) the apparatus provides a pick tolerance to ensure that the colony is picked in a designated area. The pick is then locked on to the target and the colonies are picked. In one embodiment the diameter of the pick tolerance is 5 mm. With a picktool having a diameter of 3 mm this distance ensures that a 1 mm diameter area in the pick tolerance area will be picked. The processing selections are sent to the controller to enable tracing the processing of the sample.

The system overview in FIGS. 1-3 illustrates identification (MALDI-TOF) and AST (antibiotic susceptibility) preparation locations and a user interface touchscreen 1006. FIG. 2 illustrates the dish 3 with colonies 4 thereon being designated for pick being moved to the pick station 1020 of the system. The dish 3 is aligned for colony pick in the manner described previously herein. The dish 3 is then scanned for traceability.

The dish's cover is then removed and the pipette pick tool 6 is moved over the selected colonies 4. The positioning device 8 moves the pipette pick tool 6 from the pick position to the inoculation position A where the colonies are placed into the suspension tube 11 as previously described. The tubes or cuvettes are described previously herein. The pipette 6 brings the sample into the tube 11 which has the suspension liquid already present therein. The relative amount of suspension is controlled so that the suspension meets the predetermined McFarland standards as described previously herein.

Just as the samples, suspensions, etc. are traceable throughout processing in the method and apparatus described herein, so are consumables in the apparatus and method trackable by barcode. The apparatus will provide fully automated inventory control of consumables within the apparatus.

When the suspension is deposited on the MALDI target plate 42, it can be spotted in layers as described elsewhere herein. Drying of the sample and formic acid extraction is also previously described. Depositing the MALDI spots on the target plate 42 followed by deposition of the matrix solution is automated as previously described.

After the aliquot for MALDI is obtained from the suspension, the suspension is further used for inoculation of the tubes 82 for AST testing. In one embodiment a larger pipette 46 is used for AST tube inoculation than for colony pick. In one embodiment 50 µl pipettes are used for colony pick and 1 ml pipette tips are used to prepare the suspension for AST. The target turbidity for AST in one embodiment is 0.5 McFarland (McF). AST tubes with AST broth therein are extracted from a rack. In one embodiment the broth tubes also contain Alamar Blue (Alamar Biosciences, Sacramento, Calif.). Alamar Blue is an oxidation-reduction colorimetric indicator that changes hue from a deep blue to a bright pink in the presence of metabolically active, growing organisms. The use of Alamar Blue in susceptibility assays is well known to the skilled person and is not described in detail herein. The AST tube 82 is scanned as one illustration of the traceability of consumables, reagents and sample throughout the system. The cap is removed from the AST broth tube using a decapper and the cap is then disposed of, after which the AST broth tube 82 is transferred to a position where an AST panel 90 is inoculated. The inoculation position is illustrated in FIG. 2. FIG. 2 illustrates the automatic pipettor 60 used to inoculated the AST panel 90 with the AST broth in the bottle on the left. Dye is provided to change the color of the broth. FIG. 2 illustrates the pipette 46 that is used to inoculate the AST tube with the 0.5 McF suspension. FIG. 2 illustrates that the pipette 46 is used to mix the suspension in the AST tube 82 by repeatedly aspirating and dispensing of the solution.

FIG. 2 illustrates the automation of providing the AST panel 90 (another consumable) for inoculation. FIG. 2 also illustrates AST panel 90 inoculation. The recap of the AST panel 90 is also automated. FIG. 2 therefore illustrates how the apparatus that provides for a seamless process and workflow for sample preparation for both ID and AST. System 1000 can be configured as modular performing only one of identification (MALDI-TOF), antibiotic susceptibility (AST) or both. It is contemplated that the apparatus described herein can be integrated with larger systems such as Work Cell Automation of Total Lab Automation.

Cartridge Transfer

Figure 20:
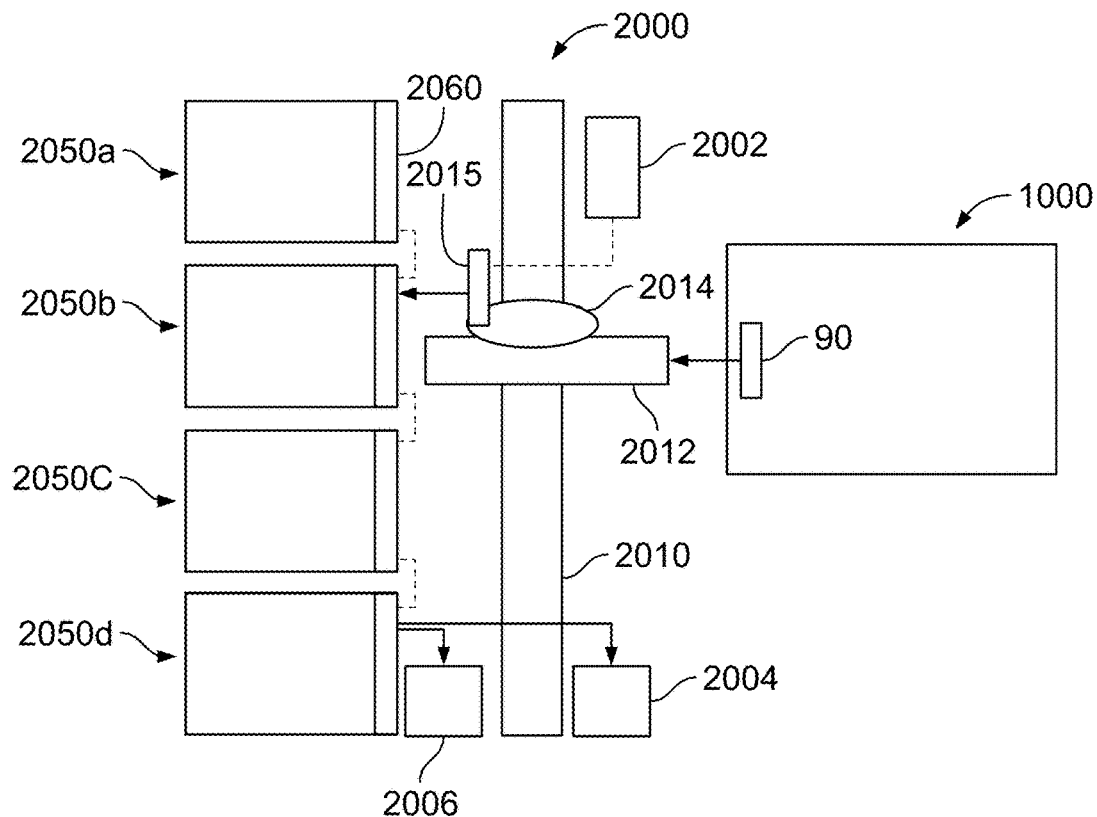
FIG. 20 is a schematic side view of the system of FIG. 1 in conjunction with a cartridge transfer instrument and a plurality of testing instruments.

As such, system 1000 can be used in conjunction with other laboratory systems/instruments to help fully automate sample preparation and testing. As shown in FIG. 20, system 1000 may be utilized in conjunction with an automated cartridge transfer instrument 2000 and one or more cartridge testing instruments 2050a-d. As previously described, system 1000 can automatically prepare AST cartridges 90 for testing. In the embodiment depicted, the cartridge transfer instrument 2000 is particularly configured to transport such prepared AST cartridges 90 from system 1000 to one of a plurality of AST cartridge testing instruments 2050a-d.

Figure 21:
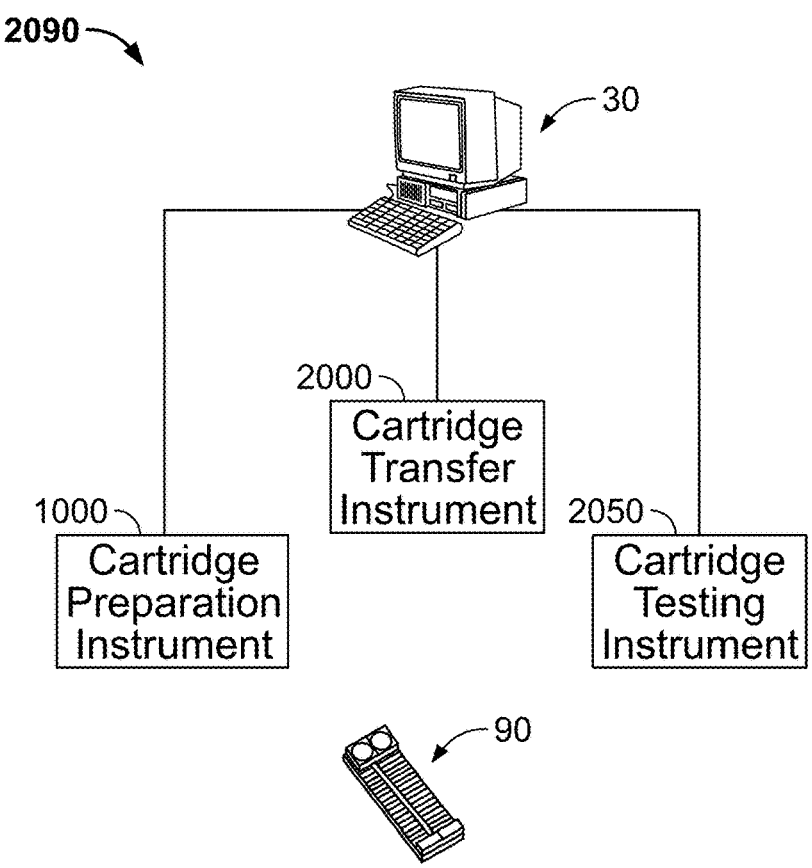
FIG. 21 is a diagram of an example system for automatically preparing, transferring, and testing a sample including the system, cartridge transfer instrument, and testing instruments of FIG. 20 and also including an exemplary microbiology test cartridge and the controller 30 of FIG. 3.
Figure 25:
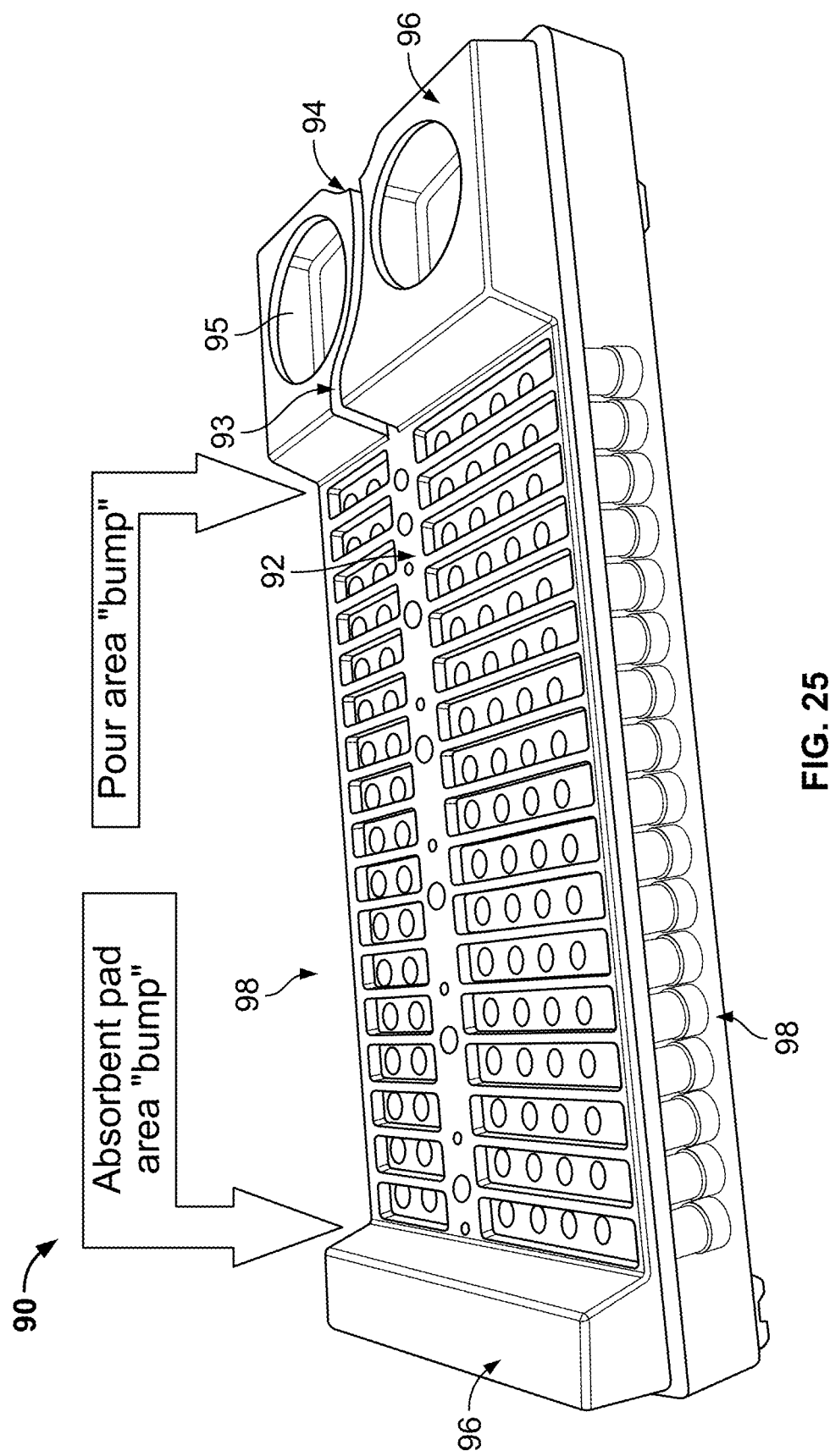
FIG. 25 illustrates the exemplary microbiological test cartridge of FIG. 21.
Figure 26:
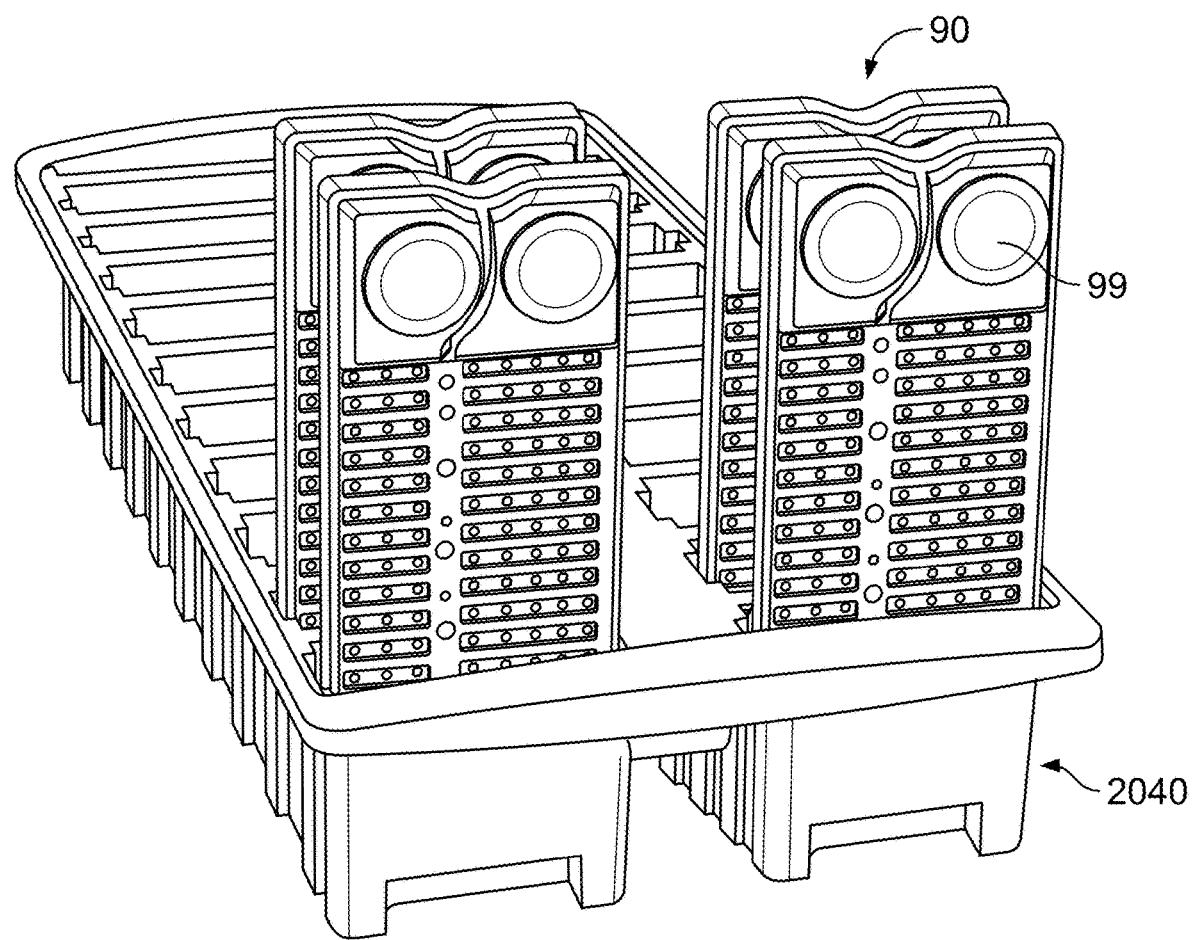
FIG. 26 illustrates a tray for temporarily storing cartridges.

AST cartridge 90, as shown in FIGS. 21, 25 and 26, can be any cartridge available for testing an analyte/inoculum. For example, cartridge 90 can be any cartridge for performing antibiotic susceptibility testing, such as the BD Phoenix™ ID/AST Panel (Becton, Dickinson, and Co., Franklin Lakes, NJ). Whichever cartridge is used, such cartridge 90 generally includes an inlet 95 for inoculating an internal space of the cartridge 90 with an analyte, which can include a microbial suspension or blood culture, for example. Such inlet 95 may be sealed by a removable cap or a septum 99. For example, system 1000 may include a capper/decapper (not shown) in within transfer station 1040 which decaps and recaps removable cap 99.

As illustrated in FIG. 21, controller 30 is coupled to system 1000 (as previously described with regard to FIG. 3), cartridge transfer instrument 2000, and cartridge testing instruments 2050. Controller 30 coordinates and controls each of these systems/instruments 1000, 2000, 2050a-d to perform cartridge preparation, cartridge transfer and sample testing. In this regard, controller 30 is configured to perform certain tasks depending on the type of loading and unloading of cartridge testing instrument 2050. For example, controller 30 may be configured to allow for manual and/or automatic distribution/transfer of cartridge 90 from preparation system 1000 to cartridge testing instrument 2050, manual and/or automatic loading of testing instrument 2050, and manual and/or automatic removal of cartridge 90 from testing instrument 2050, which can then be manually or automatically transferred to storage 2006 or waste 2004. Controller 30 can be in the form of a the depicted desktop computer, incorporated into a touchscreen panel, such as panel 1006 depicted in FIG. 1, or in some other form as is known in the art. Alternatively, multiple controllers can be utilized. For example, controller 30 may be connected to instrument 1000 and cartridge transfer instrument 2000, while another controller (not shown) can be separately connected to testing instrument 2050. Such controllers may communicate with each other to coordinate cartridge transfer.

Cartridge Transfer Instrument

Cartridge transfer instrument 2000, as best shown in FIG. 20, may be a multi-axis robot that includes a z-axis arm 2010, an x-axis arm 2012, a rotation member 2014, a cartridge gripper assembly 2015, and a vacuum pump 2002. The cartridge gripper assembly 2015 is connected to the rotation member 2014 which can rotate the cartridge gripper assembly 2015 so as to face system 1000 in one orientation and to face testing instruments 2050a-d in another orientation. In this regard, rotation member 2014 can rotate cartridge gripper assembly at least 180 degrees about a z-axis. The rotation member 2014 and cartridge gripper assembly 2015 may be connected to the x-axis arm 2012, which itself is connected to the z-axis arm 2010. The z-axis arm 2010 can move cartridge gripper assembly 2015 in a vertical direction so as to access any one of the testing instruments 2050a-d which are depicted as being stacked in a vertical arrangement. Additionally, x-axis arm 2012 can move cartridge gripper assembly 2015 in an x-axis between system 1000 and instruments 2050a-d.

Figure 22:
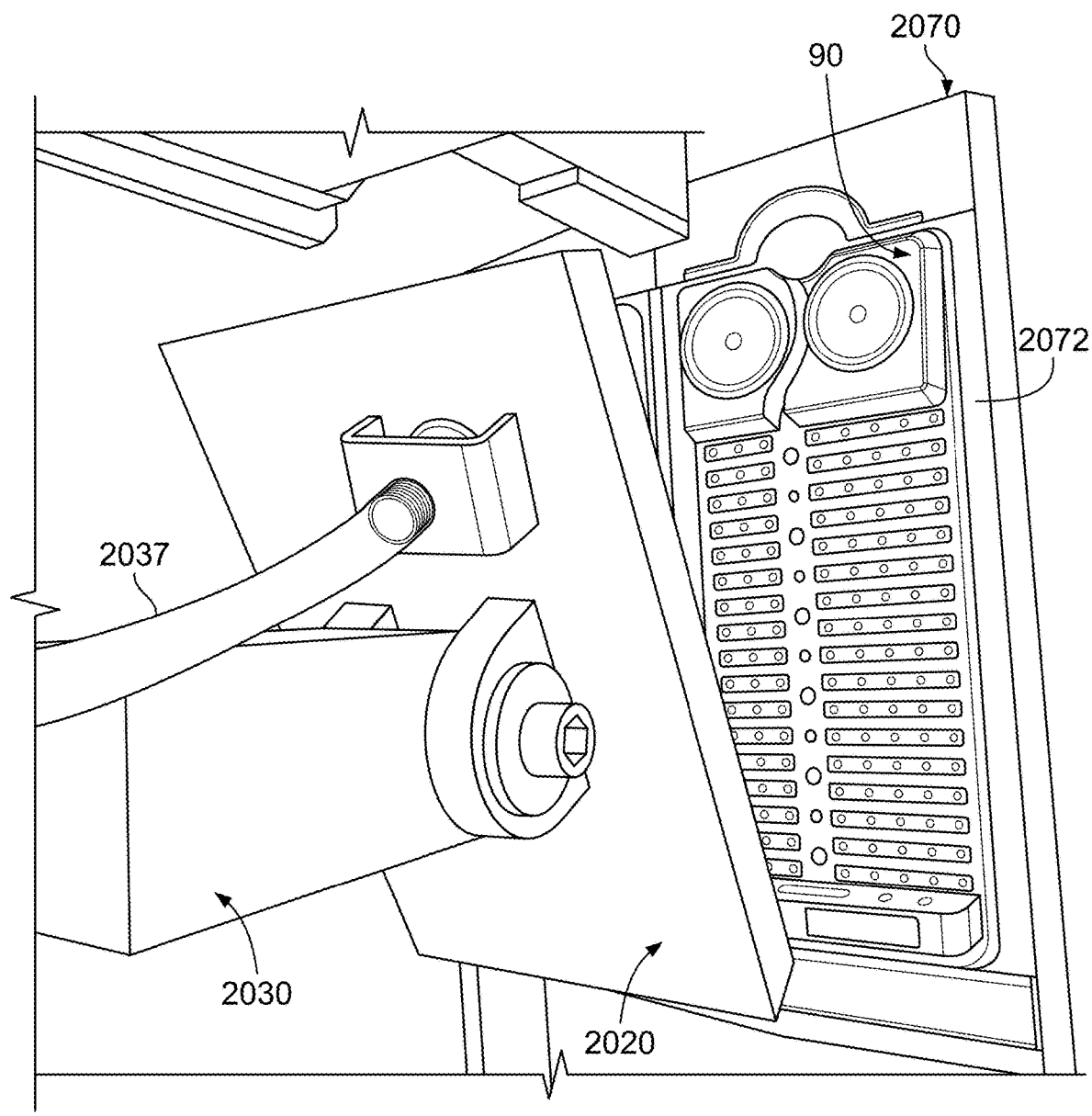
FIG. 22 is a rear perspective view of a cartridge gripper of the cartridge transfer instrument according to an embodiment of the disclosure as it approaches a cartridge in a cartridge holding structure.
Figure 23:
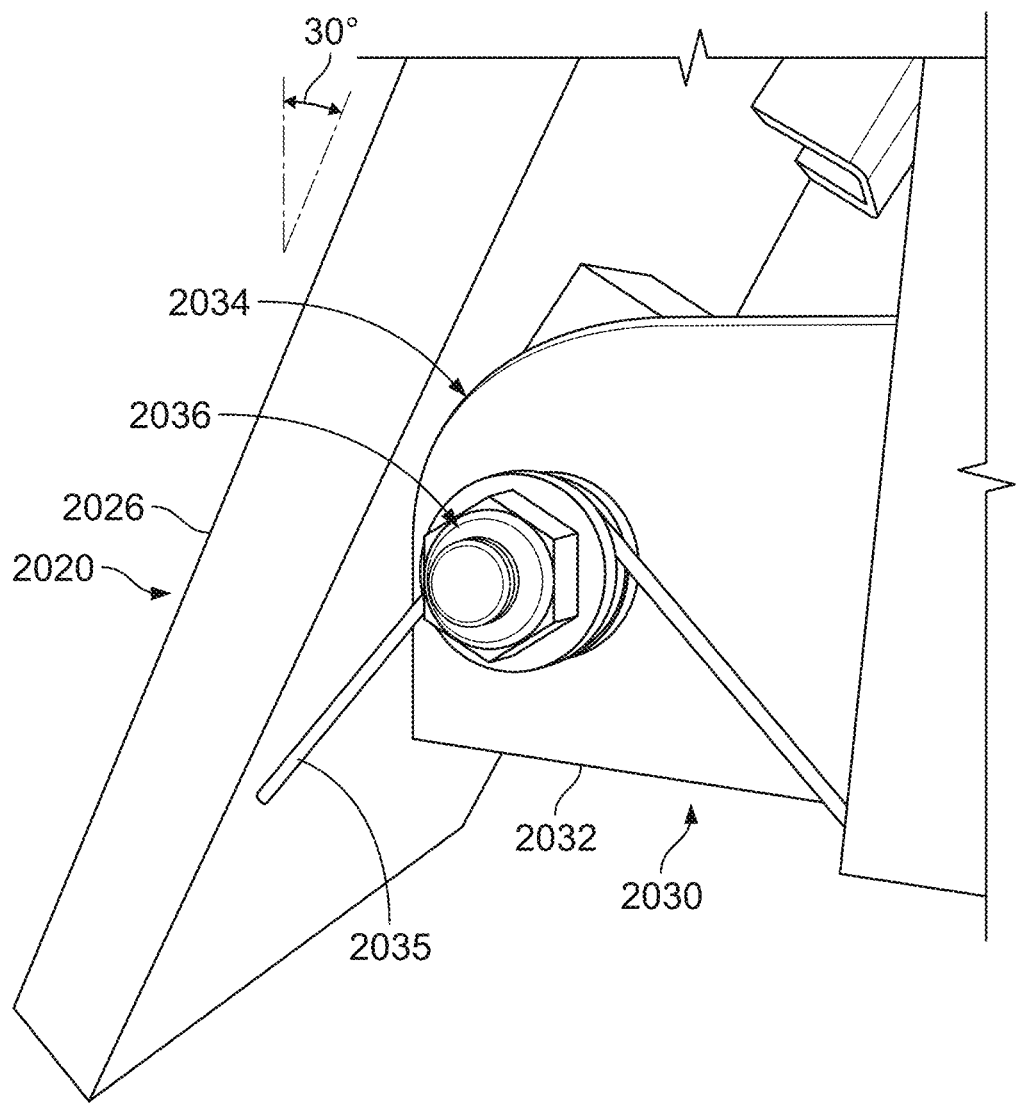
FIG. 23 side perspective view of the cartridge gripper of FIG. 21 that emphasizes a pivotable coupling between a gripper plate and an arm of the automated cartridge transfer instrument.
Figure 24:
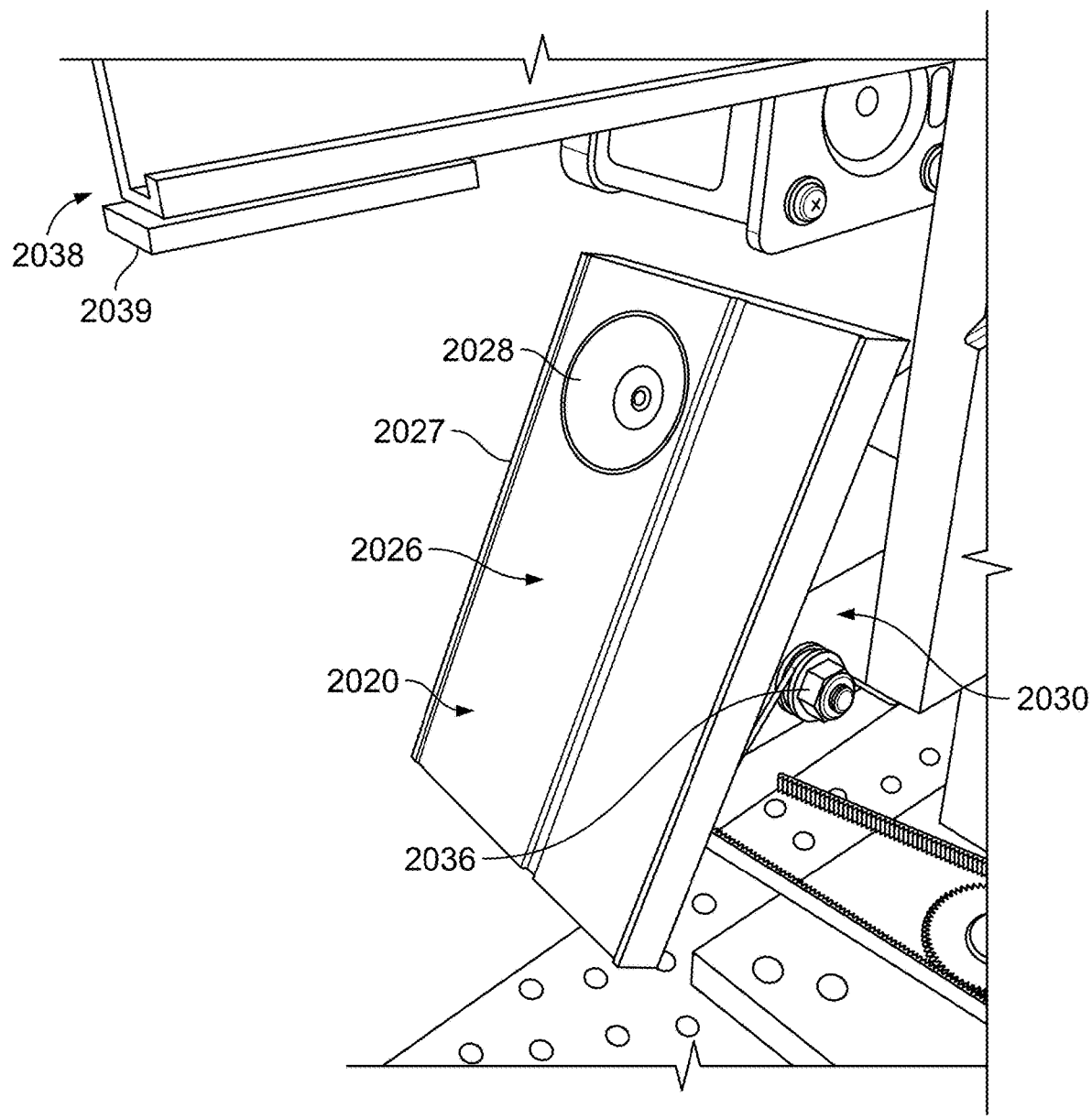
FIG. 24 is a front perspective view the cartridge gripper of FIG. 21.

FIGS. 22-24 depict the cartridge gripper assembly 2015 which generally includes a moveable arm 2030, a support arm 2038, and a gripper plate/member 2020. The moveable arm 2030 is suspended from the support arm 2038 and is moveable relative to the support arm 2038 along an axis thereof, such as by a rack and pinion mechanism. The moveable arm 2030 includes a curvilinear top surface 2034, as best shown in FIG. 23. The gripper plate 2020 is pivotally coupled to the moveable arm 2030 adjacent the curvilinear top surface 2034 and pivots about an axis of a coupling 2036 that connects the two. The curvilinear top surface 2034 helps guide and support gripper plate 2020 as it pivots between a first position and a second position.

The pivot function of the gripper plate 2020 about a pivot axis is further accomplished through the use of a torsion spring 2035, which is depicted in FIG. 23. The torsion spring 2035 is coiled around the coupling 2036 that couples the gripper plate 2020 with the moveable arm 2030. In this way, as a force is applied to the gripper plate 2020 and the gripper plate 2020 pivots from the first position to the second position, tension in the torsion spring 2035 increases. As tension increases, potential energy in the torsion spring 2035 increases so as to be biased toward the first position. In this regard, potential energy of the spring 2035 in the depicted configuration is lowest when the gripper plate 2020 is tilted backward into the first position or resting position so that a cartridge contact surface 2026 thereof is oblique relative to a vertical axis, as best shown in FIG. 23. In the first position, cartridge contact surface 2026 is preferably about 30 degrees relative to a vertical axis. However, it is contemplated that the angle of the gripper plate 2020 may be more or less than 30 degrees when in the resting position.

A force applied to a bottom end of the plate 2020 may cause gripper plate 2020 to move toward the second position or a transfer position (not shown) from the resting position. When in the second position, the spring 2035 is tensioned so that when the force is released from the bottom of the plate 2020, the plate returns to the resting position. In the second position, the cartridge contact surface 2026 of the gripper plate is positioned at a different angle from that of the first position. For example, the gripper plate 2020 is oriented so that cartridge contact surface 2026 is preferably substantially vertical in the second position. However, the second position can be nearly any angle in the range of pivot from the first position and is generally any angle at which the cartridge 2020 is brought into flush contact with an opposing surface 2072. Opposing surface 2072, as shown in FIG. 22, is a surface of a cartridge holding structure 2070 that receives the cartridge 2070 from gripper assembly 2015 or hands off the cartridge 90 to the gripper assembly 2020. Such cartridge holding structure 2070 can be located in testing instruments 2050 and also in instrument 1000. Alternatively, cartridge holding structure can be a tray, such as tray 2040 shown in FIG. 26. Thus, as described, gripping plate 2020 can pivot between a resting positon and transfer position. It is the capacity of the cartridge gripper plate 2020 to pivot that allows the gripper plate 2020 to grip, retrieve, relocate and release objects, such as AST cartridge 90.

The cartridge contact surface 2026 is adapted to grip cartridge 90 upon contact thereof. In one example, gripping is achieved through application of negative air pressure on the cartridge contact surface 2026 of the gripper plate 2020. To obtain negative air pressure, a suction cup 2028 is embedded in the plate's cartridge contact surface 2026 (see FIG. 24) and is connected to a pneumatic conduit 2037 fed through an opening in the plate 2026 which supplies the vacuum from vacuum pump 2002 (see FIG. 20).

In a method of use, gripper plate 2020 is advanced toward a first cartridge holding structure 2070, which may be located in system 1000, via the moving arm 2030 while the gripper plate 2020 is in the first position (see FIG. 22). In this regard, a bottom edge of gripper plate 2020 reaches the cartridge 90 and contacts the cartridge 90 first before any other portion of the gripper plate 2020. Advancing gripper plate 2020 toward cartridge 90 in this manner helps gripper plate 2020 matingly engage the cartridge 90 and dislodge cartridge 90 from the cartridge holder 2070. When the gripper plate 2020 contacts the cartridge 90, the moving arm 2030 continues to advance which applies a force on torsion spring and causes gripper plate 2020 to pivot from the first position to the second position. The second position is reached when the cartridge contact surface 2026 of the gripper plate 2020 is nearly flush with the stationary opposing surface 2072 that retains the cartridge 90. In the second position, the cartridge contact surface 2026 is also generally flush with a cartridge surface 92 (see FIG. 25) so that the vacuum pressure urges cartridge 90 against the gripper plate 2020 and retains the gripper plate 2020 thereon.

Thereafter, when the cartridge 90 is secured to the gripper plate 2020, the gripper assembly 2015 moves away from the cartridge holding structure 2070 which removes the force holding the plate 2020 in the second position which causes gripper plate 2020 and cartridge 90 to return to the first position under the bias of spring 2036. This helps remove cartridge 90 from the cartridge holding structure 2070. Additionally, the moving arm 2030 moves along the support arm 2038 in a direction away from the cartridge holding structure 2070 so that a bumper surface 2039 (see FIG. 24) on the support arm 2038 pushes against an upper surface of the cartridge 90 being held by the gripper plate 2020. This causes gripper plate 2020 to be pivoted back into the second position so that cartridge 90 is oriented in a substantially vertical orientation. This provides clearance from cartridge holding structure 2070 for gripper assembly 2015 to be rotated by rotation member 2014 so that cartridge 90 can be transported to another cartridge holding structure 2070 for receipt thereof.

In this regard, rotation member 2014 rotates gripper assembly toward a second cartridge holding structure 2070, which may be located within a testing instrument 2050. Rotation in this manner allows gripper plate 2020 to be presented to the second cartridge holding structure 2070. When aligned with the second cartridge holding structure 2070, moving arm 2030 is advanced toward the holding structure 2070 which disengages the bumper surface 2039 from the cartridge thereby releasing the force holding the cartridge 90 and gripper plate 2020 in the second position. This causes cartridge 90 and plate 2020 to be moved to the first position as it advances toward the second holding structure 2070. In this regard, a bottom end of cartridge 90 is received first by the second cartridge holding structure 2070. As moving arm 2030 further advances, resistance applied by the second cartridge holding structure 2070 helps pivot cartridge 90 toward the second position so that it is generally flush with a receiving surface 2072 of the holding structure 2070. At this point, the cartridge 90 is received by the holding structure 2070, and the vacuum is turned off allowing gripper plate 90 to be moved away and back into the first position.

Alternative features of the cartridge gripper assembly 2015 are contemplated. For example, in another embodiment, the pivot function of the gripper plate 2020 is supplied through the use of a compression spring (not shown). The compression spring is placed between the gripper plate 2020 and a bottom surface 2032 of the moving arm 2030. In the first position, the compression spring has relatively low potential energy. As the gripper plate pivots 2020 from the first position to the second position, the spring is compressed and the potential energy in the spring increases. In a variant, the compression spring is preloaded with enough compressive force to ensure the gripper plate 2020 is not prone to tilting in either direction prior to making contact with a cartridge holding structure 2070. The compression in the spring serves to hold the gripper plate 2020 in position as the arm 2030 moves the plate 2020 from one location to another.

In yet another embodiment, the pivot function of the gripper plate 2020 is accomplished through the use of a tension spring (not shown). As with the above described compression spring, the tension spring is placed between the gripper plate 2020 and the arm 2030, however, in this instance, the spring is placed over the top surface 2034 of the arm. This ensures that tension increases in the spring as the gripper plate 2020 moves from the first position to the second position, storing more energy toward the latter. In a variant similar to that for the compression spring above, the tension spring can be preloaded in tension in the first position.

In another embodiment, an elastomeric member (not shown) is used to provide the pivot function. The elastomeric member is a structure that deforms from a state of equilibrium when the gripper plate 2020 pivots from the first position to the second position and then returns to its original size when the gripper plate returns to the first position. The elastomeric member is preferably made of a material having a Young's modulus sufficiently low to allow elastic deformation in response to the resistance force generated by contact with a stationary instrument as the gripper plate makes contact and moves closer to cartridge holding structure 2070.

In another embodiment, a wave spring (not shown) provides the pivot function. The placement and operation of the wave spring with respect to the assembly 2015 is similar to that of a compression spring and would otherwise be located and attached in a manner known to those of ordinary skill in the art.

In other embodiments, passive means other than those described above can be used to provide the pivot function. Passive forms of control are well known to those of ordinary skill in the art and are not described in detail herein.

In further embodiments, active means can be used to provide the pivot function. Examples of active control include a linear actuator, such as an electric or pneumatic actuator, a piston, such as an electric or pneumatic piston, rotating ball screw and nut, and rack and pinion. Also contemplated are any other active forms of control known to those of ordinary skill in the art.

In any one of the above embodiments, the gripper plate 2020 can be sized to fit a particular cartridge size. In this way, the dimensions of the gripper plate are not limited to a particular width or length. In addition, the thickness of the gripper plate is largely a matter of design choice provided it is sufficient in view of the material used to support expected object loads.

Also, in any one of the above embodiments, the cartridge contact surface 2026 of the gripper plate 2020 can be adapted to be flush with different cartridge types, shapes and sizes. For example, the contact surface 2026 can be characterized by a concave or convex shape over a length of the gripper plate 2020.

In any one of the above embodiments, the gripper plate 2020 can be adapted to include a variety of surface features for gripping a particular object. For example, the cartridge 90 illustrated in FIG. 25 includes a variety of features that can be used for gripping by gripper plate 2020. These include an interstices gap 93 near a central region of the cartridge running in a generally longitudinal direction, a concave region 94 in a central portion of a top surface of the cartridge 90, bumps 96 at the upper and lower extremes of the cartridge 90, among others.

To accommodate these cartridge features, the contact surface 2026 can include protrusions shaped and positioned to fit corresponding features on the cartridge 90. The gripper plate 2020 can also be structured to expand in between bumps 26 to exert forces in opposing directions on the longitudinal axis of the cartridge 90. Put another way, the gripper plate 2020 can be adapted to grab hold of the bumps 96. It is also contemplated that another gripper plate structure, such as one with opposable fingers, can be adapted to clamp onto sides 98 of the cartridge 90.

In any one of the above embodiments, the surface 2026 of the gripper plate 2020 can include a structure to maintain the alignment of an object that has been gripped and retrieved. In one example, improved alignment of retrieved cartridges 90 relative to the gripper plate 2020 is provided by rails 2027 that run parallel to sides of the plate 2020 and may extend from the top to the bottom of the plate, as illustrated in FIG. 24.

Automated Loading of Sample Cartridges for AST

FIGS. 27A-27D depict an exemplary cartridge testing instrument 2050. In particular, the depicted cartridge testing instrument 2050 is an AST instrument. However, it should be understood that the principles described herein may be applied to any laboratory instrument where automatic input and removal of a sample cartridge is desired.

Cartridge testing instrument 2050 generally includes a housing 2052 defining a cavity therein and a first or manual door 2060 and second or automatic door 2066 for accessing said cavity. Housing 2052 may include a cartridge holder 2054 disposed in the cavity that includes a plurality of receptacles or cartridge holding structures 2073 for receipt of individual cartridges 90. Cartridge holder 2054 and the receptacles may be moveable within the cavity by activation of a receptacle actuator 2078 (e.g. a motor and belt) so that each receptacle is presentable to a door opening for receiving or removing cartridge 90. In one example, cartridge holder 2054 can be a drum with a plurality of receptacles 2073 that is rotatable around an axis.

Figure 27A:
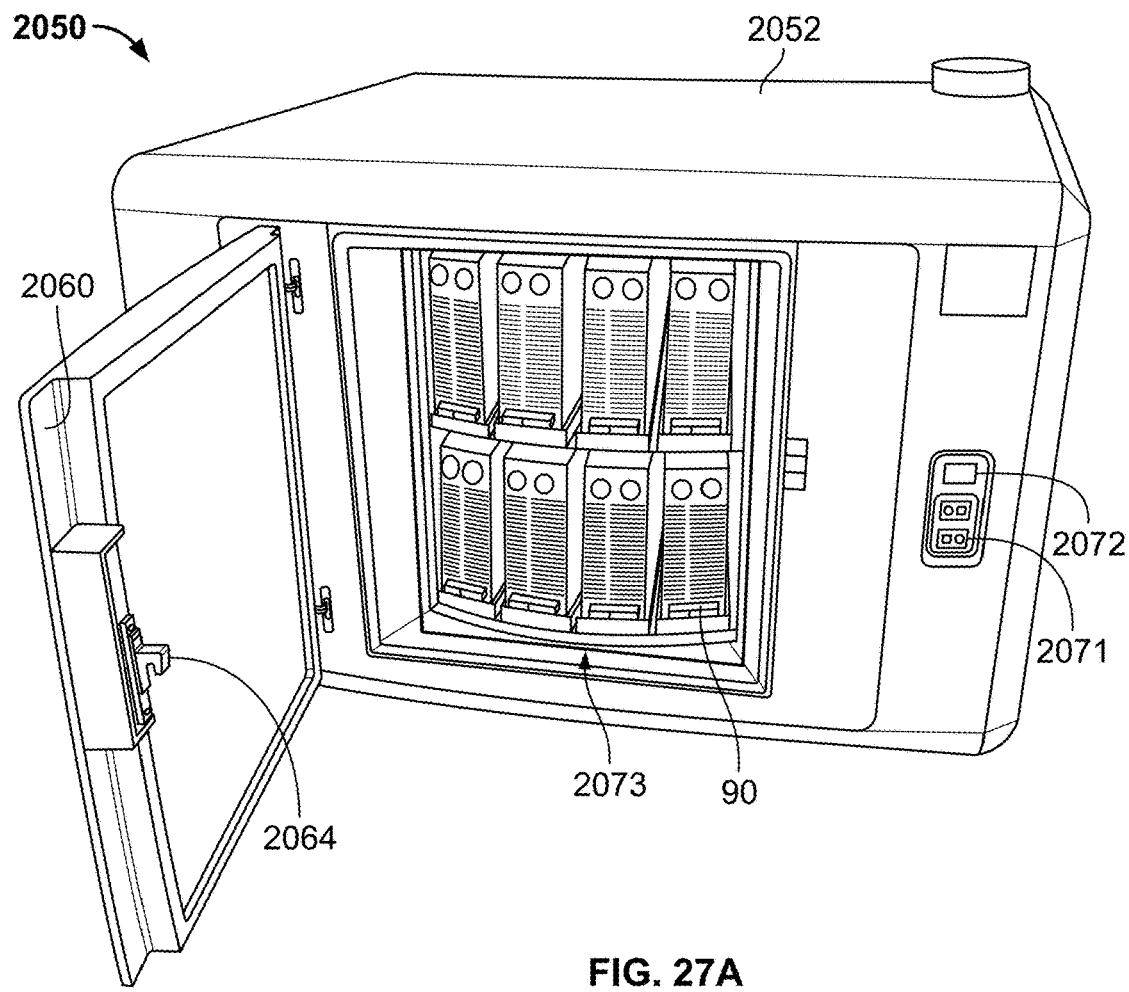
FIG. 27A is a front perspective view of one of the testing instruments of FIG. 20 including a manual door.

As shown in FIG. 27A, first door 2060 is generally located at a first side (deemed the front in this embodiment) of instrument 2050 and is manually operable. First door 2060 is mounted on hinges to housing 2052 and includes a mechanical or magnetic latch 2064 or a deadbolt that can be locked by an automatic locking mechanism 2074 during operation of the testing instrument to prevent first door 2060 from being opened. In an alternative embodiment, rather than being in hinged connection to the housing 2052, first door 2060 can be slidably attached to a track that allows the door to slide open and closed.

Figure 27B:
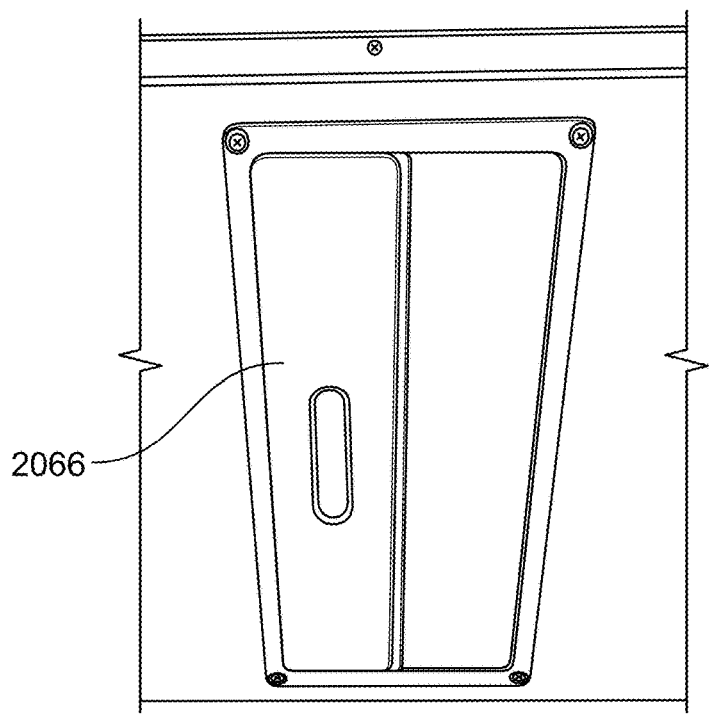
FIG. 27B-27D are various rear views of the testing instrument of FIG. 27A including an automatic door of such instrument.
Figure 27C:
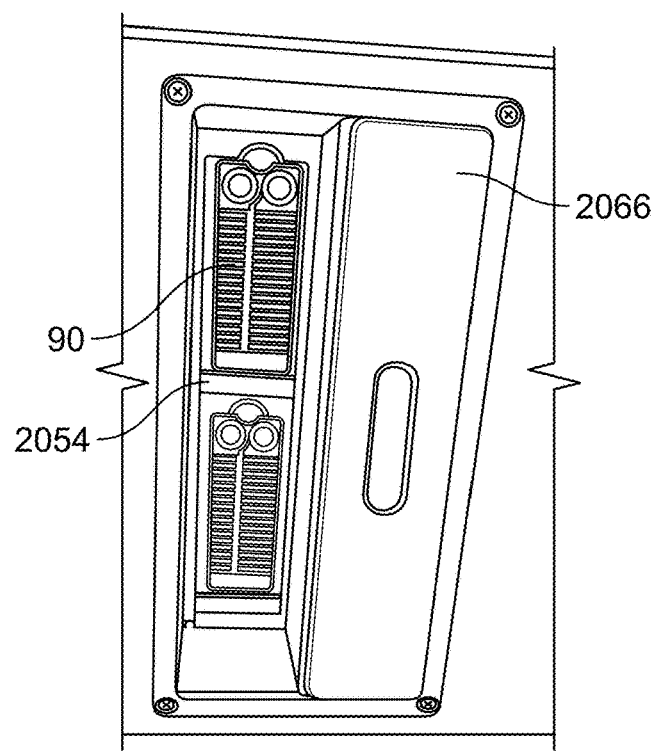
Figure 27D:
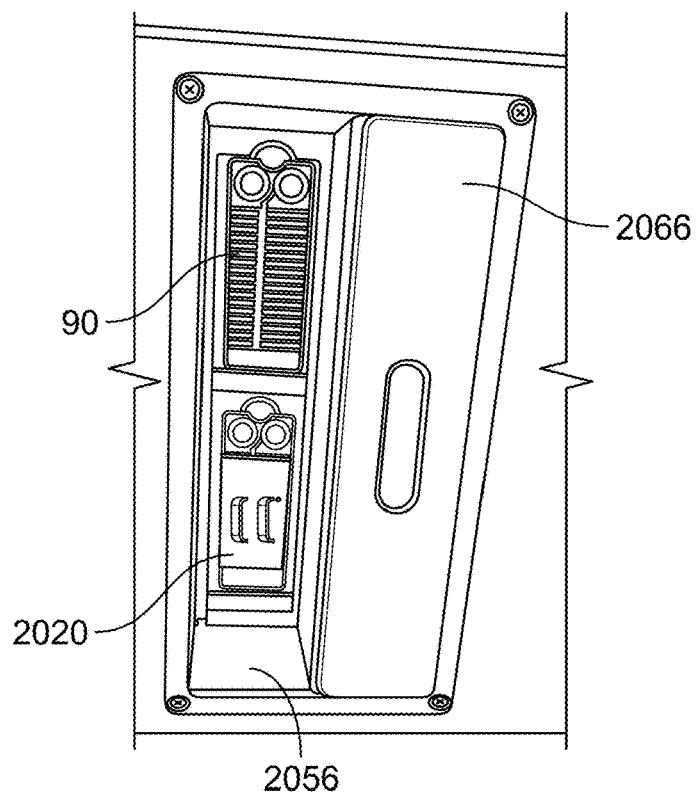

As shown in FIGS. 27B-27D, second door 2066 is generally located at a second side (deemed the rear in this embodiment) of instrument 2050 and is automatically operable. Second door 2066 is slidably positioned in a track 2056 allowing door 2066 to slide from side to side, and coupled to a linear or door actuator 2076, such as a leadscrew, rack and pinion, pneumatic cylinder/piston, motorized linear actuator, or some other mechanical or electro-mechanical device. Such door actuator 2076 opens and closes door 2064. Track 2056 at least partially defines the expanse of the second door opening. Second door 2066 may expose one or a plurality of cartridge holders 2054. Two independently operating rear automatic doors are envisioned allowing the flexibility to expose only the top cartridge holder or bottom cartridge holder. This may necessitate the use of additional tracks 2056 and door actuator 2076.

Testing instrument 2050 may include additional doors, such as a third and fourth door which may be disposed at sides of instrument 2050 and can be either manually or automatically operated. In addition, second door 2066 can be alternatively disposed on a side of instrument 2050 adjacent the front side where first door 2060 is located. In another embodiment, automatic door 2066 can be integrated into manual door 2060 so that during manual operation, automatic door 2066 moves with manual door 2060, and during automatic operation, only automatic door 2066 opens and closes while manual door 2060 remains closed. Of course, it is also contemplated that testing instrument 2050 can have only one door, which can be automatically operated.

As mentioned above, testing instrument 2050 can be incorporated as a component subsystem into a broader system that includes transfer instrument 2000, and preparation system 1000 and that is controlled by controller 30. As such, testing instrument 2050 can include features 2070 that communicate with and/or be operated by controller 30. Such features are illustrated in FIG. 28A and generally include, but are not limited to, a user input interface 2071, a display interface 2072, as well as the locking mechanism 2074, door actuator 2076 and receptacle actuator 2078.

As shown in FIG. 27A, housing 2052 may also include user input interface 2071 and display interface 2072. User interface 2071 can be one or more push buttons or a touch screen that allows the user/operator to input a command or request, such as a manual override request or instruction. For example, when testing instrument 2050 is in automatic mode, controller 30 operates door actuator 2076 for second door 2066 while controller 30 operates locking mechanism 2074 to keep first door 2060 locked. Input interface 2071 may be configured so that a user can override the automatic mode such that when a testing cycle is complete, controller 30 disables door actuator 2076 and operates locking mechanism 2074 allowing the user to open first door 2060. In addition, user input 2071 may be configured to allow the user to further specify whether cartridges 90 are being loaded or unloaded. Controller 30 can then determine whether the appropriate cartridge 90 or receptacle is properly presented to the manual door opening.

Display interface 2072 may be a screen or an LED light. When the user requests manual mode via user input interface 2071, display interface 2072 may present a warning that testing within instrument 2050 is still taking place and that first door 2060 cannot be opened until testing is completed. The display interface 2072 may also display a message or indicate when first door 2060 is unlocked for commencement of manual loading or unloading. Display interface 2072 may also display the present mode of the instrument 2050, whether it is manual or automatic.

Additionally, cartridge transfer instrument 2000 can include features 2041 that communicate with and/or be operated by controller 30. Such features are illustrated in FIG. 28B and generally include, but are not limited to, cartridge gripper 2020, cartridge translation actuator(s) 2030, and cartridge position sensor(s) 2048.

As mentioned above, cartridge gripper plate 2020 may include a vacuum port/suction cup 2028 that provides suction for securing and releasing cartridge 90. The on/off operation of the vacuum pump 2002 that provides such suction may be controlled by controller 30.

Cartridge translation actuators 2030 control movement of transfer instrument 2000. Thus, where transfer instrument 2000 is a robot as previously described, translation actuators 2030 provide robot with automatic degree-of-freedom movement in order to move gripper plate 2020 and any cartridge 90 attached thereto. Controller 30 controls actuators 2030 to direct cartridge movement and also deactivate actuators 2030 when manual mode of testing instrument 2050 is engaged.

In order to determine position and orientation of a cartridge 90 attached to gripper plate 2020, transfer instrument 2000 may include cartridge position sensors 2048, which communicate with controller 30 on a feedback loop to help direct cartridge transfer.

As mentioned above, controller 30 may be a desktop computer or some other computing device and may include a display interface 2072 and user interface 2071, such as a keyboard and mouse. Also, as depicted in FIG. 28C, the controller's computing architecture generally includes a processor 32 and memory 34. As shown in FIG. 28C, controller may also include a subsystem interface 36.

Subsystem interface 36, which can include an external bus, couples controller 30 to the preparation system 1000, cartridge transfer instrument 2000, and cartridge testing instrument 2050. In particular, instructions and data are communicated between controller 30 and components 2070 via the subsystem interface 36.

The memory/data storage 34 can include RAM, ROM, flash memory, and the like. Memory 34 includes processor control instructions 37 and stored data 38. Processor control instructions 37 include instructions related to the operation of the locking mechanism 2074, door actuator 2076, receptacle actuator 2078, and input interface 2071, for example. Stored data 38 may include cartridge identification (such as barcode information or serial numbers), corresponding receptacle identification, and timing information, start time of test and length of test.

In one embodiment of a method involving automated cartridge transfer, cartridge 90 is automatically loaded and automatically unloaded from testing device 2050. In such embodiment, preparation system 1000 prepares the AST cartridge 90 by inoculating cartridge 90 with a sample as described in detail above. More specifically cartridge 90 is inoculated automatically via one or more robots, which may remove an inlet cover 99 (e.g. a cap) of cartridge 90. Pipettor 60 dispenses the analyte into the cartridge 90. Alternatively, the inlet may be covered by a septum, in which case a robot may utilize a needle to inoculate the interior of cartridge 90 through the septum. Thereafter, cartridge 90 may be placed in a pick-up location, such as within transfer station 1040, and preparation system 1000 notifies controller 30 that the cartridge 90 is ready for testing and the time preparation is completed.

Thereafter, controller 30 operates cartridge transfer instrument 2000, which picks up inoculated cartridge 90 and transfers it via gripper assembly 2015 and translation actuators 2030 to a predetermined receptacle for such cartridges in testing instrument 2050. Controller 30 also activates door actuator 2076 and receptacle actuator 2078, which opens second door 2066 of testing instrument 2050 and moves a receptacle into alignment with the second door opening using feedback from cartridge position sensors 2048.

The transfer instrument 2000 then places cartridge 90 into the receptacle and communicates the particular cartridge/receptacle location (which is associated with the other specifics of the cartridge) to controller 30. Transfer instrument 2000 then retrieves additional cartridges 90 as instructed by the controller 30. Typically, the receptacles will be fully populated with cartridges 90 prior to testing. When the cartridge holder 2054 is populated with cartridges 90 as instructed by the controller 30, this is sensed by transfer instrument 2000 or testing instrument 2050 and communicated to controller 30. Controller 30 then operates receptacle actuator 2078, which presents more empty receptacles to the second door opening. Once all of the receptacles are populated by cartridges as instructed by the controller 30, controller 30 activates door actuator 2076, which closes second door 2066 and instructs testing instrument 2050 to begin the test, which, in this embodiment, is AST.

Once testing is completed, controller 30 activates door actuator 2076 and operates cartridge transfer instrument 2000, or another cartridge transfer instrument, to remove the tested cartridges via cartridge translation actuators 2030 from their respective receptacles in testing instrument 2050. Such cartridges may be moved to storage 2006. Alternatively, transfer instrument 2000 may dump the tested cartridges into a disposal container 2004. This process may be continuously performed 24 hours/day, 7 days a week.

In another method embodiment, testing device 2050 can be manually loaded or unloaded. Initially, instrument 2050 may be set in an automatic mode where transfer instrument 2000 performs automatic loading and unloading as described above in relation to the first method embodiment of automatic transfer. However, where a user chooses to perform manual loading or unloading of testing instrument 2050, the user can engage user interface 2071 to set instrument 2050 and the overall system in manual mode. Once user interface 2071 is engaged, testing instrument 2050 notifies controller 30, which disables door actuator 2076 and determines whether there is testing currently being performed. Other subsystems may be deactivated by controller 30, such as cartridge transfer instrument 2000. If testing is not being performed, controller 30 activates locking mechanism 2074, which unlocks first door 2060. If testing is being performed, controller 30 keeps door 2060 locked and notifies or indicates to the user, via display interface 2072, that door 2060 cannot be opened. Once testing is completed, controller 30 unlocks first door 2060 and notifies the user with a notification that it is acceptable to proceed. The user may then open first door 2060 and begin manually loading or unloading testing instrument 2050 with inoculated cartridges 90.

In some embodiments, user interface 2071 provides additional functionality, such as specifying whether manual loading or unloading is desired, rather than just activating manual mode. It is also contemplated that a specific cartridge 90 may be identified for removal. Where the user instructs manual loading, controller 30, along with activating locking mechanism 2074 unlocks first door 2060, and activates receptacle actuator 2078 to move one or more empty receptacles into alignment with the first door opening. Conversely, where manual unloading is selected, controller 30 operates receptacle actuator 2078 to present cartridges that have been tested to the first door opening so that they can be manually unloaded.

System Alternatives

Figure 29:
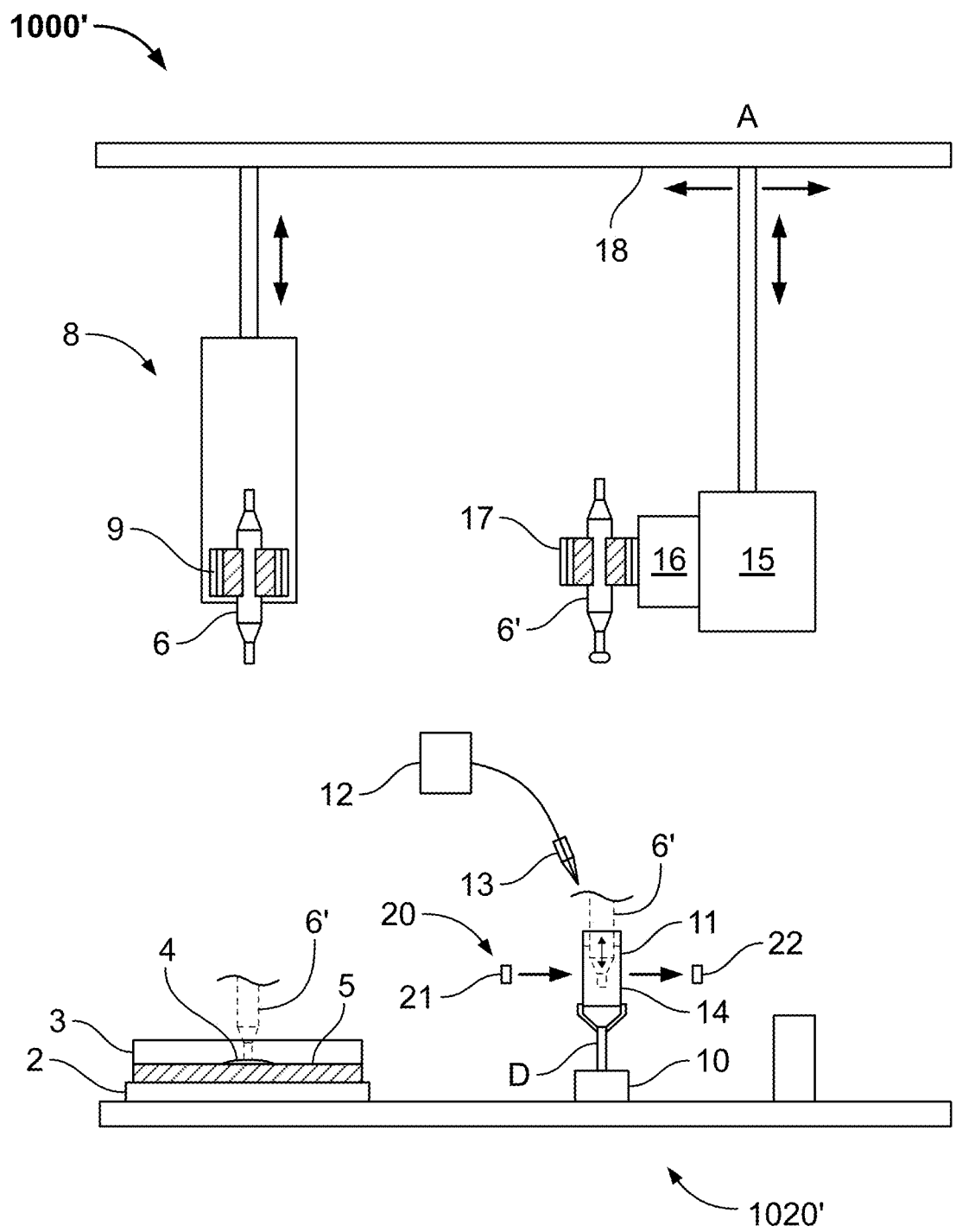
FIG. 29 is a schematic view of a pick station according to another embodiment of the present disclosure.

Numerous variations, additions, and combinations of the features discussed above can be utilized without departing from the present invention. For example, FIG. 29 depicts an alternative preparation system 1000'. System 1000' is similar to system 1000 in that it includes a housing that houses several stations such as receiving station 1010, preparation station 1030, and a transfer station 1040. However, system 1000' differs with regard to its pick station 1020'. As previously described with regard to system 1000, station 1020 includes a positioning device 8 that carries a pick tool 6 and uses such pick tool 6 to pick a sample from a colony 4 on a plate 3 and transfers such picked colony to a suspension tube 11. Such positioning device 8 includes a transferring device 15 that is used to 15 oscillate the pick tool when submerged in the suspension medium.

Station 1020', on the other hand, separates the positioning device 8 and transferring device 15. In this regard, positioning device 8 and transferring device 15 are independently connected to transfer track 18. The transferring device 15 comprises a transfer holder 16 with a grasping tool 17 for releasably holding pick tool 6. In this manner the transferring device 15 may be moved to the positioning device 8, such that the grasping tool 17 can take over the pick tool 6 from the positioning device 8. The pick tool holder 9 releases the pick tool 6 after the grasping means 17 has grasped the pick tool. In the embodiment shown in FIG. 29, the pick tool 6', having previously picked up a sample of the microorganism 4, is positioned above the suspension tube 11 by the transferring device 15 in a starting position indicated by solid lines. The transferring device 15 is arranged for lowering pick tool 6' into the suspension medium 14 contained in the suspension tube 11, in which position the pick tool 6' with the sample 19 is submerged in the suspension medium 14 as indicated by broken lines in FIG. 29. In this position the transferring device 15 is activated for oscillating pick tool 6' in a linear vertical movement for a period of time which is sufficient for the sample to be released from the second pick tool 6'. Thereafter the transferring device 15 positions the pick tool 6, having released its contents, in a waiting position above the suspension tube 11, which waiting position is in the embodiment shown in FIG. 29 identical to the starting position of transfer device 15. Thereafter, transferring device may release pick tool 6 over a waste receptacle during which time positioning device 8 may have already retrieved a second pick tool and a second sample. Thus, in this embodiment positioning device hands off the pick tool to transferring device 15 rather than retaining the pick tool through transfer of the sample to the suspension medium. Such embodiment may be utilized where the pick tool does not require active suction or vacuum to retain the sample.

Figure 30:
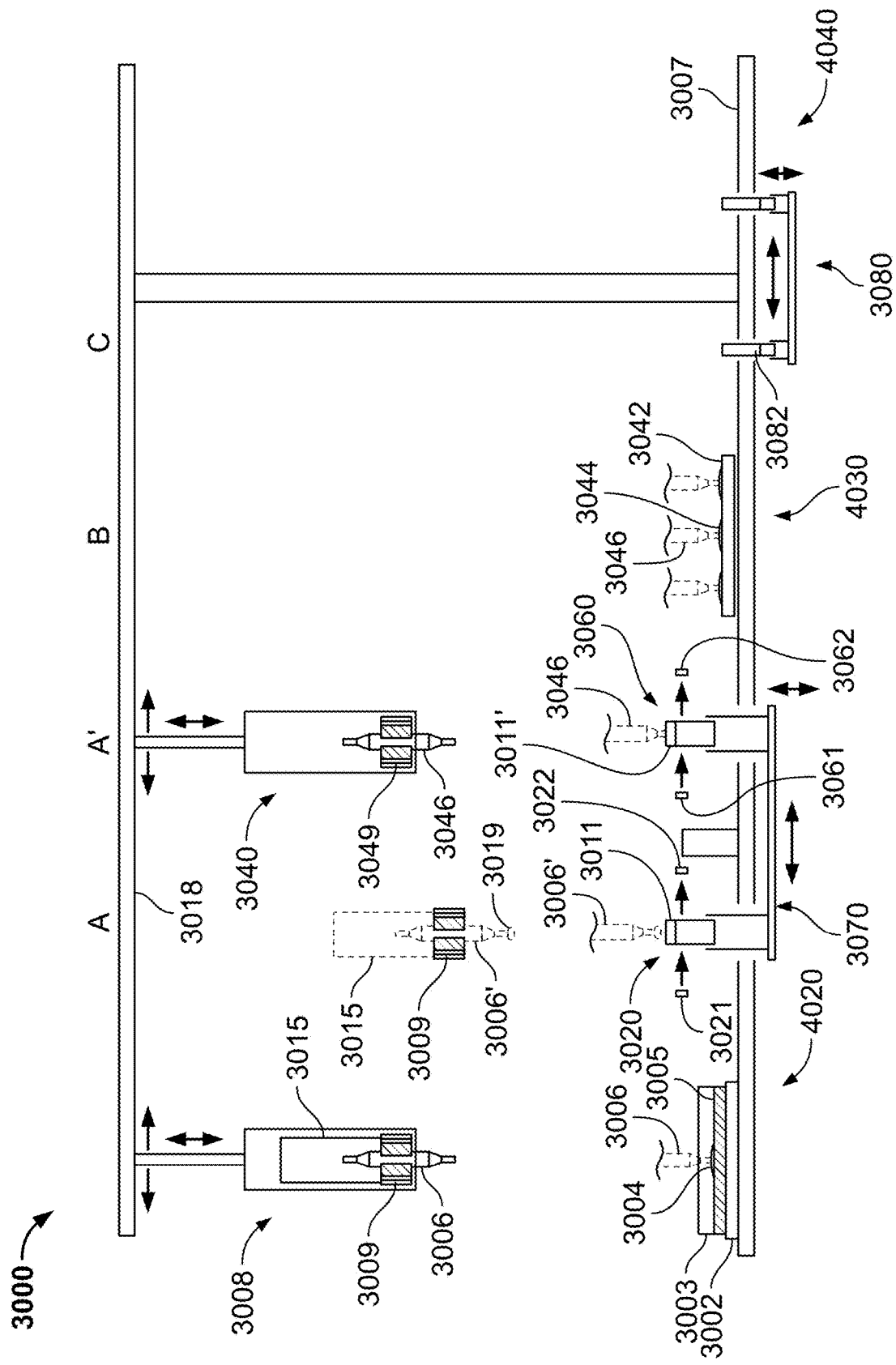
FIG. 30 is a schematic view of a component layout within the system housing of FIG. 1 according to another embodiment of the present disclosure.

Another embodiment preparation system 3000 is depicted in FIG. 30. System 3000 is similar to system 1000 in that it includes a housing that houses several stations such as a receiving station (not shown), pick station 4020, preparation 4030, and a transfer 4040. In addition, pick station 4020 includes a positioning device 3008 that carries a pick tool 3006 and preparation station includes a pipettor 2040 that carries a pipette tip 3046. However, unlike system 1000 where suspension tube 11 remains in the same general location for inoculation with a picked sample 19 via positioning device 8 and suspended sample retrieval via pipettor 40, position device 3008 and pipettor 3040 are relegated to their respective stations 3020, 3030. In other words, pipettor 3040 does not travel from preparation 4030 to pick station 4020 in order to retrieve a suspended sample from suspension tube 3011, rather suspension tube 3011 is moved from pick station 4020, after inoculation by the pick tool 3006, to preparation 4030.

This is achieved by a suspension tube mover 3070. Suspension tube mover 3070 is a robot generally disposed beneath the deck 3007 and is configured to move in at least two dimensions, as illustrated by the double headed arrows in FIG. 30. In particular, suspension tube mover 3007 is configured to hold, such as by a receptacle or gripper, a suspension tube 3011 and move the suspension tube 3011 underneath the deck 3007 and move the suspension tube 3011 between predesignated positions A and A' located at the pick station and preparation station, respectively. In this regard, the deck may have openings through which the mover can raise and lower a suspension tube at these predesignated positions.

In addition, each one of these positions A and A' has a nephelometer 3020, 3060, such as one of the nephelometers previously described, which includes a laser or light emitter 3021, 3061 and a detector 3022, 3062. Thus, a first position A located at the pick station 4020 includes a first nephelometer 3020, and a second position A' located to the preparation 4030 includes a second nephelometer 3060. In one embodiment, the nephelometer is an 8-channel device that can measure the turbidity in eight cuvettes simultaneously, such as by including multiple light sources and detectors.

In a method of using system 3000, a culture dish 3003 is moved from the receiving station to the pick station 4020 and may be positioned on platform 3002. Such dish 3003 includes a culture medium 3005 and one or more microorganism colonies. A target colony 3004 is selected and pick tool 3006 is positioned above the target colony 3004. The pick tool 3006 is lowered to retrieve a sample 3019 of the target colony 3004 via positioning device 3008. Thereafter, positioning device 3008 moves the picked colony 3019 to position A above suspension tube 2011 within pick station 4020. Positioning device 3008 lowers the picked microorganism 3019 and submerges it into a suspension medium within the suspension tube 3011. A transfer device 3015 oscillates the pick tool 3006 so as to release the microorganism into the suspension medium. The nephelometer 3020 measures the turbidity of the suspension. Additional picks of the microorganism 3004 can be performed until the desired turbidity is achieved.

Once the desired turbidity is achieved through successive colony picks, tube mover 3070 lowers the suspension tube 3011' with a microorganism suspension therein until it is beneath deck 3007. Mover then moves the tube 3011' to a second tube position A' located at preparation 4030. Thereafter, mover 3070 raises tube 3011' through the opening in deck 3007 for preparation of a MALDI plate 3042. The MALDI plate is prepared by pipettor 3040 which moves to position A' above tube 3011' and retrieves an aliquot of the suspension therefrom. Pipettor 3040 then moves the aliquot to a position B above MALDI plate 3042 where the pipettor 3040 deposits the aliquot onto the MALDI plate 3040 at predetermined locations 3044, as is described in detail above. Once the MALDI plate 3042 is prepared, the pipettor 3040 may then aspirate deionized water or some other suspension medium into the suspension tube 2011' at the second tube position A'. The nephelometer 3060 at the second tube positon A' measures the turbidity. Once the desired McFarland number is achieved for AST, the pipettor 3040 aspirates an aliquot from the suspension tube 2011' at position A' and then transfers that aliquot to a position C where the pipettor 3040 inoculates an AST broth tube 3082 with the suspension. The AST broth tube 3082 is moved to the transfer 4040 via a AST tube mover 3080 in a similar manner to that of mover 3070 by lowering the tube beneath deck 3007 and transporting it under the deck to a position within the transfer 4040. From there, the sample within the AST tube 3082 is inoculated into AST cartridges 90 as previously described.

In other embodiments of system 3000, preparation 4030 may include two tube positions so that the system includes three total suspension tube positions, one in the pick station 4020 and two in the preparation 4030. In such an embodiment, one of the tube positions within the preparation 4030 may be utilized for MALDI plate preparation, while the other position within the preparation 4030 may be utilized to prepare AST tubes 3082. In this regard, the tube position for MALDI preparation may not have a nephelometer as the suspension turbidity for MALDI preparation would have been determined by the nephelometer 3020 at pick station 4020. However, the suspension tube position for AST tube preparation would have nephelometer 3060 so as to assist the pipettor 2040 in diluting the suspension to the appropriate McFarland number for AST.

The invention claimed is:

1. An automated system for preparing a single sample suspension from which aliquots are removed for both identification (ID) of microorganisms in the sample and antibiotic susceptibility testing (AST) assay of microorganisms in the sample, the system comprising:
   a controlling means comprising a processor and a memory;
   a first section for preparing a sample for an ID assay, the first section comprising:
   a means for receiving a plated culture in a culture dish; the system configured to communicate with an imaging means for obtaining an image of the plated culture and a means to identify a colony on the plated culture and designating that colony for automated sample pick from the obtained image;
   a first automated apparatus for automatic handling of a pick tool;
   a means for communicating a location of the colony from the controlling means to the first automated apparatus;
   wherein the controlling means controls a pick of the colony by the first automated apparatus wherein the first automated apparatus is further configured to convey the picked sample to a first sample suspension preparation station;
   a means for providing a suspension liquid into a suspension tube at the first sample preparation station wherein the automated pick tool is configured to deposit the picked sample into the suspension liquid in the suspension tube to form a suspension;
   a nephelometer at the first station for measuring the turbidity of the suspension liquid in the suspension tube, wherein the automated system, in response to the turbidity measurement that is outside a predetermined turbidity value, adjusts one of either an amount of sample or an amount of suspension in the suspension tube to provide a suspension with a concentration of sample in a predetermined range;
   a second automated apparatus, wherein the second automated apparatus is a pipettor that obtains a first aliquot of the suspension in the suspension tube at the first station and inoculates a receptacle for use in the ID assay;
   a first means for conveying the suspension tube with a remaining portion of the suspension from the first sample suspension preparation station to a second sample suspension preparation station;
   a detector for detecting if a string of sample is formed as the first automated apparatus conveys the pick tool carrying the sample from the culture dish;
   wherein the second automated apparatus is further configured to adjust the concentration of the remaining portion of the suspension in the suspension tube to a predetermined concentration for a second assay and for obtaining a second aliquot of the sample suspension having adjusted concentration and inoculating a tube for the AST assay with the second aliquot of suspension; and
   a second section for inoculating a panel for the AST assay; wherein the automated system has a second means for conveying the inoculated sample tube from the first section to the second section;
   the second section having a third automated apparatus that is a pipettor that obtains an aliquot from the inoculated tube for the AST assay and inoculates the AST panel with the obtained aliquot; and
   a loading robot that loads the inoculated AST panel into an apparatus in which the AST assay is performed.

2. The system of claim 1, wherein the AST apparatus comprises at least two doors, a first door receiving the panel from the loading robot for transfer of the inoculated AST panel wherein the loading robot is a panel gripper including a gripper plate, the gripper plate coupled to an arm of a three-axis stepper-motor-controlled fixture such that the gripper plate is adapted to pivot about an axis of coupling from a first position to a second position; and wherein the gripper plate includes a gripping surface that is adapted to grip onto objects.

3. The system of claim 2, wherein the string is detected by monitoring the pick tool optically or electrically as the pick tool is raised away from the culture dish.

4. The system of claim 3, further comprising a mechanism for severing the string, wherein the mechanism severs the string by one of cutting the string, sonicating the string, drying the string, or freezing the string.

5. The system of claim 4, wherein the mechanism for cutting the string is selected from the group consisting of a laser, a rod, a wire, and a blade.

6. The system of claim 5, wherein the mechanism for cutting the string is heated.

7. An automated system for preparing a single sample suspension from which aliquots are removed for identification (ID) of microorganisms in the sample and a second test, the system comprising:
 a controlling means comprising a processor and a memory;
 at least a first section for preparing the sample for an ID assay, the first section comprising:
 a means for receiving a plated culture;
 the automated system configured to communicate with an imaging means for providing image information of a plated colony that is used to identify a colony on the plated culture and designate that colony for automated sample pick;
 an automated pick tool;
 a means for communicating a location of the colony to the automated pick tool;
 wherein the controlling means controls a pick of the colony by the automated pick tool wherein the automated pick tool is further configured to convey the picked sample to a first sample suspension preparation station;
 a detector for detecting if a string of sample is formed as the automated pick tool conveys the sample from the plated culture wherein the string is detected by monitoring the pick tool optically or electrically as the pick tool is raised away from the plated culture;
 a mechanism for severing the string, wherein the mechanism severs the string by one of cutting the string, sonicating the string, drying the string, or freezing the string;
 a means for providing a suspension liquid into a suspension tube at the first sample preparation station wherein the automated pick tool is configured to deposit the picked sample into the suspension liquid to form a suspension;
 a nephelometer at the first station for measuring the turbidity of the suspension, wherein the automated system, in response to a turbidity measurement that is outside a predetermined turbidity value, adjusts one of either an amount of sample or an amount of suspension in the suspension tube to provide a suspension with a concentration of sample in a predetermined range;
 a first automated pipettor, wherein the first automated pipettor obtains a first aliquot of the suspension at the first station and inoculates a receptacle for use in the ID assay;
 a first means for conveying the suspension tube with a remaining portion of the suspension from the first sample suspension preparation station to a second sample suspension preparation station;
 wherein the first automated pipettor is further configured to acquire a volume of the remaining portion of the suspension tube to obtain a predetermined amount of sample for a second assay;
 a second section for inoculating a panel for the AST assay; wherein the automated system has a second means for conveying the suspension tube from the first section to the second section;
 the second section having a second automated pipettor that obtains an aliquot from the suspension tube and inoculates the AST panel with the obtained aliquot;
 a housing defining an interior space of an AST apparatus for receipt of a cartridge containing an analyte for testing;
 a first door coupled to the housing at a first side thereof and being configured to receive a plurality of panels for AST testing in the interior of the housing, wherein the first door is operated manually;
 a second door coupled to the housing at a second side thereof wherein the second door is operated automatically; and
 a door actuator coupled to the second door and configured to operate the door upon automatic activation of the door actuator to receive a plurality of panels for testing in the interior of the housing, and
 a panel loading robot that loads the inoculated AST panel into the AST apparatus, wherein the second door coupled to the housing receives the panel from the panel loading robot wherein the panel loading robot is a panel gripper including a gripper plate, the gripper plate coupled to an arm of a three-axis stepper-motor-controlled fixture such that the gripper plate is adapted to pivot about an axis of coupling from a first position to a second position; and wherein the gripper plate includes a gripping surface that is adapted to grip onto objects.

* * * * *